(12) United States Patent
Kim et al.

(10) Patent No.: US 12,275,977 B2
(45) Date of Patent: Apr. 15, 2025

(54) METHOD FOR BIOLOGICALLY PRODUCING ACETIN COMPOUND

(71) Applicants: INDUSTRY-ACADEMIC COOPERATION FOUNDATION GYEONGSANG NATIONAL UNIVERSITY, Gyeongsangnam-do (KR); KYUNGPOOK NATIONAL UNIVERSITY INDUSTRY-ACADEMIC COOPERATION FOUNDATION, Daegu (KR)

(72) Inventors: Seon Won Kim, Sejong-si (KR); Seong Hee Jeong, Gyeongsangnam-do (KR); Kyung Jin Kim, Daegu (KR); Zada Bakht, Gyeongsangnam-do (KR)

(73) Assignees: INDUSTRY-ACADEMIC COOPERATION FOUNDATION GYEONGSANG NATIONAL UNIVERSITY, Gyeongsangnam-Do (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 843 days.

(21) Appl. No.: 17/288,761

(22) PCT Filed: Oct. 28, 2019

(86) PCT No.: PCT/KR2019/014256
§ 371 (c)(1),
(2) Date: Apr. 26, 2021

(87) PCT Pub. No.: WO2020/085879
PCT Pub. Date: Apr. 30, 2020

(65) Prior Publication Data
US 2022/0112527 A1    Apr. 14, 2022

(30) Foreign Application Priority Data
Oct. 26, 2018 (KR) .............. 10-2018-0129090

(51) Int. Cl.
| | |
|---|---|
| *C12P 7/28* | (2006.01) |
| *C12N 1/20* | (2006.01) |
| *C12N 9/10* | (2006.01) |
| *C12N 9/16* | (2006.01) |
| *C12N 15/52* | (2006.01) |
| *C12R 1/19* | (2006.01) |

(52) U.S. Cl.
CPC .............. *C12P 7/28* (2013.01); *C12N 1/20* (2013.01); *C12N 9/1033* (2013.01); *C12N 9/16* (2013.01); *C12N 15/52* (2013.01); *C12R 2001/19* (2021.05); *C12Y 203/01028* (2013.01); *C12Y 301/01006* (2013.01)

(58) Field of Classification Search
CPC ..... C12P 7/28; C12P 7/62; C12N 1/20; C12N 9/1033; C12N 15/52; C12N 9/1029; C12R 2001/19; C12Y 203/01028; C12Y 301/01006; C12Y 101/01008; C12Y 203/01079; C12Y 301/03021
See application file for complete search history.

(56) References Cited

U.S. PATENT DOCUMENTS 4,381,407 A     4/1983   Bremus et al.
2015/0322412 A1  11/2015  Farrell et al.

FOREIGN PATENT DOCUMENTS

| CN | 102030614 A | 4/2011 |
| CN | 103159622 A | 6/2013 |
| JP | 2008245600 A | * 10/2008 |
| KR | 10-1590268 B1 | 2/2016 |
| WO | WO 96/33678 A1 | 10/1996 |

OTHER PUBLICATIONS

Tsou et al. Microbios., 1998, 94, 133 (Year: 1998).*
GenBank AJ223173.1, [retrieved on Oct. 7, 2024]. Retrieved from the Internet: <*Escherichia coli* Maltose Transacetylase orf (maa)—Nucleotide—NCBI (nih.gov)>, 2016 (Year: 2016).*
Oterholm et al., J. Dairy Science, 1972, 55, 8-13 (Year: 1972).*
Taherzadeh et al. Enzyme and Microbiology technology, 2002, 31, 53-66) (Year: 2002).*
Norbeck et al. J. Biol. Chem., 1996, 271, 13875-13881 (Year: 1996).*
Habe et al. J. Oleo Science, 2009, 58, 147-154 (Year: 2009).*
Leggio et al. Biochemistry, 2003, 42, 5225-5235 (Year: 2003).*
Millipore Sigma, [retrieved on Mar. 7, 2024]. Retrieved from the Internet: <https://www.sigmaaldrich.com/US/en/product/sial/crm10006I>, p. 1-6 (Year: 2024).*
ATCC [retrieved on Mar. 7, 2024]. Retrieved from the Internet: <https://genomes.atcc.org/genomes/b5db387eb6914efb?tab=annotations-tab>, p. 1-9 (Year: 2024).*
Bakht Zada et al., "Metabolic engineering of *Escherichia coli* for production of non-natural acetins from glycerol", Green Chem, 2020, vol. 22, No. 22, pp. 7569-8048, DOI: 10.1039/D0GC02395G.
International Search Report for PCT/KR2019/014256 mailed on Feb. 5, 2020.
Tsoul MF et al., "Characterization of arylamine N-acetyltransferase in Enterobacter aerogenes." Microbios, vol. 94 (379): pp. 133-143, 1998 (English abstract is submitted herewith).

(Continued)

*Primary Examiner* — Thea D'Ambrosio
*Assistant Examiner* — Lioubov G Korotchkina
(74) *Attorney, Agent, or Firm* — The PL Law Group, PLLC

(57) ABSTRACT

A method for biologically producing acetin such as monoacetin, diacetin, or triacetin according to an embodiment of the present disclosure includes reacting acetyl-CoA with glycerol in the presence of a first O-acetyl transferase to obtain the acetin. With the method, acetin which is sustainable and safe, and has more excellent quality while not causing environmental pollution may be obtained.

16 Claims, 22 Drawing Sheets

Specification includes a Sequence Listing.

(56) References Cited

OTHER PUBLICATIONS

Seokhyeon Oh et al., "Enzymatic production of glycerol acetate from glycerol", Enzyme and Microbial Technology, vol. 69, pp. 19-23, 2015.

* cited by examiner

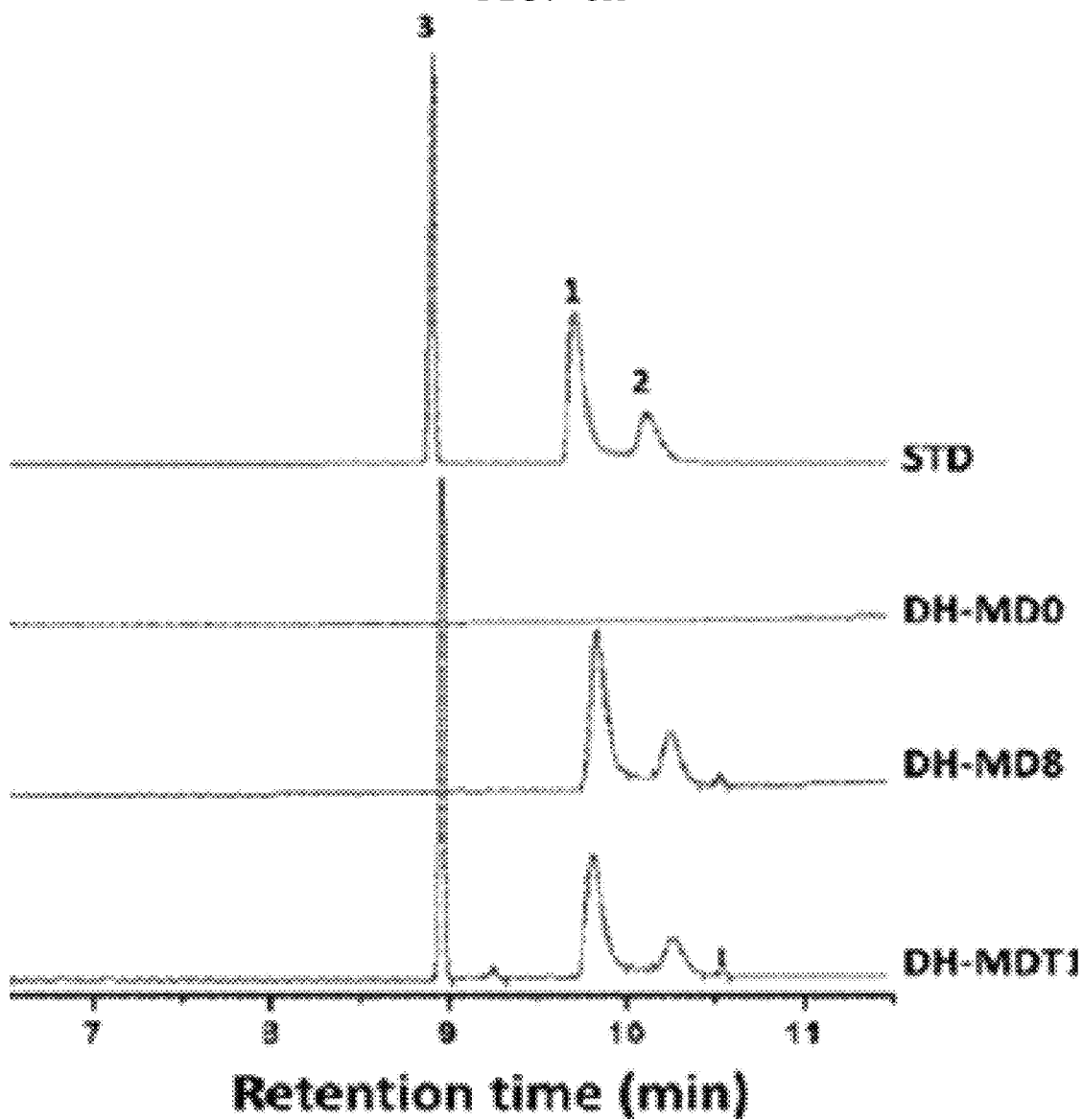

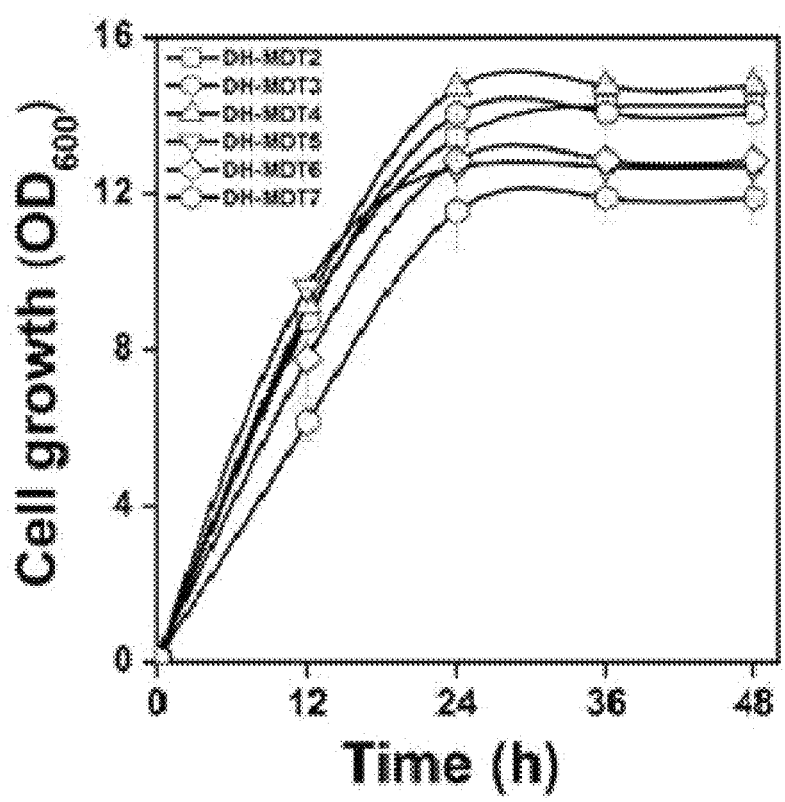

METHOD FOR BIOLOGICALLY PRODUCING ACETIN COMPOUND

PRIORITY

This application claims benefit under 35 U.S.C. 119(e), 120, 121, or 365(c), and is a National Stage entry from International Application No. PCT/KR2019/014256, filed Oct. 28, 2019, which claims priority to the benefit of Korean Patent Application No. 10-2018-0129090 filed in the Korean Intellectual Property Office on Oct. 26, 2018, the entire contents of which are incorporated herein by reference.

BACKGROUND

Technical Field

The present invention relates to a method for producing an acetin compound and a composition for producing acetin.

Background Art

Acetin is a substance in which an acetyl group is ester-linked to a hydroxyl group (—OH) of glycerol, and according to the number of linked acetyl groups, is divided into monoacetin having one bonded acetyl group, diacetin having two bonded acetyl groups, and triacetin having three bonded acetyl groups. In particular, triacetin is also known as glycerin triacetate or triglyceride 1,2,3-triacetoxypropane.

Acetin is used as a food additive such as fragrance solvents and wetting agents, and also is used as a moisturizer, plasticizer and solvent in the pharmaceutical industry. Triacetin may be used as an antiknock agent to reduce knocking in a gasoline engine, and as a fuel additive to improve low temperature and viscosity properties of biodiesel. To produce acetin useable as a fuel additive for biodiesel using waste glycerol, that is, byproducts generated in a great amount, there is a technology provided in the art, which is capable of realizing the concept of Zero-Wastes, which is currently being a hot topic in bio-refinery industry in order to reduce or recycle wastes or byproducts. According to 1994 reports published by the top five (5) tobacco companies, triacetin is one of the tobacco additives and is also used as a plasticizer in a process for manufacturing tobacco filters. Further, triacetin is also used as an important ingredient in artificial space foods for supplying more than half of the energy required to astronauts who execute log space flight missions. The U.S. Food and Drug Administration (FDA) recognizes triacetin as a very safe food additive ("Generally Recognized as Safe: GRAS").

Meanwhile, an acetin material is a viscous, colorless and odorless liquid. The existing acetin material is an artificially synthesized chemical material in which acetic acid or acetic anhydride is combined with glycerol through a chemical reaction.

No biological method for production of acetin has been disclosed. However, there is continuously a need for a method for producing an acetin material through a biological process, thereby is safe and has more excellent quality while not causing any environmental problem.

The present inventors have found that acetin compounds can be produced in a biological way using enzymes which bind acetyl groups to glycerol or derivatives of glycerol through an esterification reaction, and trace amounts of monoacetin are produced from some of intestinal bacteria (Enterobacteriaceae) using glycerol as a carbon source in nature.

Accordingly, the present inventors have prepared a recombinant microorganism capable of producing monoacetin, diacetin, and triacetin using glycerol or glucose as a starting substrate, and have completed the present invention (FIGS. 1 and 2).

SUMMARY

It is an object of the present invention to provide a method for biologically producing an acetin compound and a composition for production of the acetin compound.

To achieve the above objects, the following technical solutions are adopted in the present invention.

1. A method for production of acetin, including reacting acetyl-CoA with glycerol in the presence of a first O-acetyl transferase to obtain the acetin including at least one of monoacetin or diacetin.

2. The method according to the above 1, wherein the first O-acetyl transferase is maltose O-acetyl transferase.

3. The method according to the above 1, wherein, in the first O-acetyl transferase, a sequence motif includes: aspartic acid (ASP) at a position corresponding to position 70 of the amino acid sequence of SEQ ID NO: 5; asparagine (ASN) at a position corresponding to position 84 of the amino acid sequence of SEQ ID NO: 5; histidine (HIS) at a position corresponding to position 114 of the amino acid sequence of SEQ ID NO: 5; and glutamic acid (GLU) at a position corresponding to position 126 of the amino acid sequence of SEQ ID NO: 5.

4. The method according to the above 3, wherein, in the first O-acetyl transferase, a sequence motif includes: tyrosine (TYR) or phenylalanine (PHE) at a position corresponding to position 15 of the amino acid sequence of SEQ ID NO: 5; arginine (ARG) or glutamine (GLN) at a position corresponding to position 26 of the amino acid sequence of SEQ ID NO: 5; arginine (ARG) or lysine (LYS) at a position corresponding to position 30 of the amino acid sequence of SEQ ID NO: 5; and phenylalanine (PHE) or tyrosine (TYR) at a position corresponding to position 82 of the amino acid sequence of SEQ ID NO: 5.

5. The method according to the above 1, wherein the first O-acetyl transferase is composed of any one sequence of SEQ ID NOS: 1 to 6.

6. The method according to the above 1, further including reacting diacetin as a reaction product with acetyl-CoA in the presence of a second O-acetyl transferase, thus to obtain triacetin.

7. The method according to the above 6, wherein, in the second O-acetyl transferase, a sequence motif includes: cysteine (CYS) or leucine (LEU) at a position corresponding to position 31 of the amino acid sequence of SEQ ID NO: 7; phenylalanine (PHE) or isoleucine (ILE) at a position corresponding to position 102 of the amino acid sequence of SEQ ID NO: 7; phenylalanine (PHE) or tyrosine (TYR) at a position corresponding to position 143 of the amino acid sequence of SEQ ID NO: 7; phenylalanine (PHE) or tyrosine (TYR) at a position corresponding to position 166 of the amino acid sequence of SEQ ID NO: 7; valine (VAL), isoleucine (ILE) or leucine (LEU) at a position corresponding to position 170 of the amino acid sequence of SEQ ID NO: 7; and histidine (HIS) at a position corresponding to position 193 of the amino acid sequence of SEQ ID NO: 7.

8. The method according to 6, wherein the second O-acetyl transferase is composed of any one sequence of SEQ ID NOS: 7 to 10.

9. A method for production of acetin, including culturing a microorganism that expresses a gene encoding a first O-acetyl transferase in a medium containing glycerol.

10. The method according to the above 9, wherein the first O-acetyl transferase is maltose O-acetyl transferase.

11. The method according to the above 9, wherein the first O-acetyl transferase has the amino acid sequence of SEQ ID NO: 5.

12. The method according to the above 9, wherein, in the first O-acetyl transferase, a sequence motif includes: tyrosine (TYR) or phenylalanine (PHE) at a position corresponding to position 15 of the amino acid sequence of SEQ ID NO: 5; arginine (ARG) or glutamine (GLN) at a position corresponding to position 26 of the amino acid sequence of SEQ ID NO: 5; arginine (ARG) or lysine (LYS) at a position corresponding to position 30 of the amino acid sequence of SEQ ID NO: 5; and phenylalanine (PHE) or tyrosine (TYR) at a position corresponding to position 82 of the amino acid sequence of SEQ ID NO: 5.

13. The method according to the above 9, wherein the gene encoding the first O-acetyl transferase is composed of any one sequence of SEQ ID NOS: 16 to 21.

14. The method according to the above 9, wherein the microorganism further expresses a gene encoding a second O-acetyl transferase that transfers an acetyl group to diacetin.

15. The method according to the above 14, wherein, in the second O-acetyl transferase, a sequence motif includes: cysteine (CYS) or leucine (LEU) at a position corresponding to position 31 of the amino acid sequence of SEQ ID NO: 7; phenylalanine (PHE) or isoleucine (ILE) at a position corresponding to position 102 of the amino acid sequence of SEQ ID NO: 7; phenylalanine (PHE) or tyrosine (TYR) at a position corresponding to position 143 of the amino acid sequence of SEQ ID NO: 7; phenylalanine (PHE) or tyrosine (TYR) at a position corresponding to position 166 of the amino acid sequence of SEQ ID NO: 7; valine (VAL), isoleucine (ILE) or leucine (LEU) at a position corresponding to position 170 of the amino acid sequence of SEQ ID NO: 7; and histidine (HIS) at a position corresponding to position 193 of the amino acid sequence of SEQ ID NO: 7.

16. The method according to the above 14, wherein the gene encoding the second O-acetyl transferase is composed of any one sequence of SEQ ID NOS: 24 to 27.

17. The method according to the above 9, wherein the microorganism includes a gene encoding acetylesterase, which is attenuated or deleted.

18. The method according to the above 9, wherein the microorganism further expresses genes encoding glycerol-3-phosphate dehydrogenase and glycerol-3-phosphatase ("DL-glycerol-3-phosphatase"), and the medium includes glucose.

19. A composition for producing acetin, including a microorganism that expresses a gene encoding a first O-acetyl transferase.

20. The composition according to the above 19, wherein the first O-acetyl transferase is maltose O-acetyl transferase.

21. The composition according to the above 19, wherein, in the first O-acetyl transferase, a sequence motif includes: aspartic acid (ASP) at a position corresponding to position 70 of the amino acid sequence of SEQ ID NO: 5; asparagine (ASN) at a position corresponding to position 84 of the amino acid sequence of SEQ ID NO: 5; histidine (HIS) at a position corresponding to position 114 of the amino acid sequence of SEQ ID NO: 5; and glutamic acid (GLU) at a position corresponding to position 126 of the amino acid sequence of SEQ ID NO: 5.

22. The composition according to the above 19, wherein, in the first O-acetyl transferase, a sequence motif includes: tyrosine (TYR) or phenylalanine (PHE) at a position corresponding to position 15 of the amino acid sequence of SEQ ID NO: 5; arginine (ARG) or glutamine (GLN) at a position corresponding to position 26 of the amino acid sequence of SEQ ID NO: 5; arginine (ARG) or lysine (LYS) at a position corresponding to position 30 of the amino acid sequence of SEQ ID NO: 5; and phenylalanine (PHE) or tyrosine (TYR) at a position corresponding to position 82 of the amino acid sequence of SEQ ID NO: 5.

23. The composition according to the above 19, wherein the gene encoding the first O-acetyl transferase is composed of any one sequence of SEQ ID NOS: 16 to 21.

24. The composition according to the above 19, wherein the microorganism further expresses a gene encoding a second O-acetyl transferase that transfers an acetyl group to diacetin.

25. The composition according to the above 24, wherein, in the second O-acetyl transferase, a sequence motif includes: cysteine (CYS) or leucine (LEU) at a position corresponding to position 31 of the amino acid sequence of SEQ ID NO: 7; phenylalanine (PHE) or isoleucine (ILE) at a position corresponding to position 102 of the amino acid sequence of SEQ ID NO: 7; phenylalanine (PHE) or tyrosine (TYR) at a position corresponding to position 143 of the amino acid sequence of SEQ ID NO: 7; phenylalanine (PHE) or tyrosine (TYR) at a position corresponding to position 166 of the amino acid sequence of SEQ ID NO: 7; valine (VAL), isoleucine (ILE) or leucine (LEU) at a position corresponding to position 170 of the amino acid sequence of SEQ ID NO: 7; and histidine (HIS) at a position corresponding to position 193 of the amino acid sequence of SEQ ID NO: 7.

26. The composition according to 24, wherein the gene encoding the second O-acetyl transferase is composed of any one sequence of SEQ ID NOS: 24 to 27.

27. The composition according to the above 19, wherein the microorganism includes a gene encoding acetylesterase, which is attenuated or deleted.

28. The composition according to the above 19, wherein the microorganism further expresses genes encoding glycerol-3-phosphate dehydrogenase and DL-glycerol-3-phosphatase.

According to the present invention, there is provided a method for producing an acetin material through a biological process, thereby the produced acetin material is sustainable and safe, and has more excellent quality while not causing environmental pollution.

BRIEF DESCRIPTION OF THE DRAWINGS

FIGS. 5A and 5B: FIG. 5A is a gas chromatogram diagram showing GC analysis of a mixed standard compound (STD) of monoacetin (1), diacetin (2) and triacetin (3) and a culture medium of recombinant *E. coli* DH-MD06, DH-MD8 and DH-MDT1 after extraction of the same with ethyl acetate; and FIG. 5B is a diagram illustrating comparison of mass spectrometry of monoacetin, diacetin, and triacetin obtained in each sample by GC-MS to that of the STD.

FIG. 6A is a structural diagram of plasmid pMDT2 prepared by cloning chloramphenicol-O-acetyl transferase gene (cat) and *B. subtilis* Maa gene (Bs-maa), which convert diacetin into triacetin, into the pTrc99A expression vector; FIGS. 6B and 6C are diagrams respectively illustrating comparison of the productivity and constitutional composition of acetin complex of the recombinant *E. coli* DH-MDT2 transformed with the above plasmid to the control DH-MDT1; and FIG. 6D illustrates a change in productivity to culture time of the acetin complex in the recombinant *E. coli* DH-MDT2.

FIGS. 7A to 7C: FIG. 7A is a structural diagram of plasmids pMDT2 to pMDT7 prepared by finding candidate genes in various microorganisms, which are deduced to transfer an acetyl group to diacetin based on the structure and amino acid sequence of chloramphenicol O-acetyl transferase, and then, cloning the same into plasmid pMD13; FIG. 7B is a diagram illustrating comparison of production amounts of acetin complex of the recombinant strains DH-MDT2 to DH-MDT7 transformed with the above plasmids; and FIG. 7C is a diagram illustrating comparison of strain proliferation of the recombinant strains.

FIGS. 8A to 8F are diagrams illustrating comparison of the productivity of acetin complex to *E. coli* species and glycerol concentration, wherein: FIG. 8A illustrates comparison of the productivity of acetin complex by culturing the recombinant *E. coli* DH-MDT2, AC-MDT2, BW-MDT2, W3-MDT2 and MG-MDT2, which were transformed from *E. coli* DH5α, AceCo, BW25113, W3110 and MG1655 with the plasmid pMDT2; FIG. 8B illustrates comparison of strain proliferation of the above recombinant *E. coli*; FIG. 8C illustrates the productivity of acetin complex to glycerol concentration in the culture of the recombinant strain MG-MDT2; and FIG. 8D illustrates comparison of strain proliferation to glycerol concentration of the above strains.

DETAILED DESCRIPTION

Figure 1:
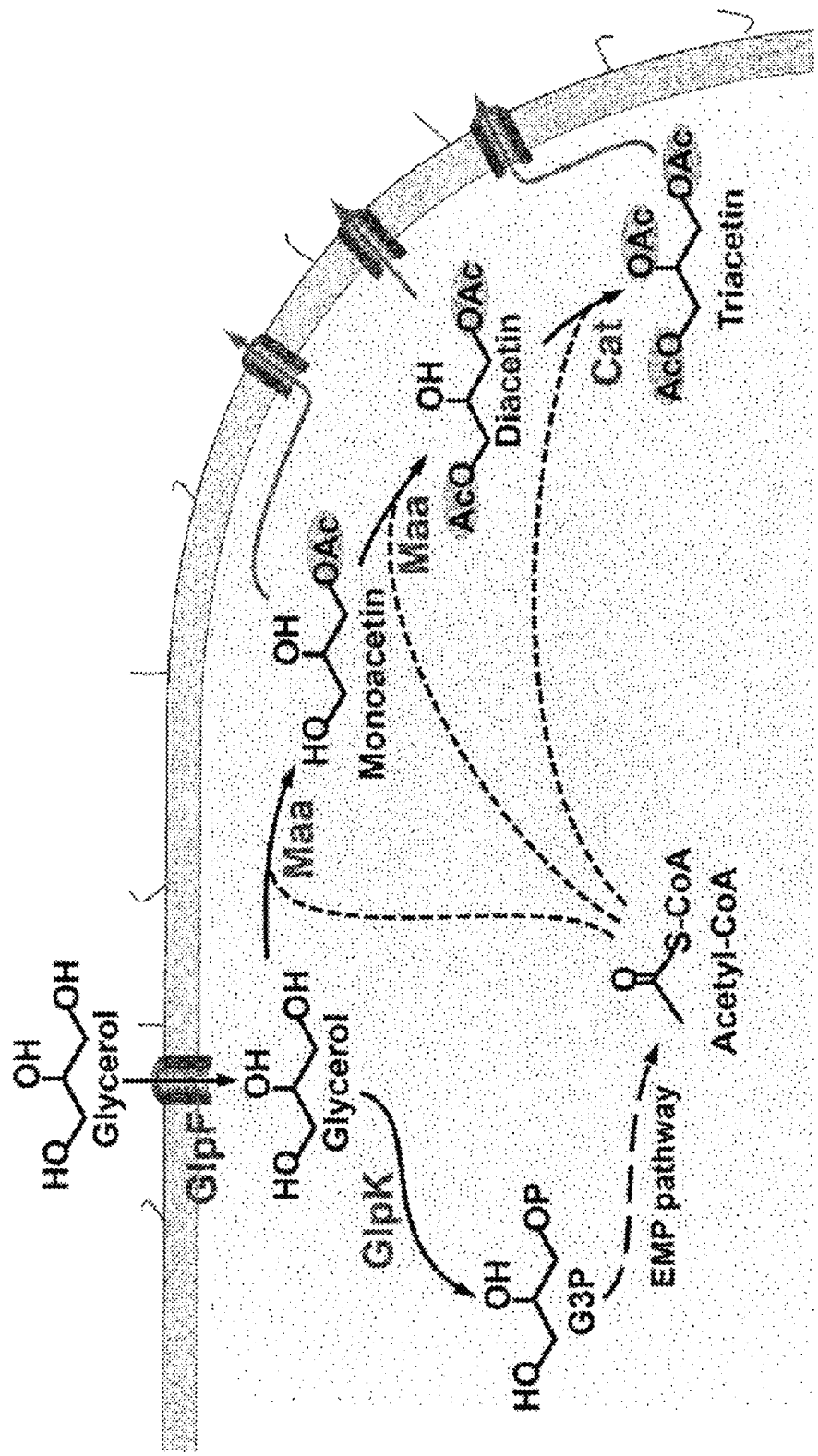
FIG. 1 illustrates a pathway in which glycerol introduced into cells is converted into monoacetin, diacetin and triacetin.

Hereinafter, the present invention will be described in detail.

The present invention relates to a method for production of acetin, which includes: reacting acetyl-CoA with glycerol in the presence of a first O-acetyl transferase to obtain monoacetin or diacetin.

The first O-acetyl transferase may transfer O-acetyl to glycerol in the acetyl-CoA, and may be, for example, maltose O-acetyl transferase, but it is not limited thereto.

The first O-acetyl transferase may be derived from an organism or may be synthesized.

In addition, the first O-acetyl transferase may be expressed in a microorganism having a gene encoding the first O-acetyl transferase, and the gene encoding the first O-acetyl transferase in the microorganism may be inherent in the corresponding microorganism or may be introduced into the microorganism from an outside by genetic engineering technology. In this case, glycerol and acetyl-CoA may be reacted in the microorganism, but it is not limited thereto.

The acetin may include monoacetin, diacetin or triacetin, or a combination thereof.

The first O-acetyl transferase may act as a catalyst in a reaction of glycerol and acetyl-CoA to generate monoacetin, and the monoacetin may be reacted again with acetyl-CoA in the presence of the first O-acetyl transferase, thereby producing diacetin, but it is not limited thereto.

In the first O-acetyl transferase, the amino acid at a position corresponding to position 70 of the amino acid sequence of SEQ ID NO: 5 may be aspartic acid (ASP). Likewise, the amino acid at a position corresponding to position 84 of the amino acid sequence of SEQ ID NO: 5 may be asparagine (ASN); the amino acid at a position corresponding to position 114 of the amino acid sequence of SEQ ID NO: 5 may be histidine (HIS); and the amino acid at a position corresponding to position 126 of the amino acid sequence of SEQ ID NO: 5 may be glutamic acid (GLU), but it is not limited thereto.

Further, in the first O-acetyl transferase, the amino acid at a position corresponding to position 15 of the amino acid sequence of SEQ ID NO: 5 may be tyrosine (TYR) or phenylalanine (PHE). Likewise, the amino acid at a position corresponding to position 26 of the amino acid sequence of SEQ ID NO: 5 may be arginine (ARG) or glutamine (GLN); the amino acid at a position corresponding to position 30 of the amino acid sequence of SEQ ID NO: 5 may be arginine (ARG) or lysine (LYS); the amino acid at a position corresponding to position 71 of the amino acid sequence of SEQ ID NO: 5 may be tyrosine (TYR); and the amino acid at a position corresponding to position 82 of the amino acid sequence of SEQ ID NO: 5 may be phenylalanine (PHE) or tyrosine (TYR), but it is not limited thereto.

Tyrosine (TYR) or phenylalanine (PHE), which is the amino acid at the position corresponding to position 15 of the amino acid sequence of SEQ ID NO: 5 of the first O-acetyl transferase; likewise, arginine (ARG) or glutamine (GLN) which is the amino acid at the position corresponding to position 26 of the amino acid sequence of SEQ ID NO: 5; arginine (ARG) or lysine (LYS), which is the amino acid at the position corresponding to position 30 of the amino acid sequence of SEQ ID NO: 5; tyrosine (TYR), which is the amino acid at the position corresponding to position 71 of the amino acid sequence of SEQ ID NO: 5; and phenylalanine (PHE) or tyrosine (TYR), which is the amino acid at the position corresponding to position 82 of the amino acid sequence of SEQ ID NO: 5, are residues, each of which forms a substrate binding pocket and is relatively well-preserved and plays an important role in producing acetin.

Aspartic acid (ASP) which is the amino acid at the position corresponding to position 70 of the amino acid sequence of SEQ ID NO: 5 of the first O-acetyl transferase; likewise, asparagine (ASN) which is the amino acid at the position corresponding to position 84 of the amino acid sequence of SEQ ID NO: 5; and glutamic acid (GLU) which is the amino acid at the position corresponding to position 126 of the amino acid sequence of SEQ ID NO: 5, are amino acid residues, each of which stabilizes glycerol, is relatively well-preserved and plays an important role in producing acetin.

Histidine (HIS) which is the amino acid at the position corresponding to position 114 of the amino acid sequence of SEQ ID NO: 5 of the first O-acetyl transferase is a residue acting as a catalyst, is relatively well-preserved and corresponds to an amino acid residue that plays an important role in producing acetin.

Further, the amino acid sequence of the first O-acetyl transferase may have 50% or more homology to the amino acid sequence of SEQ ID NO: 5.

The maltose O-acetyl transferase may include, for example: maltose O-acetyl transferase of *Escherichia coli* (SEQ ID NO: 1); maltose O-acetyl transferase of *Staphylococcus carnosus* (SEQ ID NO: 2); maltose O-acetyl transferase of *Halalkalicoccus jeotgali* (SEQ ID NO: 3); maltose O-acetyl transferase of *Lactobacillus brevis* (SEQ ID NO: 4); maltose O-acetyl transferase of *Bacillus subtilis* (SEQ ID NO: 5); or maltose O-acetyl transferase of *Pseudomonas putida* (SEQ ID NO: 6), preferably, maltose O-acetyl transferase of *Bacillus subtilis*, but it is not limited thereto.

The amino acid sequence of maltose O-acetyl transferase of *Escherichia coli* (SEQ ID NO: 1) has 65% homology to the amino acid sequence of maltose O-acetyl transferase of *Bacillus subtilis* (SEQ ID NO: 5), while the amino acid sequence of maltose O-acetyl transferase of *Staphylococcus carnosus* (SEQ ID NO: 2) has 58% homology to the amino acid sequence of maltose O-acetyl transferase of *Bacillus subtilis* (SEQ ID NO: 5). Further, the amino acid sequence of maltose O-acetyl transferase of *Halalkalicoccus jeotgali* (SEQ ID NO: 3) has 53% homology to the amino acid sequence of maltose O-acetyl transferase of *Bacillus subtilis* (SEQ ID NO: 5), while the amino acid sequence of maltose O-acetyl transferase of *Lactobacillus brevis* (SEQ ID NO: 4) has 55% homology to the amino acid sequence of maltose O-acetyl transferase of *Bacillus subtilis* (SEQ ID NO: 5). In addition, the amino acid sequence of maltose O-acetyl transferase of *Pseudomonas putida* (SEQ ID NO: 6) has 50% homology to the amino acid sequence of maltose O-acetyl transferase of (*Bacillus subtilis* (SEQ ID NO: 5).

Further, the method for production of acetin according to the present invention may further include reacting the reaction product, that is, diacetin with acetyl-CoA in the presence of a second O-acetyl transferase.

In the second O-acetyl transferase, the amino acid at a position corresponding to position 31 of the amino acid sequence of SEQ ID NO: 7 may be cysteine (CYS) or leucine (LEU); likewise, the amino acid at a position corresponding to position 102 of the amino acid sequence of SEQ ID NO: 7 may be phenylalanine (PHE) or isoleucine (ILE); the amino acid at a position corresponding to position 143 of the amino acid sequence of SEQ ID NO: 7 may be phenylalanine (PHE) or tyrosine (TYR); the amino acid at a position corresponding to position 166 of the amino acid sequence of SEQ ID NO: 7 may be phenylalanine (PHE) or tyrosine (TYR); the amino acid at a position corresponding to position 170 of the amino acid sequence of SEQ ID NO: 7 may be valine (VAL), isoleucine (ILE) or leucine (LEU); and the amino acid at a position corresponding to position 193 of the amino acid sequence of SEQ ID NO: 7 may be histidine (HIS), but it is not limited thereto.

The second O-acetyl transferase may generate triacetin by transferring an acetyl group to diacetin, and may include, for example, chloramphenicol-O-acetyl transferase, but it is not limited thereto.

Chloramphenicol-O-acetyl transferase may consist of, for example, the amino acid sequence of SEQ ID NO: 7, but it is not limited thereto.

The chloramphenicol-O-acetyl transferase of SEQ ID NO: 7 (SEQ ID NO: 7) may be, for example, expressed in: a pSTV28 vector having a chloramphenicol-resistance antibiotic marker; a microorganism having a chloramphenicol-resistance antibiotic marker; or a microorganism, in which pSTV 28 vector is inherently included or acquired, or may be prepared synthetically, but it is not limited thereto.

When the glycerol and acetyl-CoA react in the presence of the first O-acetyl transferase and the second O-acetyl transferase, a complex of monoacetin, diacetin and triacetin may be produced, but it is not limited thereto.

The second O-acetyl transferase is chloramphenicol-O-acetyl transferase, or has a protein sequence and structure similar to the same, thereby transferring an acetyl group to diacetin and producing triacetin.

The second O-acetyl transferase may be expressed in a microorganism having a gene encoding the second O-acetyl transferase, and the gene encoding the second O-acetyl transferase in the microorganism may be inherent in the microorganism or may be introduced into the microorganism from the outside by genetic engineering technology. In this case, glycerol and acetyl-CoA may be reacted in the microorganism, but it is not limited thereto.

The second O-acetyl transferase may be derived from an organism or may be synthesized.

In the second O-acetyl transferase, any one among cysteine (CYS) or leucine (EU) which is an amino acid at a position corresponding to position 31 of the amino acid sequence of SEQ ID NO: 7; likewise, threonine (THR) or proline (PRO) which is an amino acid at a position corresponding to position 93 of the amino acid sequence of SEQ ID NO: 7; phenylalanine (PHE) or isoleucine (ILE) which is an amino acid at a position corresponding to position 102 of the amino acid sequence of SEQ ID NO: 7; phenylalanine (PHE) or tyrosine (TYR) which is an amino acid at a position corresponding to position 143 of the amino acid sequence of SEQ ID NO: 7; phenylalanine (PHE) or tyrosine (TYR) which is an amino acid at a position corresponding to position 166 of the amino acid sequence of SEQ ID NO: 7; or valine (VAL), isoleucine (ILE) or leucine (LEU) which is an amino acid at a position corresponding to position 170 of the amino acid sequence of SEQ ID NO: 7, may be a residue to form a substrate binding pocket, relatively well-preserved and corresponds to an amino acid residue that plays an important role in producing acetin.

In the second O-acetyl transferase, histidine (HIS) which is an amino acid at the position corresponding to position 193 of the amino acid sequence of SEQ ID NO: 7 is a residue that acts as a catalyst, is relatively well preserved and corresponds to an amino acid residue that plays an important role in producing acetin.

Further, the amino acid sequence of the second O-acetyl transferase may have 32% or more homology to the amino acid sequence of SEQ ID NO: 7.

Specifically, the second O-acetyl transferase may include: chloramphenicol-O-acetyl transferase of SEQ ID NO: 7; O-acetyl transferase of *Bacillus cereus* (SEQ ID NO: 8); O-acetyl transferase of *Pseudomonas aeruginosa* (SEQ ID NO: 9); or O-acetyl transferase of *Clostridium acetobutylicum* (SEQ ID NO: 10); preferably, O-acetyl transferase of *Bacillus cereus*, but it is not limited thereto.

The amino acid sequence of O-acetyl transferase of *Bacillus cereus* (SEQ ID NO: 8) has 43% or more homology to the amino acid sequence of chloramphenicol-O-acetyl transferase (SEQ ID NO: 7) while the amino acid sequence of O-acetyl transferase of *Pseudomonas aeruginosa* (SEQ ID NO: 9) has 62% homology to the amino acid sequence of chloramphenicol-O-acetyl transferase (SEQ ID NO: 7). Further, the amino acid sequence of O-acetyl transferase of *Clostridium acetobutylicum* (SEQ ID NO: 10) has 32% homology to the amino acid sequence of chloramphenicol-O-acetyl transferase (SEQ ID NO: 7).

Further, the method for production of acetin according to the present invention may further include sequentially reacting glucose with glycerol-3-phosphate dehydrogenase and glycerol 3-phosphatase (i.e., DL-glycerol-3-phosphatase), so as to prepare the above glycerol.

The glycerol described above may be obtained through biosynthesis to react glucose with an enzyme and, for specific example, glycerol may be obtained by sequentially reacting glucose with glycerol-3-phosphate dehydrogenase (GPD1) and DL-glycerol-3-phosphatase (GPP2), but it is not limited thereto.

In this regard, glycerol-3-phosphate dehydrogenase and DL-glycerol-3-phosphatase may be chemically synthesized.

Further, glycerol-3-phosphate dehydrogenase and DL-glycerol-3-phosphatase may be expressed in a microorganism having genes encoding glycerol-3-phosphate dehydrogenase and DL-glycerol-3-phosphatase. Herein, the genes encoding glycerol-3-phosphate dehydrogenase and DL-glycerol-3-phosphatase may be inherent in the corresponding microorganism. Alternatively, the genes encoding glycerol-3-phosphate dehydrogenase and DL-glycerol-3-phosphatase may be introduced into the microorganism from the outside by genetic engineering technology. In this case, glycerol may be obtained from glucose in the microorganism, but it is not limited thereto.

The glycerol-3-phosphate dehydrogenase may have different amino acid sequences depending on type of microorganism, and may be any dehydrogenase as long as it can convert glycerone phosphate (DHAP), which is an intermediate metabolite of a glycolysis pathway in the corresponding microorganism, into glycerol-3-phosphate (G3P) For example, in the case of *Saccharomyces cerevisiae*, glycerol-3-phosphate dehydrogenase (GPD1) of *Saccharomyces cerevisiae* of SEQ ID NO: 14 may be used, but it is not limited thereto.

The DL-glycerol-3-phosphatase described above may have a different amino acid sequence depending on the type of microorganism, and may be any phosphatase as long as it can convert glycerol-3-phosphate (G3P), which is an intermediate metabolite of a glycolysis pathway in the corresponding microorganism, into glycerol. For example, in the case of *Saccharomyces cerevisiae*, DL-glycerol-3-phosphatase, GPP2) of *Saccharomyces cerevisiae* of SEQ ID NO: 15 may be used, but it is not limited thereto.

The glucose may form glycerone phosphate (DHAP), which is an intermediate metabolite, through a glycolysis pathway (Embden-Meyerhof pathway), and the glycerone phosphate may react with glycerol-3-phosphate dehydrogenase so as to be converted into glycerol-3-phosphate. Further, the glycerol-3-phosphate (G3P) may be reacted with DL-glycerol-3-phosphatase, thereby preparing glycerol, but it is not limited thereto.

Further, the present invention relates to a method for production of acetin, which includes culturing a microorganism that expresses a gene encoding a first O-acetyl transferase in a medium containing glycerol.

In the first O-acetyl transferase, the amino acid at a position corresponding to position 70 of the amino acid sequence of SEQ ID NO: 5 may be aspartic acid (ASP); likewise, the amino acid at a position corresponding to position 84 of the amino acid sequence of SEQ ID NO: 5 may be asparagine (ASN); the amino acid at a position corresponding to position 114 of the amino acid sequence of SEQ ID NO: 5 may be histidine (HIS); and the amino acid at a position corresponding to position 126 of the amino acid sequence of SEQ ID NO: 5 may be glutamic acid (GLU), but it is not limited thereto.

Further, in the first O-acetyl transferase, the amino acid at a position corresponding to position 15 of the amino acid sequence of SEQ ID NO: 5 may be tyrosine (TYR) or phenylalanine (PHE); likewise, the amino acid at a position corresponding to position 26 of the amino acid sequence of SEQ ID NO: 5 may be arginine (ARG) or glutamine (GLN); the amino acid at a position corresponding to position 30 of the amino acid sequence of SEQ ID NO: 5 may be arginine (ARG) or lysine (LYS); the amino acid at a position corresponding to position 71 of the amino acid sequence of SEQ ID NO: 5 may be tyrosine (TYR); and the amino acid at a position corresponding to position 82 of the amino acid sequence of SEQ ID NO: 5 may be phenylalanine (PHE) or tyrosine (TYR), but it is not limited thereto.

Further, the amino acid sequence of the first O-acetyl transferase may have 50% or more homology to the amino acid sequence of SEQ ID NO: 5.

The gene encoding the first O-acetyl transferase may be, for example, a gene encoding maltose O-acetyl transferase, and the gene encoding the maltose O-acetyl transferase may include, for example, a gene encoding maltose O-acetyl transferase of *Escherichia coli* (maa, SEQ ID NO: 16), a gene encoding maltose O-acetyl transferase of *Staphylococcus carnosus* (Sc-maa, SEQ ID NO: 17), a gene encoding maltose O-acetyl transferase of *Halalkalicoccus jeotgali* (Hj-maa, SEQ ID NO: 18), a gene encoding maltose O-acetyl transferase of *Lactobacillus brevis* (Lb-maa, SEQ ID NO: 19), a gene encoding maltose O-acetyl transferase of *Bacillus subtilis* (Bs-maa, SEQ ID NO: 20), or a gene encoding maltose O-acetyl transferase of *Pseudomonas putida* (Pp-maa, SEQ ID NO: 21), preferably a gene encoding maltose O-acetyl transferase of *Bacillus subtilis*, but it is not limited thereto.

The microorganism may be cultured in a medium to express a first O-acetyl transferase, and the first O-acetyl transferase may catalyze a reaction of glycerol and acetyl-CoA to produce monoacetin. Further, the first O-acetyl transferase may catalyze again a reaction of monoacetin and acetyl-CoA, so as to produce diacetin.

The microorganism may be used without limitation thereof as long as it is a microorganism expressing the first O-acetyl transferase, and may be, for example, a prokaryotic cell, a eukaryotic cell, or an isolated animal cell that can be cultured in a liquid medium. The microorganism may include, for example, bacteria, fungi or a combination thereof. The bacteria may include, for example, gram-positive bacteria, gram-negative bacteria or a combination thereof. The gram-negative bacteria may be *Escherichia* genus. The gram-positive bacteria may be *Bacillus* genus, *Corynebacterium* genus, lactic acid bacteria, etc., or a combination thereof. The fungus may be *Saccharomyces cerevisiae, Kluberomyces*, etc., or a combination thereof. The microorganism may be specifically *E. coli*, more specifically, DH5α, DH5α (DE3), AceCo, BW25113, W3110 or MG1655. The microorganism is preferably DH5α (DE3), BW25113, W3110 or MG1655 in terms of productivity among *E. coli*, and more preferably MG1655, but it is not limited thereto.

The microorganism may be a microorganism that naturally possesses a gene encoding the first O-acetyl transferase, and a microorganism that acquires and retains the gene by biotechnical techniques such as transformation and transduction, etc., but it is not limited thereto.

The transformation may be implemented by introducing a recombinant plasmid into the microorganism, and the recombinant plasmid may be a gene encoding the first O-acetyl transferase in a vector, but it is not limited thereto.

The vector may include, for example, pTrc99A (SEQ ID NO: 78), pET28a (SEQ ID NO: 79) or pSTV28 (SEQ ID NO: 77), and preferably pSTV28, but it is not limited thereto.

When inserting the gene, the vector and the gene may be cut by a restriction enzyme and linked with a ligase, and then cloned, but it is not limited thereto.

The medium is a substance designed to maintain a nutritional state similar to the natural environment in which microorganisms generally survive and reproduce for purposes of proliferation or cultivation of the microorganisms. Specifically, the medium is a liquid and solid substance prepared by adding all the nutrients necessary to grow, and includes acetyl-CoA as well as glycerol, but it is not limited thereto.

Further, the microorganism of the present invention may further express a gene encoding the second O-acetyl transferase that transfers an acetyl group to diacetin.

In the second O-acetyl transferase, the amino acid at a position corresponding to position 31 of the amino acid sequence of SEQ ID NO: 7 may be cysteine (CYS) or leucine (LEU); likewise, the amino acid at a position corresponding to position 102 of the amino acid sequence of SEQ ID NO: 7 may be phenylalanine (PHE) or isoleucine (ILE); the amino acid at a position corresponding to position 143 of the amino acid sequence of SEQ ID NO: 7 may be phenylalanine (PHE) or tyrosine (TYR); the amino acid at a position corresponding to position 166 of the amino acid sequence of SEQ ID NO: 7 may be phenylalanine (PHE) or tyrosine (TYR); the amino acid at a position corresponding to position 170 of the amino acid sequence of SEQ ID NO: 7 may be valine (VAL), isoleucine (ILE) or leucine (LEU); and the amino acid at a position corresponding to position 193 of the amino acid sequence of SEQ ID NO: 7 may be histidine (HIS), but it is not limited thereto.

The microorganism is cultured in a medium, and may express not only the first O-acetyl transferase, but also chloramphenicol-O-acetyl transferase or the second O-acetyl transferase.

The gene (cat, SEQ ID NO: 24) encoding the chloramphenicol-O-acetyl transferase (SEQ ID NO: 7) may be present in a vector having a chloramphenicol-resistance antibiotic marker, wherein the vector may be, for example, a pSTV28 vector, and if the vector is a microorganism, the vector can be introduced without limitation thereof to express the chloramphenicol-O-acetyl transferase from the corresponding microorganism. For instance, the vector may be introduced into *E. coli* to express the chloramphenicol-O-acetyl transferase from *E. coli*, but it is not limited thereto.

The gene encoding the second O-acetyl transferase may include, for example: a gene encoding chloramphenicol-O-acetyl transferase (cat, SEQ ID NO: 24); a gene encoding O-acetyl transferase of *Bacillus cereus* (Bc-Oat, SEQ ID NO: 25); a gene encoding O-acetyl transferase of *Pseudomonas aeruginosa* (Pa-Oat, SEQ ID NO: 26); a gene for encoding O-acetyl transferase of *Clostridium acetobutylicum* (Ca-Oat, SEQ ID NO: 27); and preferably a gene encoding O-acetyl transferase of *Bacillus cereus*, but it is not limited thereto.

Further, the amino acid sequence of the second O-acetyl transferase may have 32% or more homology to the amino acid sequence of SEQ ID NO: 7.

Further, the microorganism of the present invention may include a gene encoding acetylesterase, which is attenuated or deleted.

Acetin as an ester compound may be degraded into glycerol and acetate by ester-binding degradation enzymes (esterases), and an example of the esterases degrading acetin may be acetylesterase.

In the case of a microorganism in which the gene encoding acetylesterase is attenuated or deleted, the acetylesterase is not expressed whereby the production amount of acetin may be increased.

The acetylesterase may have a different sequence depending on the type of microorganism, and the gene encoding the same may also have a different sequence. Therefore, the gene (aes) encoding the acetyl esterase in the corresponding microorganism may be attenuated or deleted. For example, in the case of *E. coli*, the gene of SEQ ID NO: 30 encoding the acetyl esterase of SEQ ID NO: 13 may be attenuated or deleted, but it is not limited thereto.

Further, the microorganism used herein may be any microorganism without limitation thereof as long as it expresses the first O-acetyl transferase. Specifically, the microorganism may be any microorganism within the above-described range, but it is not limited thereto.

Further, when an initial strain concentration during main culture of the microorganism of the present invention ranges from 0.05 to 0.15 at $OD_{600\ nm}$, a concentration of glycerol contained in the medium may range from 3% (v/v) to 13% (v/v). Preferably, when the initial strain concentration ranges from 0.08 to 0.12 at $OD_{600\ nm}$, the concentration of glycerol may range from 5% (v/v) to 11% (v/v), but it is not limited thereto.

When the microorganism is cultured at the above strain concentration in the medium having the above glycerol concentration, a large amount of acetin may be generated.

When the glycerol concentration is more than 13% (v/v), both of strain proliferation and acetin production may be reduced due to an excessive increase in osmotic pressure. On the other hand, when the glycerol concentration is less than 3% (v/v), a production amount of acetin may be reduced due to a low concentration of the substrate.

Further, the microorganism of the present invention may further express genes encoding glycerol-3-phosphate dehydrogenase and DL-glycerol-3-phosphatase, and the medium may include glucose, but it is not limited thereto.

As described above, the microorganism expresses glycerol-3-phosphate dehydrogenase and DL-glycerol-3-phosphatase, wherein glucose is converted into glycerone phosphate through a glycolysis pathway and then converted into glycerol by the enzymes.

The gene (Gpd1) encoding glycerol-3-phosphate dehydrogenase may have a different nucleotide sequence depending on the type of microorganism, and may be any gene as long as it can convert glycerone phosphate (DHAP) which is an intermediate metabolite of a glycolysis pathway in the corresponding microorganism into glycerol-3-phosphate (G3P). For example, in the case of *Saccharomyces cerevisiae*, a gene encoding glycerol-3-phosphate dehydrogenase of *Saccharomyces cerevisiae* (Sc-gpd1) of SEQ ID NO: 31 may be used, but it is not limited thereto.

The gene (Gpp2) encoding DL-glycerol-3-phosphatase may have a different nucleotide sequence depending on the type of microorganism, and may be any gene as long as it can convert glycerol 3-phosphate (G3P), which is an intermediate metabolite of a glycolysis pathway in the corresponding microorganism, into glycerol-3-phosphate, into glycerol. For example, in the case of *Saccharomyces cerevisiae*, a gene encoding DL-glycerol-3-phosphatase of *Saccharomyces cerevisiae* (Sc-gpp2) of SEQ ID NO: 32 may be used, but it is not limited thereto.

The glycerol may be converted into an acetin complex by the above-described first O-acetyl transferase and chloramphenicol-O-acetyl transferase or the second O-acetyl transferase.

Further, the present invention relates to a composition for production of acetin, which includes a microorganism to express a gene encoding the first O-acetyl transferase.

When the composition is in contact with glycerol, acetin may be prepared in the above-described range by the above-described method.

In the first O-acetyl transferase, the amino acid at a position corresponding to position 70 of the amino acid sequence of SEQ ID NO: 5 may be aspartic acid (ASP); likewise, the amino acid at a position corresponding to position 84 of the amino acid sequence of SEQ ID NO: 5 may be asparagine (ASN); the amino acid at a position corresponding to position 114 of the amino acid sequence of SEQ ID NO: 5 may be histidine (HIS); and the amino acid at a position corresponding to position 126 of the amino acid sequence of SEQ ID NO: 5 may be glutamic acid (GLU), but it is not limited thereto.

Further, in the first O-acetyl transferase, the amino acid at a position corresponding to position 15 of the amino acid sequence of SEQ ID NO: 5 may be tyrosine (TYR) or phenylalanine (PHE); likewise, the amino acid at a position corresponding to position 26 of the amino acid sequence of SEQ ID NO: 5 may be arginine (ARG) or glutamine (GLN); the amino acid at a position corresponding to position 30 of the amino acid sequence of SEQ ID NO: 5 may be arginine (ARG) or lysine (LYS); the amino acid at a position corresponding to position 71 of the amino acid sequence of SEQ ID NO: 5 may be tyrosine (TYR); the amino acid at a position corresponding to position 82 of the amino acid sequence of SEQ ID NO: 5 may be phenylalanine (PHE) or tyrosine (TYR), but it is not limited thereto.

Further, the amino acid sequence of the first O-acetyl transferase may have 50% or more homology to the amino acid sequence of SEQ ID NO: 5.

The first O-acetyl transferase may be maltose O-acetyl transferase, more specifically, may include maltose O-acetyl transferase of *Escherichia coli, Staphylococcus carnosus, Halalkalicoccus jeotgali, Lactobacillus brevis, Bacillus subtilis* or *Pseudomonas putida*, and preferably the maltose O-acetyl transferase of *Bacillus subtilis*, but it is not limited thereto.

The gene encoding the first O-acetyl transferase may be, for example, a gene encoding maltose O-acetyl transferase, and the gene encoding maltose O-acetyl transferase may include, for example: a gene encoding maltose O-acetyl transferase of *Escherichia coli* (maa, SEQ ID NO: 16); a gene encoding maltose O-acetyl transferase of *Staphylococcus carnosus* (Sc-maa, SEQ ID NO: 17); a gene encoding maltose O-acetyl transferase of *Halalkalicoccus jeotgali* (Hj-maa, SEQ ID NO: 18); a gene encoding maltose O-acetyl transferase of *Lactobacillus brevis* (Lb-maa, SEQ ID NO: 19); a gene encoding maltose O-acetyl transferase of *Bacillus subtilis* (Bs-maa, SEQ ID NO: 20); or a gene encoding maltose O-acetyl transferase of *Pseudomonas putida* (Pp-maa, SEQ ID NO: 21), and preferably the gene encoding maltose O-acetyl transferase of *Bacillus subtilis*, but it is not limited thereto.

Further, the microorganism may further express a gene encoding the second O-acetyl transferase that transfers an acetyl group to diacetin.

In the second O-acetyl transferase, the amino acid at a position corresponding to position 31 of the amino acid sequence of SEQ ID NO: 7 may be cysteine (CYS) or leucine (LEU); likewise, the amino acid at a position corresponding to position 102 of the amino acid sequence of SEQ ID NO: 7 may be phenylalanine (PHE) or isoleucine (ILE); the amino acid at a position corresponding to position 143 of the amino acid sequence of SEQ ID NO: 7 may be phenylalanine (PHE) or tyrosine (TYR); the amino acid at a position corresponding to position 166 of the amino acid sequence of SEQ ID NO: 7 may be phenylalanine (PHE) or tyrosine (TYR); the amino acid at a position corresponding to position 170 of the amino acid sequence of SEQ ID NO: 7 may be valine (VAL), isoleucine (ILE) or leucine (LEU); and the amino acid at a position corresponding to position 193 of the amino acid sequence of SEQ ID NO: 7 may be histidine (HIS), but it is not limited thereto.

The gene encoding chloramphenicol-O-acetyl transferase may be present in a vector having a chloramphenicol-resistance antibiotic marker, for example, the vector may be pSTV28 vector, but it is not limited thereto.

The gene encoding the second O-acetyl transferase may include, for example, genes encoding O-acetyl transferases of *Bacillus cereus*, *Pseudomonas aeruginosa* or *Clostridium acetobutylicum*, and preferably, the gene encoding O-acetyl transferase of *Bacillus cereus*, but it is not limited thereto.

Further, the amino acid sequence of the second O-acetyl transferase may have 32% or more homology to the amino acid sequence of SEQ ID NO: 7.

Further, the microorganism may include a gene encoding acetylesterase, which is attenuated or deleted.

The ester compound, that is, acetin may be degraded into glycerol and acetate by ester-binding degradation enzymes (esterases), wherein the ester-binding degradation enzyme to degrade acetin may be, for example, acetylesterase.

In the case of a microorganism in which the gene encoding acetylesterase (aes) is attenuated or deleted, the acetylesterase is not expressed, thereby increasing a production amount of acetin.

The acetylesterase may have a different sequence depending on the type of microorganism, and a gene encoding the same may also have a different sequence. Therefore, the gene encoding acetylesterase in the microorganism may be attenuated or deleted. For example, in the case of *E. coli*, the gene of SEQ ID NO: 30 encoding the acetylesterase of SEQ ID NO: 13 may be attenuated or deleted, but it is not limited thereto.

Further, the microorganism is the same as described above, but may be specifically *E. coli*, more specifically, DH5α, DH5α (DE3), AceCo, BW25113, W3110 or MG1655, and preferably MG1655, but it is not limited thereto.

Further, the microorganism may further express genes encoding glycerol-3-phosphate dehydrogenase and DL-glycerol-3-phosphatase.

As described above, the microorganism may express glycerol-3-phosphate dehydrogenase and DL-glycerol-3-phosphatase, wherein glucose can be converted into glycerol through a glycolysis pathway using enzymes described above.

The gene (Gpd1) encoding glycerol-3-phosphate dehydrogenase may have a different nucleotide sequence depending on the type of microorganism, and may be any dehydrogenase as long as it can convert glycerone phosphate (DHAP), which is an intermediate metabolite of a glycolysis pathway in the corresponding microorganism, into glycerol-3-phosphate (G3P). For example, in the case of *Saccharomyces cerevisiae*, the gene encoding glycerol-3-phosphate dehydrogenase of *Saccharomyces cerevisiae* (Sc-gpd1) of SEQ ID NO: 31 may be used, but it is not limited thereto.

The gene (Gpp2) encoding DL-glycerol-3-phosphatase may have a different nucleotide sequence depending on the type of microorganism, and may be any phosphatase as long as it can convert glycerol-3-phosphate (G3P), which is an intermediate metabolite of a glycolysis pathway in the corresponding microorganism, into glycerol. For example, in the case of *Saccharomyces cerevisiae*, the gene encoding DL-glycerol-3-phosphatase of *Saccharomyces cerevisiae* (Sc-gpp2) of SEQ ID NO: 32 may be used, but it is not limited thereto.

The glycerol described above may be converted into an acetin complex by the above-described O-acetyl transferase and chloramphenicol-O-acetyl transferase, and the like.

Hereinafter, the following examples will be described in detail to specifically stipulate the present invention. The plasmids and strains used in the following examples are summarized in Table 1 and PCR primers are listed in Table 2.

TABLE 1

| Names | Descriptions | Sources |
| --- | --- | --- |
| Plasmids | | |
| pSTV28 | $P_{lac}$ expression vector, pACYC184 origin, lacZα, $Cm^r$ | Takara Co., Ltd |
| pTrc99A | Ptrc expression vector, pBR322 origin, lacIq, $Amp^r$ | Amersham Bioscience |
| pET28a (+) | $P_{T7}$ expression vector, pBR322 origin, lacI, and $Kan^r$ | Novagen |
| pMD1 | pTrc99A vector containing lacA from *E. coli* | — |
| pMD2 | pTrc99A vector containing cysE from *E. coli* | — |
| pMD3 | pTrc99A vector containing yjgM from *E. coli* | — |
| pMD4 | pTrc99A vector containing yjaB from *E. coli* | — |
| pMD5 | pTrc99A vector containing yiiD from *E. coli* | — |
| pMD6 | pTrc99A vector containing wecH from *E. coli* | — |
| pMD7 | pTrc99A vector containing nhoA from *E. coli* | — |
| pMD8 | pTrc99A vector containing maa from *E. coli* | — |
| pMD9 | pTrc99A vector containing maa from *S. carnosus* | — |
| pMD10 | pTrc99A vector containing maa from *H. jeotgali* | — |

TABLE 1-continued

| Names | Descriptions | Sources |
|---|---|---|
| pMD11 | pTrc99A vector containing maa from L. brevis | — |
| pMD12 | pTrc99A vector containing maa from P. putida | — |
| pMD13 | pTrc99A vector containing maa from B. subtilis | — |
| pMD14 | pET28a vector containing maa from B. subtilis | — |
| pT-CAT | pTrc99A vector containing cat from pSTV28 | — |
| pMDT1 | pSTV28 vector containing maa from B. subtilis | — |
| pMDT2 | pTrc99A vector containing cat from pSTV28 and maa from B. subtilis | — |
| pMDT3 | pTrc99A vector containing oat from B. cereus and maa from B. subtilis | — |
| pMDT4 | pTrc99A vector containing oat from P. aeruginosa and maa from B. subtilis | — |
| pMDT5 | pTrc99A vector containing oat from C. acetobutylicum and maa from B. subtilis | — |
| pMDT6 | pTrc99A vector containing oat from M. abscessus and maa from B. subtilis | — |
| pMDT7 | pTrc99A vector containing oat from L. brevis and maa from B. subtilis | — |
| pMDT8 | pMDT2 containing gpd1 and gpp2 from S. cerevisiae | — |
| Strains | | |
| MG1655 | E. coli K-12; F⁻ lambda⁻, ilvG⁻, rfb-50, rph-1 | ATCC700926 |
| DH5α | E. coli K-12; F⁻, Φ80lacZΔM15, Δ(lacZYA-argF)U169, deoR, recA1, endA1, hsdR17(rK⁻, mK⁺) phoA, supE44, λ⁻, thi-1 | ATCC98040 |
| BW25113 | Δ(araD-araB)567, ΔlacZ4787(::rrnB-3), lambda⁻, rph-1, Δ(rhaD-rhaB)568, hsdR514 | NBRP, NIG |
| AceCo | MG1655 ΔackA-pta, poxB, ldhA, dld, adhE, pps, atoDA | Ref. 1 |
| W3110 | E. coli K-12; F⁻, λ⁻ IN (rrnD-rrnE)1 | ATCC27325 |
| DH5α (DE3) | E. coli K-12; F⁻, Φ801acZΔM15, Δ(lacZYA-argF)U169, deoR, recA1, endA1, hsdR17(rK⁻, mK⁺) phoA, supE44, λ⁻, thi-1, λ(DE3) | — |
| JW0465 | BW25113 Δaes | NBRP, NIG |
| DH-MD0 | E. coli DH5α harboring pTrc99A | — |
| DH-MD1 | E. coli DH5α harboring pMD1 | — |
| DH-MD2 | E. coli DH5α harboring pMD2 | — |
| DH-MD3 | E. coli DH5α harboring pMD3 | — |
| DH-MD4 | E. coli DH5α harboring pMD4 | — |
| DH-MD5 | E. coli DH5α harboring pMD5 | — |
| DH-MD6 | E. coli DH5α harboring pMD6 | — |
| DH-MD7 | E. coli DH5α harboring pMD7 | — |
| DH-MD8 | E. coli DH5α harboring pMD8 | — |
| DH-MD9 | E. coli DH5α harboring pMD9 | — |
| DH-MD10 | E. coli DH5α harboring pMD10 | — |
| DH-MD11 | E. coli DH5α harboring pMD11 | — |
| DH-MD12 | E. coli DH5α harboring pMD12 | — |
| DH-MD13 | E. coli DH5α harboring pMD13 | — |
| DH-MD14 | E. coli DH5α(DE3) harboring pMD14 | — |
| DH-MDT1 | E. coli DH5α harboring pMDT1 | — |
| DH-EMPT | E. coli DH5α harboring pTrc99A | — |
| DH-CAT | E. coli DH5α harboring pT-CAT | — |
| DH-MDT2 | E. coli DH5α harboring pMDT2 | — |
| DH-MDT3 | E. coli DH5α harboring pMDT3 | — |
| DH-MDT4 | E. coli DH5α harboring pMDT4 | — |
| DH-MDT5 | E. coli DH5α harboring pMDT5 | — |
| DH-MDT6 | E. coli DH5α harboring pMDT6 | — |
| DH-MDT7 | E. coli DH5α harboring pMDT7 | — |
| AC-MDT2 | E. coli AceCo harboring pMDT2 | — |
| BW-MDT2 | E. coli BW25113 harboring pMDT2 | — |
| W3-MDT2 | E. coli W3110 harboring pMDT2 | — |
| MG-MDT2 | E. coli MG1655 harboring pMDT2 | — |
| BW-Empty | E. coli BW25113 harboring pTrc99A | — |
| BW-Aes | E. coli BW25113 harboring pT-Aes | — |
| BW-MDT2 (Δaes) | E. coli JW0465 harboring pMDT2 | — |
| DH-MDT8 | E. coli DH5α harboring pMDT8 | — |

Ref. 1. Kim, J.-H. et al. Isoprene production by *Escherichia coli* through the exogenous mevalonate pathway with reduced formation of fermentation byproducts. *Microbial Cell Factories* 15, 214 (2016).

TABLE 2

| Primers[a,b,c] | Descriptions (5'→3') | SEQ ID NO: |
|---|---|---|
| Ec-lacA-F | CTGGATCCAGGAGGTAATAAAATGGAACATGCCAATGACCG | 33 |
| Ec-lacA-R | GTTTCTAGATTAAACTGACGATTCAACTTTATAATC | 34 |
| Ec-cysE-F | CTGGATCCAGGAGGTAATAAAATGTCGTGTGAAGAACTGGAAATTG | 35 |
| Ec-cysE-R | GTTTCTAGATTAGATCCCATCCCCATACTC | 36 |
| Ec-yjgm-F | CTGGATCCAGGAGGTAATAAAATGAATAACATTGCGCCGC | 37 |
| Ec-yjgM-R | GTTTCTAGATTAGAGTTCGCGCAACATCC | 38 |
| Ec-yjaB-F | CTGGATCCAGGAGGTAATAAAATGGTTATTAGTATTCGCCGCTC | 39 |
| Ec-yjaB-R | GTTTCTAGATTACGCCCCACATACGC | 40 |
| Ec-yiiD-F | CTGGATCCAGGAGGTAATAAAATGAGCCAGCTTCCAGGG | 41 |
| Ec-nhoA-F | CTGGATCCAGGAGGTAATAAAATGACGCCCATTCTGAATCAC | 42 |
| Ec-nhoA-R | GTTTCTAGATTATTTTCCCGCCTCCGGG | 43 |
| Ec-wecH-F | CTGGATCCAGGAGGTAATAAAATGCAGCCCAAAATTTACTGG | 44 |
| Ec-WecH-R | GTTTCTAGATTAACTCACTAATCTGTTTCTGTCG | 45 |
| Ec-yiiD-R | GTTTCTAGATTACTCTTCTTCGTTCCCGC | 46 |
| Ec-maa-F | CTGGATCCAGGAGGTAATAAAATGAGCACAGAAAAAGAAAAGATG | 47 |
| Ec-maa-R | GTTTCTAGATTACAATTTTTAATTATTCTGGCTG | 48 |
| Sc-maa-F | CTGGATCCAGGAGGTAATAAAATGACCACCGAGAAGGAAAAATG | 49 |
| Sc-maa-R | GTTTCTAGATTAATCCAGCGGCACTTCAC | 50 |
| Hj-maa-F | CTGGATCCAGGAGGTAATAAAATGACCAGCGAGAAGGAACG | 51 |
| Hj-maa-R | GTTTCTAGATTAATCAACGTCCTTCAGCACA | 52 |
| Lb-maa-F | CTGGATCCAGGAGGTAATAAAATGGACAAGAGCGAGAAGG | 53 |
| Lb-maa-R | GTTTCTAGATTATTTCAGCGGCTTAATCAC | 54 |
| Pp-maa-F | CTGGATCCAGGAGGTAATAAAATGAGCCTGAGCGAGAAGCAC | 55 |
| Pp-maa-R | GTTTCTAGATTATTGACCCTGATCCGGCTG | 56 |
| Bs-maa-F | CTGGATCCAGGAGGTAATAAAATGCTGCGTACCGAGAAGG | 57 |
| Bs-maa-R | GTTTCTAGATTACAGTTGTTTCAGAATACGCGC | 58 |
| Cat-F | CTAGGAGCTCAGGAGAAATATAATGGAGAAAAAAATCACTGGATATAC | 60 |
| Cat-R | CTGGATCCTTACGCCCCGCCCTGCC | 61 |
| Trc-Bs.maa-F | AGATCTGAGTCGACAGTATCGGCGGG | 62 |
| Trc-Bs.maa-R | TATATTTCTCCTGAGGATCCCCGGGTACCG | 63 |
| Bc-Oat-F | CTCGGTACCCGGGGATCCTCAGGAGAAATATAATGGACTTCCACCAGATC | 64 |

TABLE 2-continued

| Primers[a,b,c] | Descriptions (5'→3') | SEQ ID NO: |
|---|---|---|
| Bc-Oat-R | CCCGCCGATACTGTCGACAGATCTTACAGCCATTCCTCAAAG | 65 |
| Ca-Oat-F | CTCGGTACCCGGGGATCCTC*AGGAGAAATATAAT*GAACAGCAACTTCCAC | 66 |
| Ca-Oat-R | CCCGCCGATACTGTCGACAGATCTTAACGAATCCACTCTTTC | 67 |
| Lb-Oat-F | CTCGGTACCCGGGGATCCTC*AGGAGAAATATAAT*GACCGAGCTGAACACCC | 68 |
| Lb-Oat-R | CCCGCCGATACTGTCGACAGATCTTACGCGGTCAGCCACAG | 69 |
| Ma-Oat-F | CTCGGTACCCGGGGATCCTC*AGGAGAAATATAAT*GCCGGCGGAGCACGCG | 70 |
| Ma-Oat-R | CCCGCCGATACTGTCGACAGATCTTAATCACGAACCCAATCCGGGTCCG | 71 |
| Pa-Oat-F | CTCGGTACCCGGGGATCCTC*AGGAGAAATATAAT*GAGCTACACCCGTGTTG | 72 |
| Pa-Oat-R | CCCGCCGATACTGTCGACAGATCTTAGCCACCCGCTTCATC | 73 |
| Ec-aes-F | CTGGATCC*GTCACCCAACCCTTT*ATGAAGCCGGAAAACAAACTACC | 74 |
| Ec-aes-R | TATCGTCGACTTAAAGCTGAGCGGTAAAGAACTG | 75 |
| Sc-gpd1-F | GCGGATCC*AGGAGGTAATAAA*ATGTCTGCTGCTGCTGATAGATTAAAC | 76 |
| Sc-gpd1-R | AATGCTGCAGTTAATCTTCATGTAGATCTAATTCTTCAATC | 59 |
| Sc-gpp2-F | TGCTGCAGA*GGAGGTAATTTA*TATGGGATTGACTACTAAACCTCTATC | 22 |
| Sc-gpp2-R | CCCAAGCTTACCATTTCAACAGATCGTCC | 23 |

[a]Restriction enzyme sites are underlined.
[b]RBS sequences are italic.
[c]The overlapping sequences are bolded.

Example

1. Production of Monoacetin and Diacetin Using E. coli-Derived O-Acetyl Transferase Enzymes In order to produce monoacetin and diacetin, eight (8) O-acetyl transferase candidate genes in E. coli capable of transferring an acetyl group to glycerol were selected, and each gene was cloned into a pTrc99A expression vector (SEQ ID NO: 78) to construct plasmids pMD1 to pMD8. The candidate genes were obtained through PCR amplification of: galactoside O-acetyl transferase; maltose O-acetyl transferase (SEQ ID NO: 1); serine acetyl transferase; 0-acetyl transferase WecH; and lacA (SEQ 1D NO: 80), maa (SEQ ID NO: 16), cysSE (SEQ ID NO: 81), wecH (SEQ ID NO: 82), and nhoA (SEQ ID NO: 83), which encode arylamine N-acetyltransferase, respectively; and three (3) O-acetyl transferase putative genes such as yjgm (SEQ ID NO: 84), yjaB (SEQ ID NO: 55) and yiiD (SEQ ID NO: 86) using chromosomes of E. coli MG1655 as a template. In this case, PCR primers used herein were Ec-lacA-F (SEQ ID NO: 33)/Ec-lacA-R (SEQ ID NO: 34), Ec-maa-F (SEQ ID NO: 47)/Ec-maa-R (SEQ ID NO: 48), Ec-cysE-F (SEQ ID NO: 35)/Ec-cysE-R (SEQ ID NO: 36), Ec-wecH-F (SEQ ID NO: 44)/Ec-wecH-R (SEQ ID NO: 45), Ec-nhoA-F (SEQ ID NO: 42)/Ec-nhoA-R (SEQ ID NO: 43), Ec-yjgam-F (SEQ ID NO: 37)/Ec-yjgM-R (SEQ ID NO: 38), Ec-yjaB-F (SEQ ID NO: 39)/Ec-yjaB-R (SEQ ID NO: 40), and Ec-yiiD-F (SEQ ID NO: 41)/Ec-yiiD-R (SEQ ID NO: 46). The PCR reaction product was cloned into pTrc99A vector using BamHI and XbaI. Using the constructed plasmids pDM1 to pDM8 in this way, E. coli DH5α was transformed, thereby forming recombinant strains DH-MD1 to DH-MD8 and using the same to analyze the production of monoacetin and diacetin (FIG. 3).

Seed culture was performed by shake culture for about 12 hours at 37° C. using LB complex medium (containing 10 g tryptone, 5 g yeast extract and 10 g sodium chloride per liter). Main culture was performed by adding 5 g/L of yeast extract and 2% (v/v) glycerol to M9 minimal medium (containing $Na_2HPO_4.7H_2O$, 12.8 g/L; $KH_2PO_4$, 3 g/L; NaCl, 0.5 g/L; $NH_4Cl$, 1 g/L; $MgSO_4$, 1 mM $CaCl_2$, 100 mM), and then, incubating the mixture at 37 CC and a shaking speed of 250 rpm for 48 hours. Depending on the antibiotic marker of the plasmid introduced into the recombinant strain, 100 mg/L ampicillin, 50 mag/chloramphenicol or 50 mg/L kanamycin antibiotic was added. An initial strain concentration of the culture solution was 0.1 at $OD_{600\ nm}$, and in order to express the genes introduced into the plasmid, 0.5 mM isopropyl β-D-1-thiogalactopyranoside (IPTG) was added at the beginning of the culture.

Figure 5B:
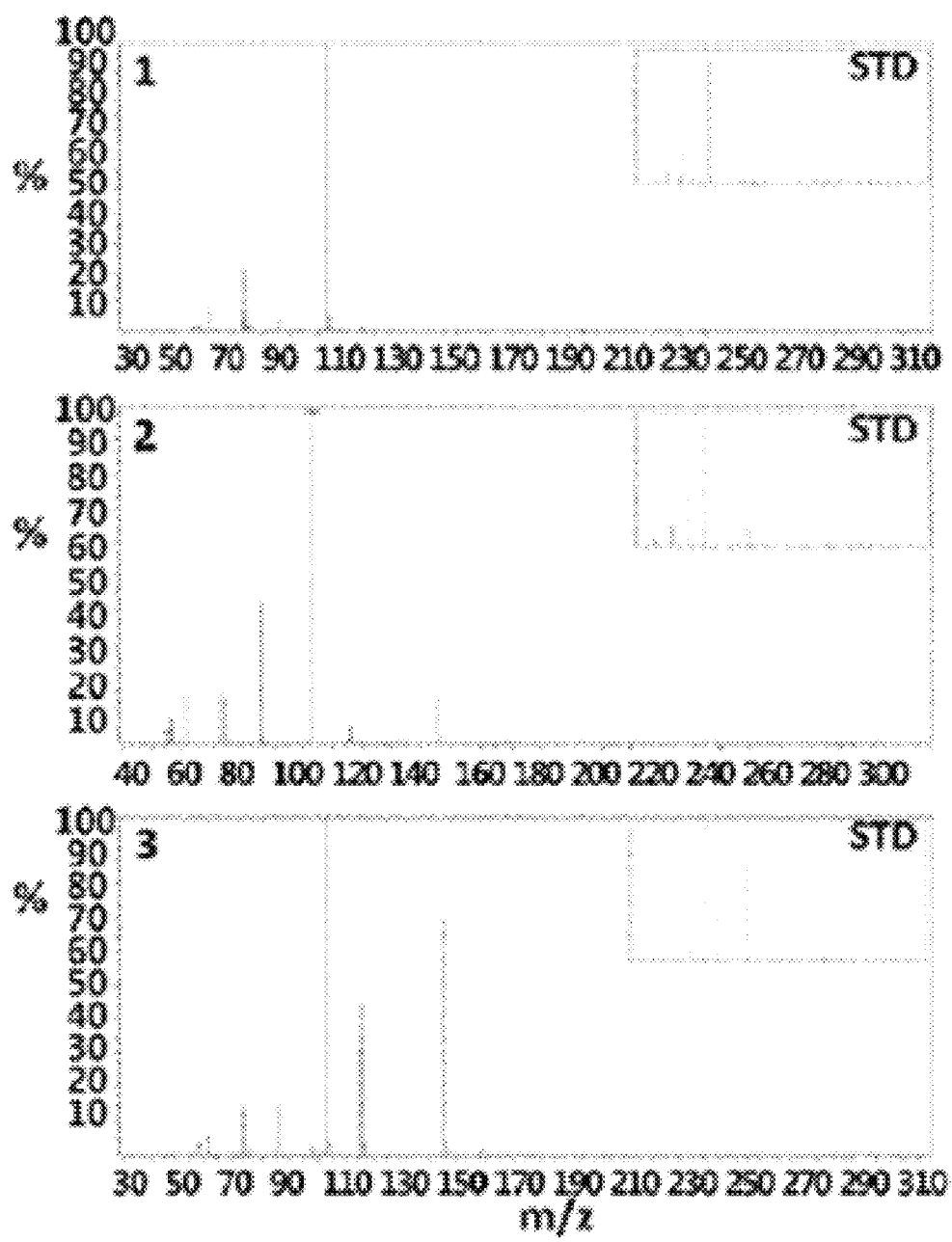
Figure 6A:
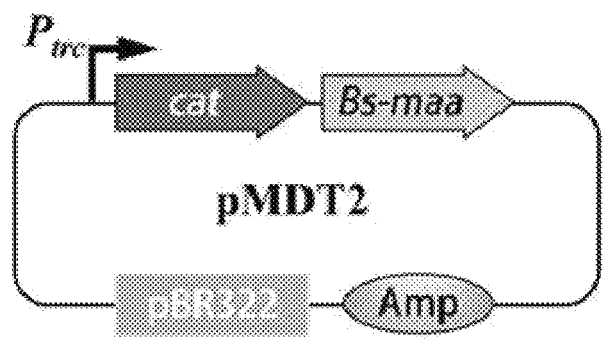
FIGS. 6A to 6D.
Figure 6B:
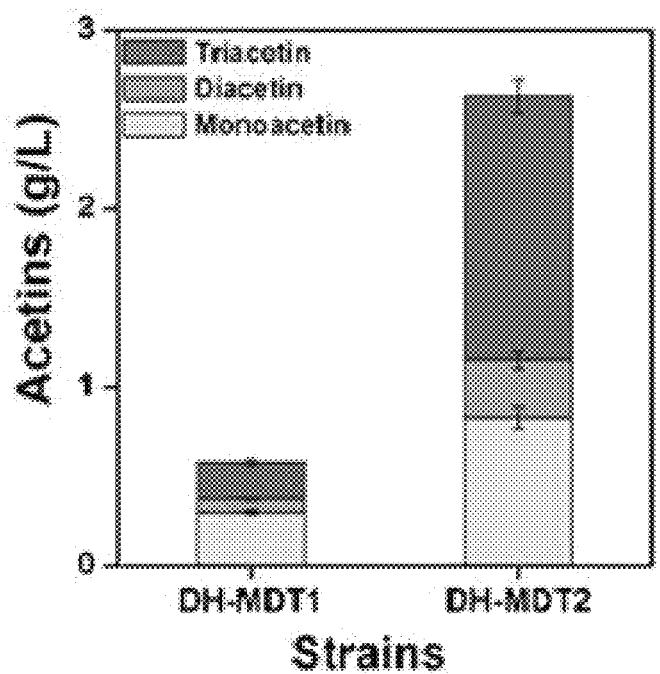
Figure 6C:
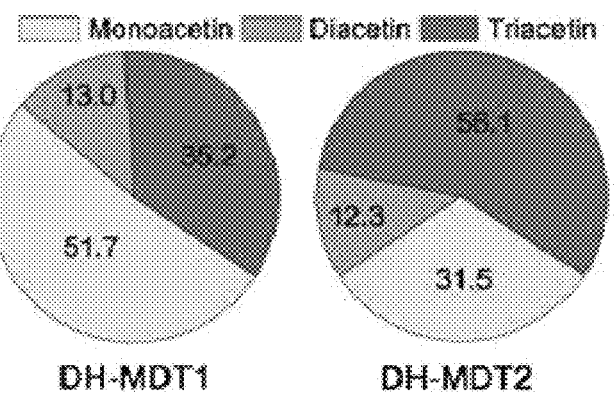
Figure 6D:
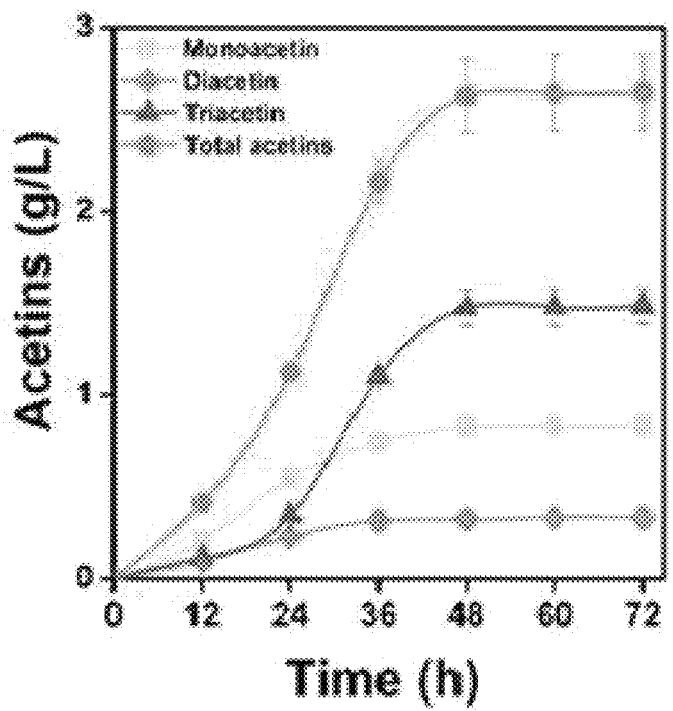

Analysis of acetin compounds was performed by GC (Agilent Technologuies 7890A, USA) equipped with a HP- INNOVAX column (19G91N-133, 30 m in length, 0.250 mm in internal diameter and 0.25 μm in film thickness) and GC-MS (GC-MS-QP2010, SHIMADZU, Japan). The acetin standard compound was purchased from Sigma (USA). Further, the acetin complex produced in the main culture was extracted from the culture medium using an ethyl acetate solvent, and 1 μL of the extracted sample was injected into GC or GC-MS. An oven temperature of the GC started from 50° C. and reached 90° C. at a rate of 20° C./min, followed by successively raising the temperature to 150° C. at a rate of 15° C./min, to 190° C. at a rate of 20° C./min, and then, to 230° C. at a rate of 15° C./min. Thereafter, the final temperature was maintained for 2 minutes. Further, a temperature of a flame ion detector (FID) was maintained at 280° C. Analyzed results according to the above analysis procedure are shown in FIGS. 5A and 5B.

Figure 3:
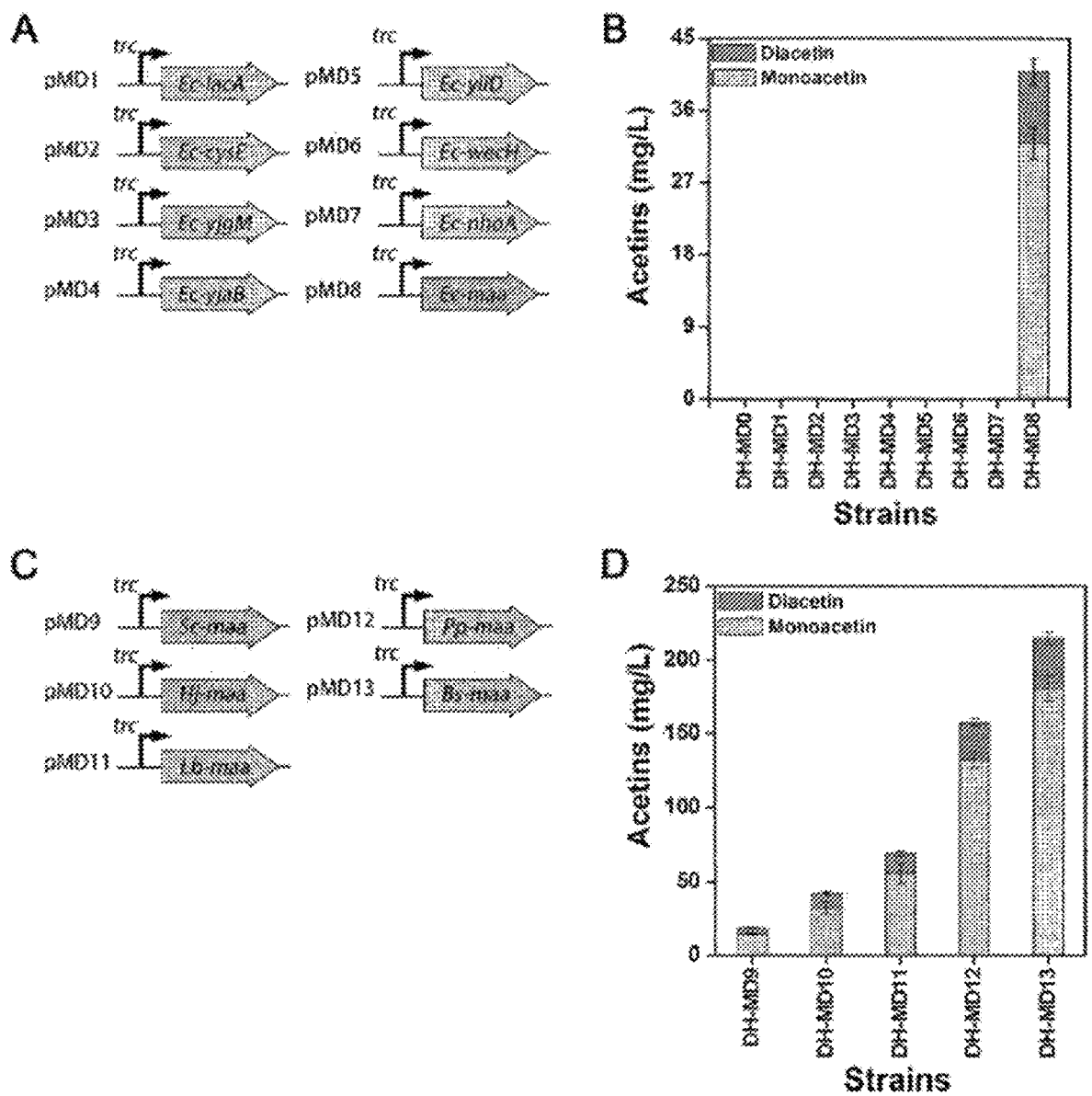
FIG. 3: (A) is a structural diagram of plasmids pMD1 to pMD8 prepared by selecting O-acetyl transferase candidate genes in *E. coli*, which are capable of transferring an acetyl group to glycerol in order to generate monoacetin and diacetin, and cloning each gene into a pTrc99A expression vector; (B) is a diagram illustrating comparison of the productivity of monoacetin and diacetin in recombinant *E. coli* DH-MD1 to DH-MD8 transformed with the plasmids of (A) (DH-MD0 shows a recombinant *E. coli* transformed with an empty vector pTrc99A); (C) is a structural diagram of plasmids pMD9 to pMD13 prepared by selecting candidate genes derived from other microorganisms that are deduced to transfer an acetyl group to glycerol based on a structure and amino acid sequence of *E. coli* maltose O-acetyl transferase (Maa), and then, cloning each gene into the pTrc99A expression vector; and (D) is a diagram illustrating comparison of the productivity of monoacetin and diacetin in recombinant *E. coli* DH-MD9 to DH-MD13 transformed with the above plasmids.

According to the culture results of the recombinant strains DH-MD1 to DH-MDA shown in FIG. 3, monoacetin and diacetin were produced only in the DH-MD8 strain transformed with the pMD8 plasmid. This demonstrates that the maltose O-acetyl transferase gene (maa) only among the eight (8) E. coli-derived O-acetyl transferase candidates has an ability to transfer the acetyl group to glycerol.

2. Production of Monoacetin Using E. coli Maa-Like Enzymes

In order to discover O-acetyl transferases having higher activity than Maa found in E. coli, BLAST search was perforated with the amino acid sequence of E. coli Maa. Then, among the microorganisms such as Staphylococcus carnosus, Halalkalicoccus jeotgali, Lactobacillus brevis, Bacillus subtilis, and Pseudomonas putida, additional five (5) of maltose O-acetyl transferases, that is, Sc-mOat (SEQ ID NO: 2), Hj-mOat. (SEQ ID NO: 3), Lb-mOat (SEQ ID NO: 4), Bs-mOat (SEQ ID NO: 5) and Pp-mOat (SEQ ID NO: 6) were obtained, followed by expressing the same in E. coli. Thereafter, the productivity of monoacetin and diacetin was compared (FIG. 3).

The microorganism-derived genes were synthesized according to the use of E. coli codons in GenScript (USA) in order to optimize expression of the genes in the host E. coli. The synthesized genes were subjected to amplification using PCR primers of Sc-maa-F (SEQ ID NO: 49)/Sc-maa-R (SEQ ID NO: 50), Hj-maa-F (SEQ ID NO: 51)/Hj-maa-R (SEQ ID NO: 52), Lb-maa-F (SEQ ID NO: 53)/Lb-maa-R (SEQ ID NO: 54), Pp-maa-F (SEQ ID NO: 55)/Pp-maa-K (SEQ ID NO: 56), Bs-maa-F (SEQ ID NO: 57)/Bs-maa-R (SEQ ID NO: 58) to acquire Sc-maa (SEQ ID NO: 17), H-j-maa (SEQ ID NO: 18), Lb-maa (SEQ ID NO: 19), Pp-maa (SEQ ID NO: 21) and Bs-maa (SEQ ID NO: 20) genes, which in turn were cloned into the pTrc99A vector using BamHI and XbaI. Using the constructed plasmids pMD9 to pMD13 in this way, E. coli DH5α was transformed, thereby forming recombinant strains DH-MD9 to DH-MD13 and using the same to compare the productivity of monoacetin and diacetin (FIG. 3).

As a result of the comparison, it was confirmed that Maa (Bs-maa) of B. subtilis exhibited the highest monoacetin and diacetin productivity. The culture method and the analysis method are the same as in Example 1.

3. Production of Triacetin Using Chloramphenicol-O-Acetyltransferase

Figure 4:
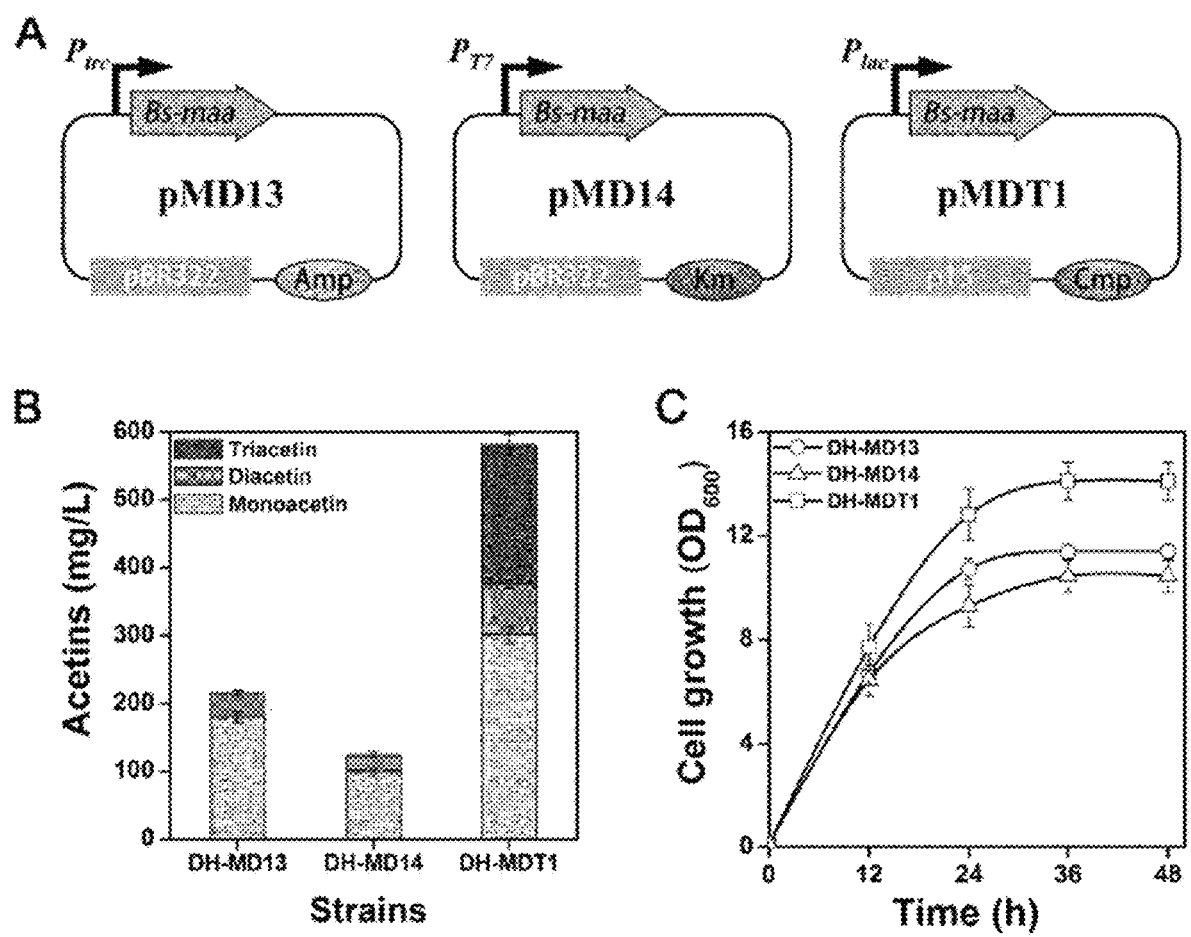
FIG. 4: (A) is a structural diagram of plasmids pMD13, pMD14 and pMDT1 prepared by cloning Maa gene (Bs-maa) of *B. subtilis*, which had the best monoacetin and diacetin productivity, into pTrc99A, pET28a and pSTV28 expression vectors; (B) is a diagram illustrating comparison of the productivity of monoacetin, diacetin and triacetin in recombinant *E. coli* DH-MD13, DH-MD14 and DH-MDT1 transformed with the above plasmids; and (C) is a diagram illustrating comparison of strain proliferation of each recombinant *E. coli*.

For optimum expression of Maa gene (Bs-maa) of B. subtilis, which exhibited the highest productivity of monoacetin and diaceatin, the gene was cloned to various vectors such as pTrc99A (SEQ ID NO: 78), pET28a (SEQ ID NO: 79) and pSTV28 (SEQ ID NO: 77), etc. to construct pMD13, pMD14 and pMDT1 plasmids, followed by forming recombinant E. coli DH-MD13, DH-MD14, and DH-MDT1 which were transformed with the above plasmids. In this regard, E. coli DH5α (DE3) was used as a transforming host strain of pMD14 having a T7 promoter. The DH5α (DE3) strain was made from E. coli DH5α using λDE3 Lysogenization Kit by Novagen (USA). In the DH-MDT1 strain, monoacetin and diacetin productivity were highest, as well as triacetin production was also observed (FIG. 4).

This is presumed to be due to the antibiotic marker chloramphenicol-O-acetyl transferase (CAT, SEQ ID NO: 7) of the pSTV28 vector. CAT is known to transfer acetyl groups to various substrates due to its extensive substrate specificity. The pMDT2 plasmid introduced and constructed before Bs-maa gene of the pMD13 plasmid so as to enhance the expression of CAT enzyme gene (cat, SEQ ID NO: 24) that produces triacetin through additional transfer of the acetyl group to monoacetin and diacetin (FIGS. 6A to 6D).

To this end, the cat gene was PCR amplified from pSTV28 using PCR primers of Cat-F (SEQ ID NO: 60)/Cat-R (SEQ ID NO: 61), cut with Sac. and BamHI and introduced into the corresponding restriction enzyme site of pMD3. With regard to DH-MDT2 recombinant strain transformed into pMDT2, both a production amount of a complex of monoacetin, diacetin and triacetin, and a ratio of triacetin were significantly increased compared to the DH-MDT1 strain. The culture method and the analysis method are the same as in Example 1.

4. Production of Triacetin Compound Using CAT-Like Enzymes

In order to further discover enzymes that convert monoacetin and diacetin to triacetin, BLAST search was performed using the amino acid sequence of the CAT enzyme. Through this search, five (5) O-acetyl transferases having high homology, that is, OAT, Bc-OAT (SEQ ID NO: 8), Pa-OAT (SEQ ID NO: 9), Ca-OAT (SEQ ID NO: 10), Ma-OAT (SEQ ID NO: 11) and Lb-OAT (SEQ ID NO: 12) were derived from Bacillus cereus, Pseudomonas aeruginosa, Clostridium acetobutylicum, Mycobacterium abscessus and Lactobacillus brevis. Further, these enzymes were synthesized according to the use of E. coli by GenScript company (USA) in order to optimize expression thereof in host E. coli.

Synthetic genes derived from the microorganism, that is, Bc-Oat (SEQ ID NO: 25), Pa-Oat (SEQ ID NO: 26), Ca-Oat (SEQ ID NO: 27), Ma-Oat (SEQ ID NO: 28) and Lb-Oat (SEQ ID NO: 29) were amplified using PCR primers of Bc.Oat-F (SEQ ID NO: 64)/Bc.Oat-R (SEQ ID NO: 65), Pa.Oat-F (SEQ ID NO: 72)/Pa.Oat-R (SEQ ID NO: 73), Ca.Oat-F (SEQ ID NO: 66)/Ca.Oat-R (SEQ ID NO: 67), Ma.Oat-F (SEQ ID NO: 70)/Ma.Oat-R (SEQ ID NO: 21), and Lb.Oat-F (SEQ ID NO: 68)/Lb.Oat-R (SEQ ID NO: 69).

Figure 7A:
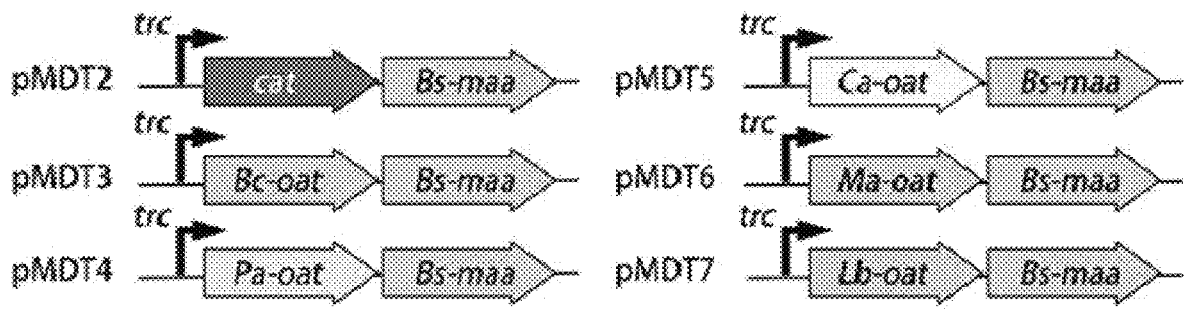
Figure 7B:
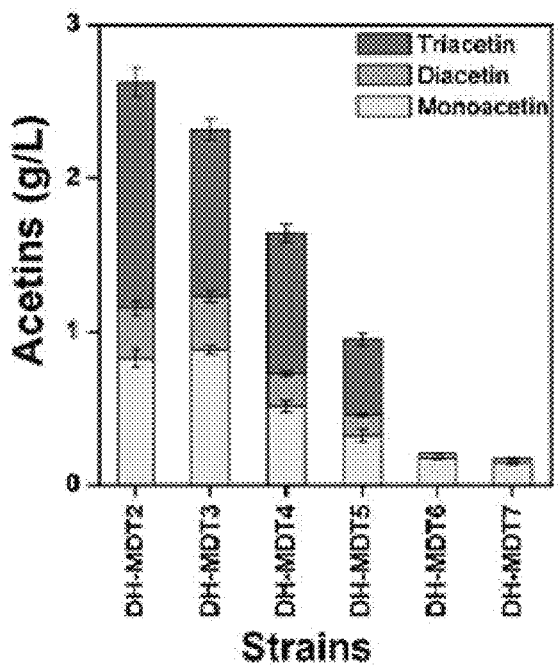

Fragments of each of the genes amplified in this way were linked to pMD13-based plasmid skeleton by HiFi DNA assembly, thus to construct plasmids pMDT3 to pMDT7 (FIGS. 7A to 7C).

HiFi DNA assembly was performed by a HiFi DNA assembly kit of NEB company (USA), and a pMD13-based plasmid skeleton was obtained by PCR amplification with PCR primers such as Trc-Bs.maa-F (SEQ ID NO: 62) and Trc-Bs.maa-R (SEQ ID NO: 63) using pMD13 as a template. Production amounts of acetin complexes of the recombinant strains DH-MDT2 to DH-MDT7 transformed with pMDT3 to pMDT7 plasmids were compared together (FIGS. 7A to 7C).

As a result, there was a significant difference in the production amount of acetin complex depending on the type of the OAT gene. Further, O-acetyl transferase derived from

*L. brevis* and *M. abscessus* did not have an ability to produce triacetin, while O-acetyl transferase derived from *B. cereus, P. aeruginosa* and *C. acetobutylicum* produced triacetin but had lower productivity than that of CAT as an antibiotic marker of pSTV28. The culture method and the analysis method are the same as in Example 1.

5. Change in Production Amount of Acetin Complex According to Amount of *E. coli* Species and Added Amount of Glycerol

Figure 8A:
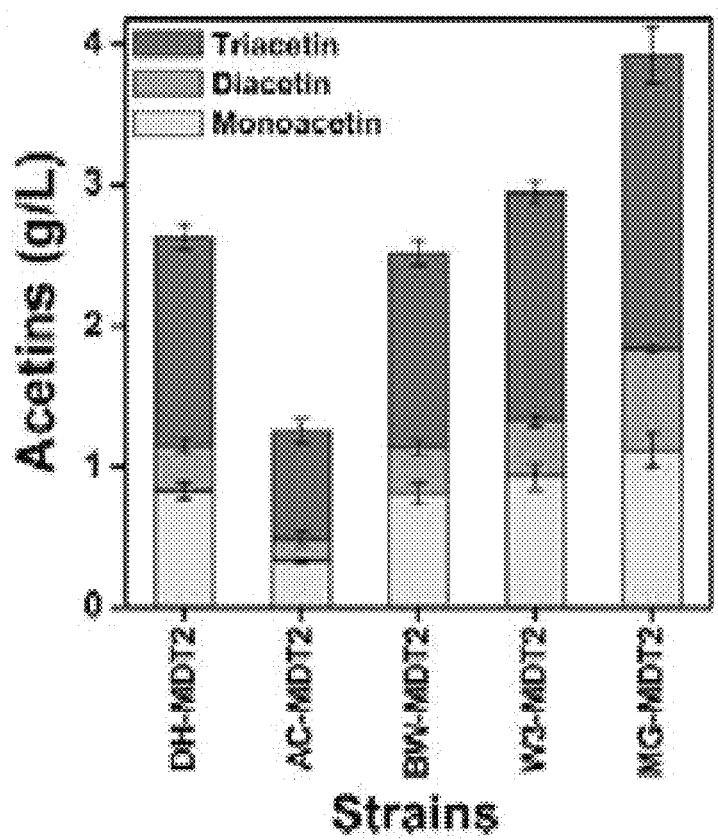
Figure 8B:
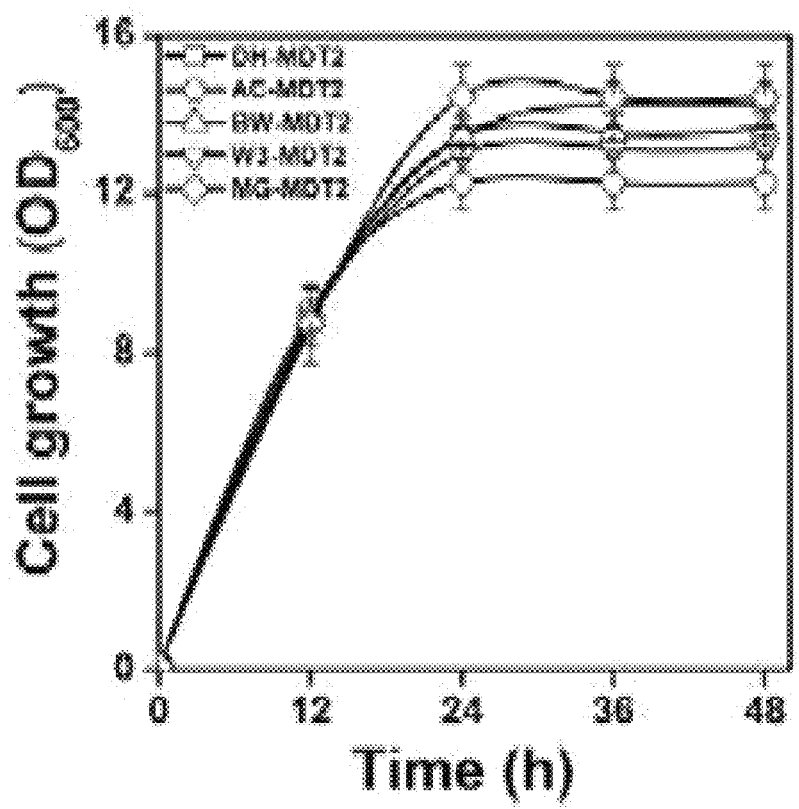

*E. coli* DH5α was used as a host in the previous examples. In order to compare productivity of acetin compounds depending on the type of *E. coli*, the present example cultured recombinant *E. coli* DH-M-MDT2, AC-MDT2, BW-MDT2, W3-MDT2 and MG-MDT2, which were transformed from *E. coli* AceCo, BW25113, W3110, and MG1655 as hosts using plasmid pMDT2, followed by comparing the productivity of the acetin complex (FIGS. 8A and 8B).

Since the productivity of the acetin complex in the recombinant strain MG-MDT2 was the highest, it was confirmed that *E. coli* MG1655 is the most suitable host for production of acetin compounds. The culture method and the analysis method are the same as in Example 1.

Figure 8C:
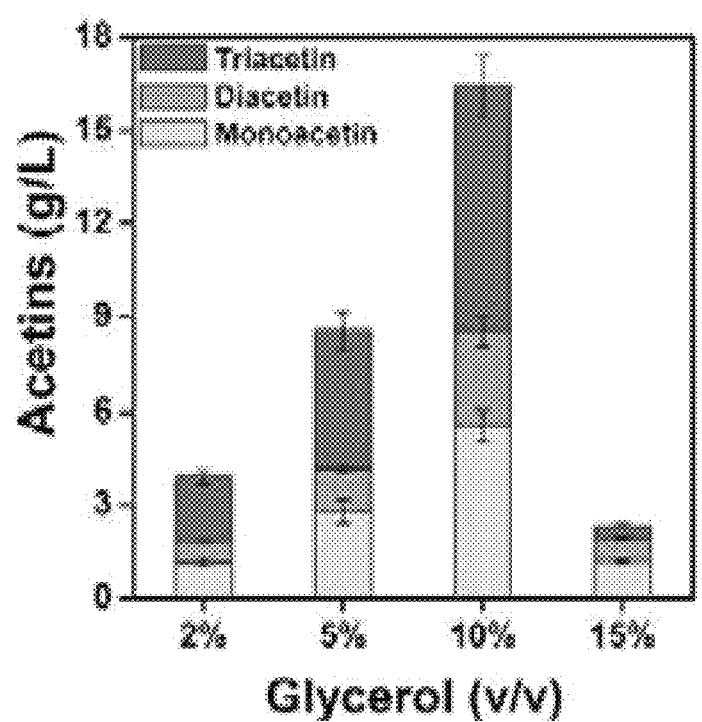
Figure 8D:
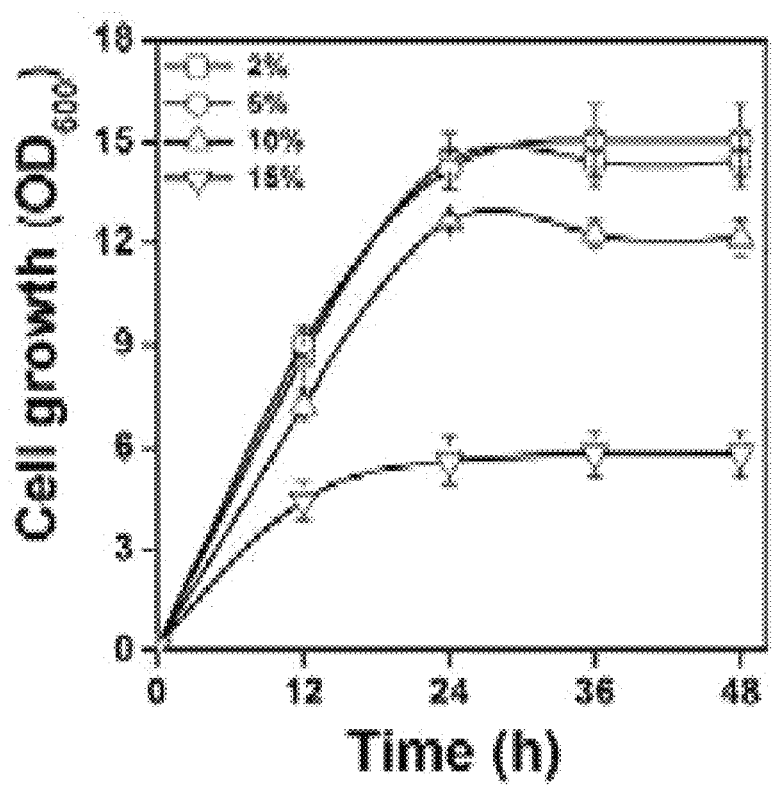
Figure 8E:
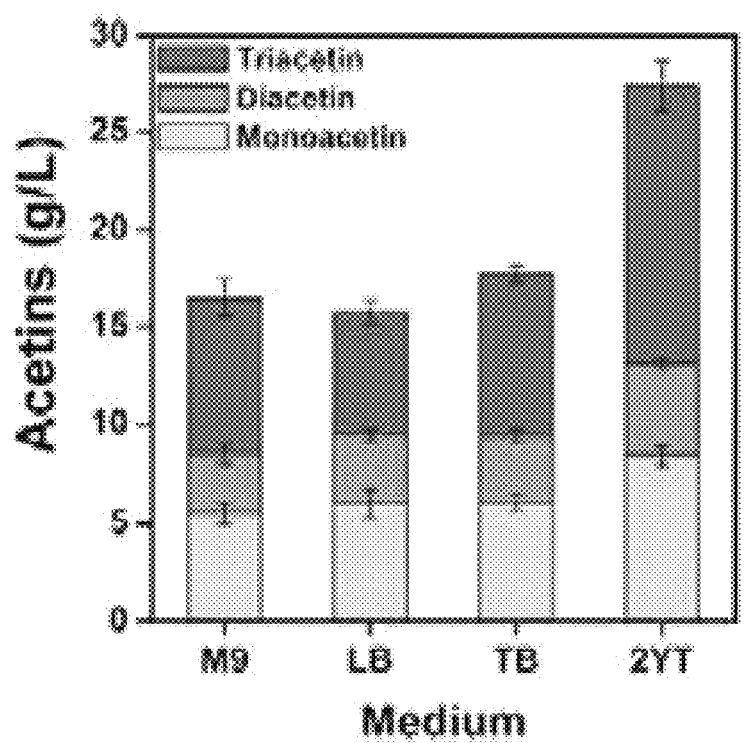
Figure 8F:
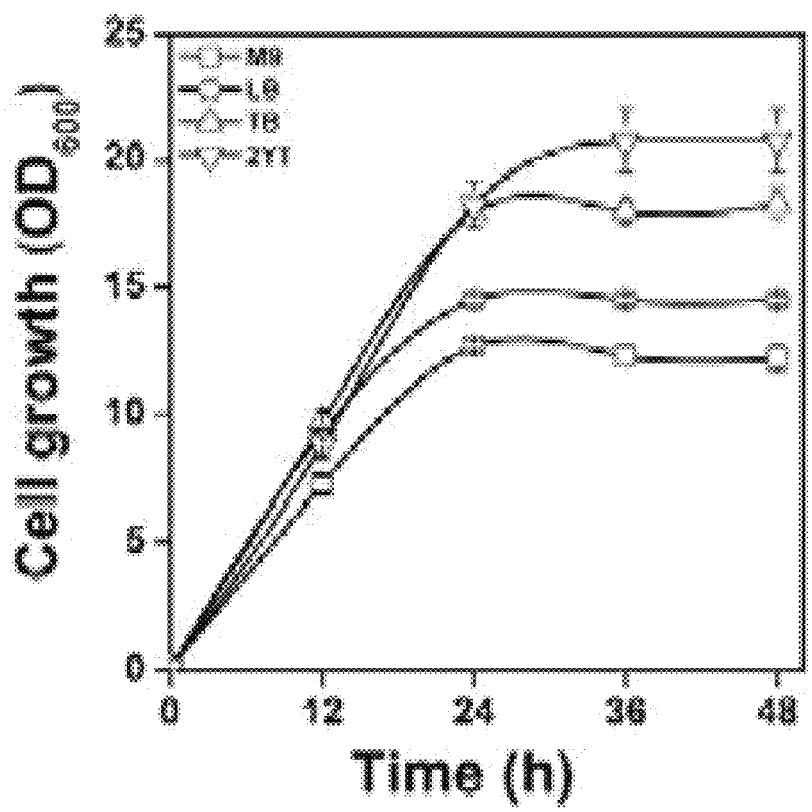

In order to examine the productivity of the acetin compound according to an amount of glycerol added as a substrate in the recombinant strain MG-MDT2, which exhibited the highest productivity of the acetin compound, all culture conditions and analysis methods used herein are the same as in Example 1 except that a concentration of added glycerol was altered between 2 to 15% (v/v) (FIGS. 8C and 8D).

The production amount of acetin complex was increased with an increase in the amount of glycerol as a starting substrate. However, in the case of adding 15% or more of glycerol, as a result, both the strain proliferation and acetin production were reduced due to effects of excessive osmotic pressure.

6. Improvement of Productivity by Removal of Enzyme Genes Degrading Acetin Compounds Since the ester compound, that is, acetin may be degraded into glycerol and acetate by ester-binding degradation enzymes (esterases, SEQ ID N(O: 13), effects of the amplification or deletion of the acetyl esterase gene (aes, SEQ ID NO: 30) of *E. coli* was considered (FIG. 9).

Aes gene fragments were obtained by PCR amplification using Ec-aes-F (SEQ ID NO: 74) and Ec-aes-R (SEQ ID NO: 75) as primers and the chromosome of *E. coli* MG1655 as a template, and then, cloned to pTrc99A with BamHI and SalI restriction enzymes, thereby constructing plasmid pTAes. In order to observe the degradation of triacetin by Aes enzyme, recombinant strains EW-Empty and BW-Aes, which were transformed from *E. coli* BW25113 with an empty vector pTrc99A and plasmid pTAes, respectively, were prepared, followed by culturing the same in a medium containing 15 g/L of triacetin standard compound added thereto. The culture conditions were identical with the production conditions of the acetin complex used in the above examples (A and B of FIG. 9).

Although degradation of the triacetin standard compound occurred in both the BW-Empty and BW-Aes strains, a degree of degradation was confirmed to be much higher in the BW-Aes overexpressing the aes gene. A small amount of diacetin was measured in the culture medium by the degradation of triacetin, but no monoacetin was detected. It is presumed that because the degradation of monoacetin occurs more rapidly.

Figure 9:
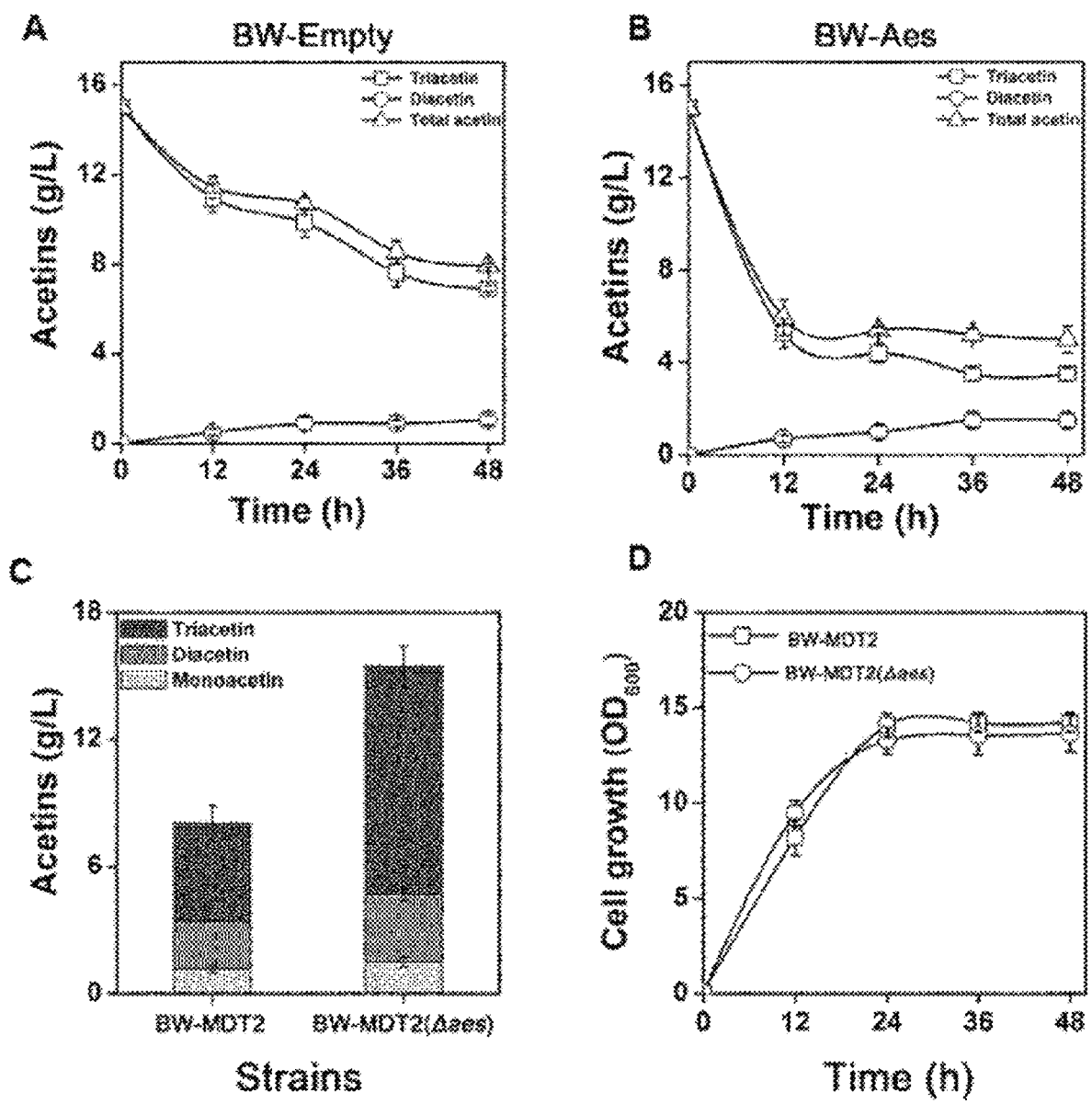
FIG. 9 illustrates observation of change in the acetin compound through amplification and deletion of acetylesterase gene (aes) in *E. coli* BW25113, wherein: (A) and (B) show observation of degradation pattern of triacetin after inoculating the recombinant strains BW-Empty and BW-Aes BW25113, which were transformed with pTr99A and pTAes, respectively, in 2YT medium including 15 g/L of triacetin standard compound added thereto; (C) illustrates comparison of the productivity of acetin complex by culturing the recombinant strains BW-MDT2 and BW-MDT2 (Daes), which were transformed from BW25113 and aes gene-deleted JW0465 stains, respectively, with the plasmid pMDT2, in 2YT medium including 10% (v/v) of glycerol added thereto; and (D) illustrates comparison of strain proliferation of the above recombinant strains.

Based on the above results that the acetin compounds are degraded by aes, JW0465 strain, in which the aes gene is deleted, and the wild-type strain BW25113 were transformed with pMDT2 to prepare recombinant strains BW-MDT2 and BW-MDT2 (Daes), respectively, followed by comparing the production of acetin complex and strain proliferation in the above recombinant strains (C and D of FIG. 9).

The JW0465 strain is a strain in which the aes gene is deleted from the BW25113 strain, and was sold by NBRP (NIG, Japan). The strain was cultured in a 2T composite medium (containing 16 g tryptone, 10 g yeast extract, and 5 g sodium chloride per liter) to which 10 (v/v) glycerol as a substrate is added. Other culture and analysis conditions are the same as in the above examples.

It was confirmed that the degradation of acetin was inhibited in the BW-MDT2 (Daes) strain in which the aes gene is deleted, thereby the production amount of the acetin complex was about 2 times higher than that of the BW-MDT2 strain. On the other hand, there was no difference in the strain proliferation between two recombinant strains. From these results, it could be seen chat aes is involved in the degradation of the acetin compound, and the productivity of the acetin complex may be improved when deleting the aes gene.

7. Production of Acetin Compound Using Glucose as Substrate

Figure 2:
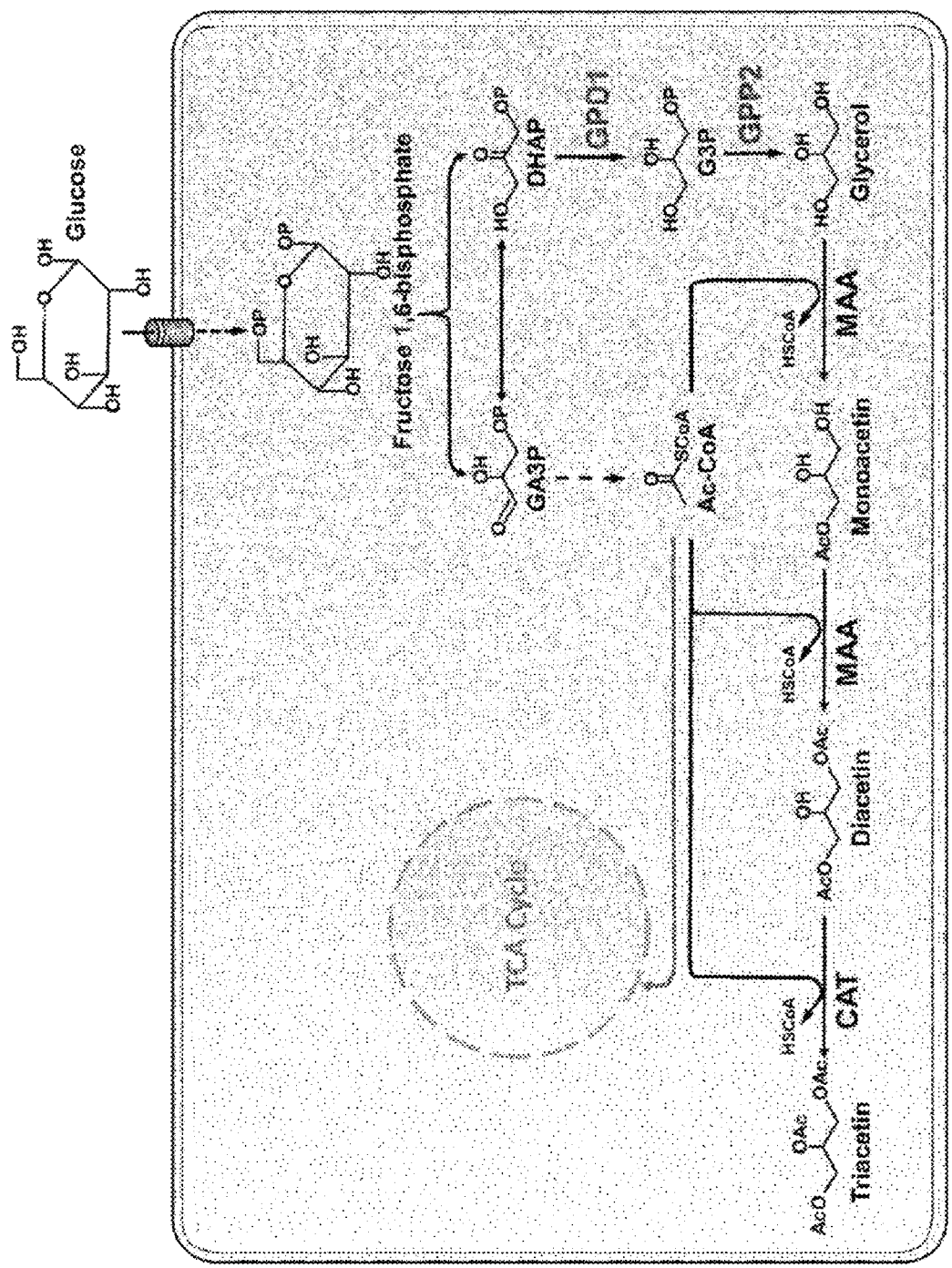
FIG. 2 illustrates a pathway in which glucose introduced into cells is converted into monoacetin, diacetin and triacetin.

As shown in FIG. 2, glycerone phosphate (DHAP), which is an intermediate metabolite or a glycolysis pathway (Embden-Meyerhof pathway), may be converted into glycerol via glycerol-3-phosphate by glycerol-3-phosphate dehydrogenase and DL-glycerol-3-phosphatase. Therefore, the production of an acetin complex based on glucose as a starting substrate is also possible through additional overexpression of glycerol-3-phosphate dehydrogenase and DL-glycerol-3-phosphatase. The glycerol-3-phosphate dehydrogenase and DL-glycerol-3-phosphatase used herein were Gpd1 (SEQ ID NO: 14) and Gpp2 (SEQ ID NO: 15) derived from *Saccharomyces cerevisiae*, respectively.

Figure 10:
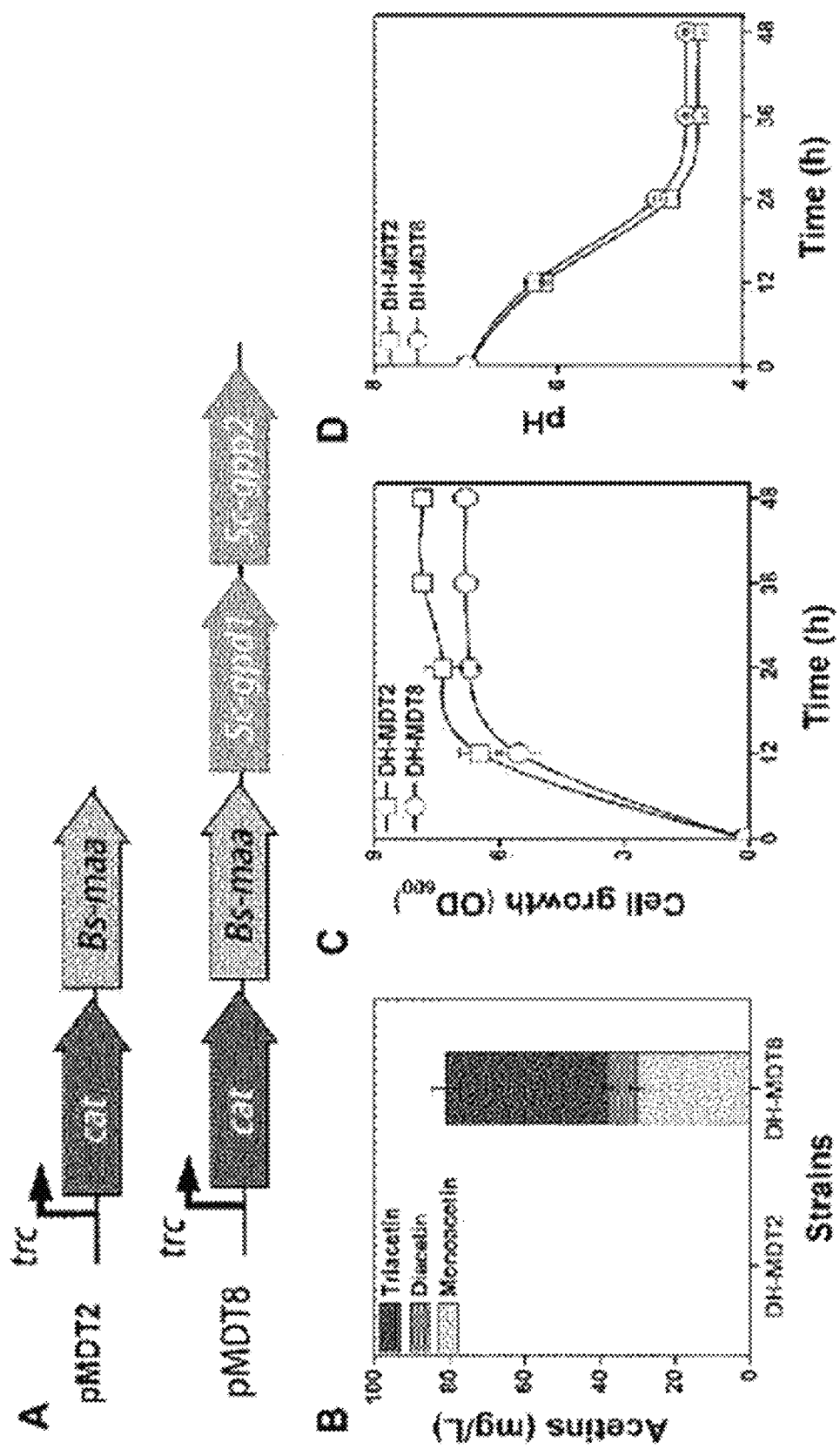
FIG. 10: (A) is a structural diagram of plasmid pMDT8 prepared by cloning *Saccharomyces cerevisiae*-derived glycerol production genes Sc-gpd1 and Sc-gpp2 in pMDT2 plasmid in order to produce an acetin complex from glucose; (B) illustrates the production of acetin complex from glucose of a recombinant *E. coli* DH-MDT8 transformed with the above plasmid; (C) illustrates strain proliferation of the *E. coli*; and (D) illustrates pH change of the culture medium.
Figure 11:
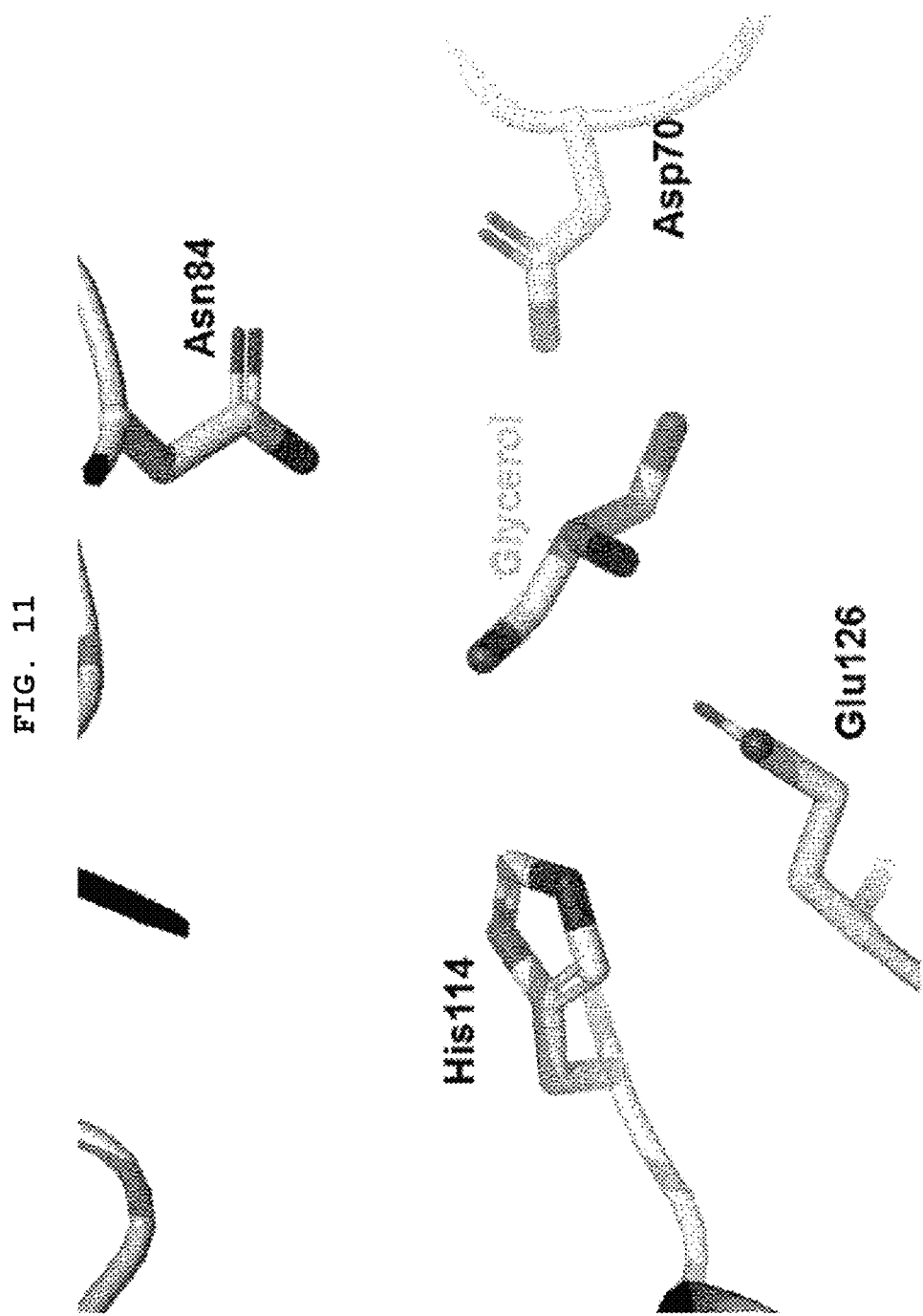
FIG. 11 illustrates a structure of the substrate binding site in BsMAA maltose acetyl transferase, wherein key residues of glycerol acetylation are aspartic acid (ASP) at position 70, asparagine (ASN) at position 84, histidine at position 114 (HIS), and glutamic acid (GLU) at position 126 of the amino acid sequence.
Figure 12:
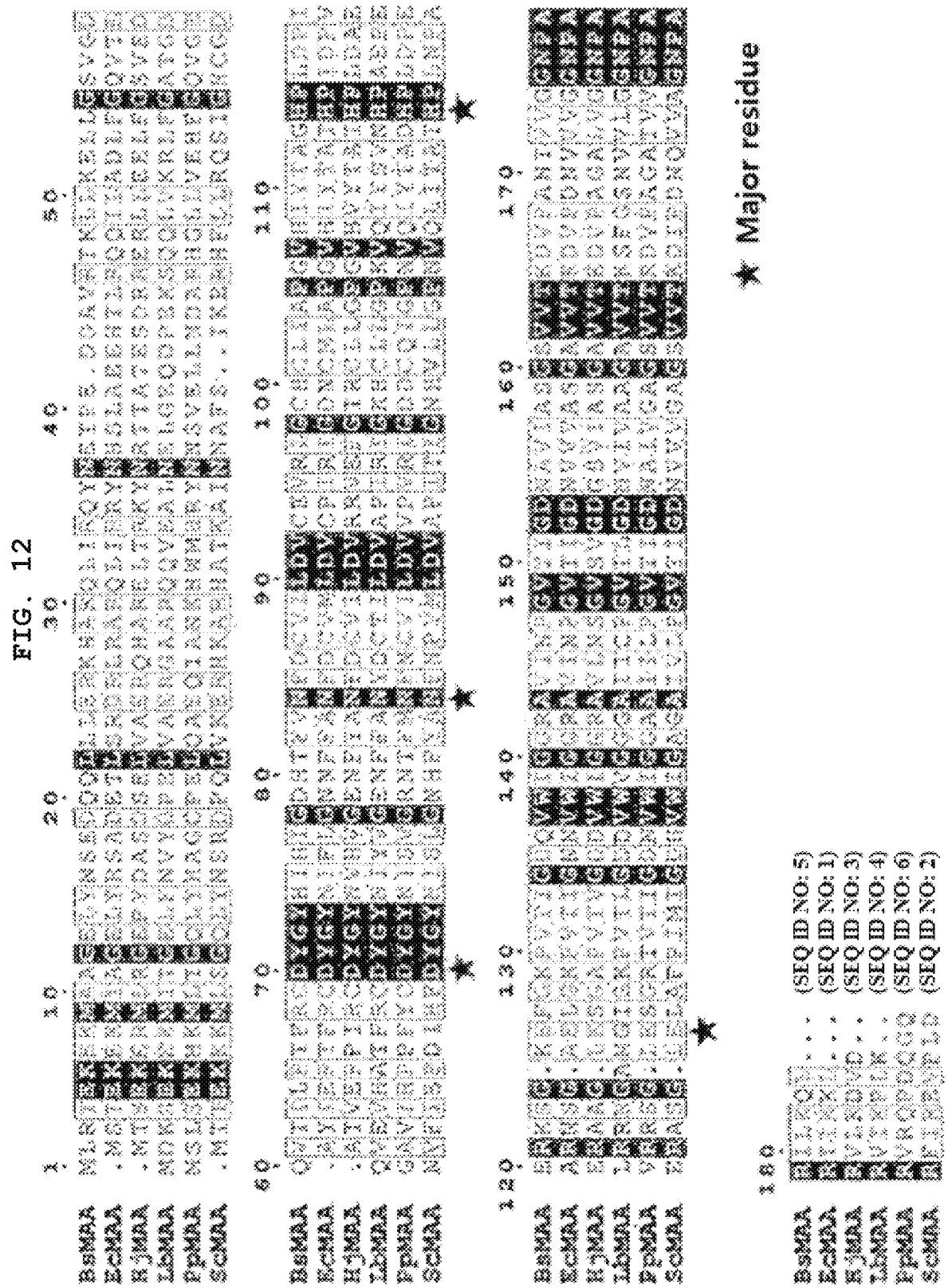
FIG. 12 illustrates results of sequence alignment of *Bacillus subtilis* MAA-like enzymes.
Figure 13:
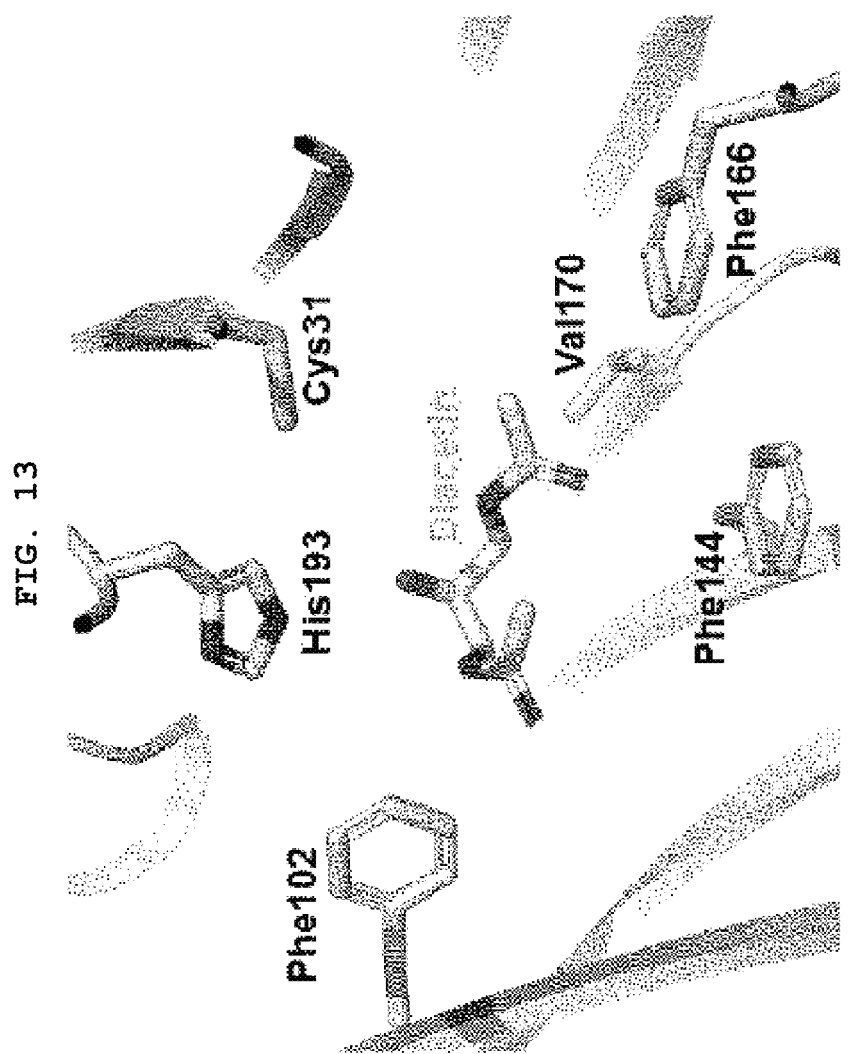
FIG. 13 illustrates a structure of the substrate binding site in CAT chloramphenicol-O-acetyl transferase, wherein key residues of diacetin acetylation are phenylalanine (PHE) at position 102, phenylalanine (PHE) at position 143, and histidine (HIS) at position 193 of the amino acid sequence. In this regard, the residues at positions 102 and 143 of the sequence may be replaced with amino acids having similar properties such as isoleucine (ILE) and tyrosine (TYR), respectively. This could be seen in FIG. 14 for comparison of the amino acid sequence alignment of the second O-acetyl transferase.
Figure 14:
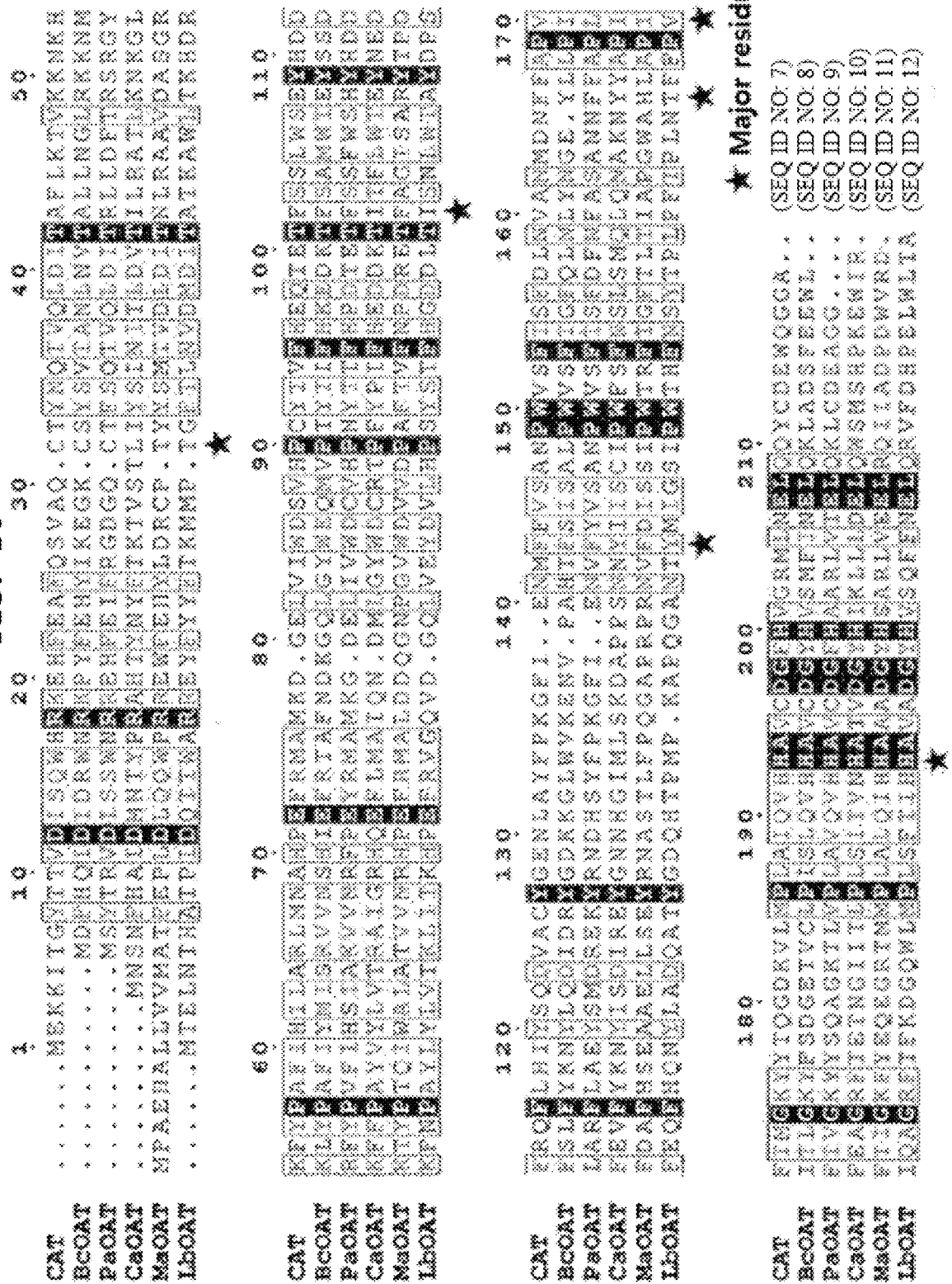
FIG. 14 illustrates results of the sequence alignment of CAT-like enzymes.

FIG. 10: (A) is a structural diagram of plasmid pMDT8, which was produced by cloning the glycerol production genes, that is, Sc-gpd1 (SEQ ID NO: 31) and Sc-gpp2 (SEQ ID NO: 32) derived from *Saccharomyces cerevisiae* into the pMDT2 plasmid, thereby producing an acetin complex from glucose; and (B), (C) and (D) illustrate the production of the acetin complex from glucose of the recombinant *E. coli* DH-MDT8 transformed with the above plasmid, the strain proliferation thereof, and the pH change of the culture medium, as compared to the control, that is, DH-MDT2.

Sc-gpd1 was subjected to PCR amplification using Sc-gpd1-F (SEQ ID NO: 76) and Sc-gpd1-R (SEQ ID NO: 59) as primers and the chromosomes of *Saccharomyces cerevisiae* as a template, while Sc-gpp2 was subjected to PCR amplification using Sc-gpp2-F (SEQ ID NO: 22) and Sc-gpp2-R (SEQ ID NO: 23) as primers. Then, the former was cut with BamHI and PstI restriction enzymes, while the latter was cut with PstI and HindIII restriction enzymes, followed by introducing each of the treated products into the corresponding restriction enzyme sites of pMDT2 plasmid, thereby constructing plasmid pMD8. Cultivation was performed for 48 hours by inoculating the recombinant strains DH-MDT2 and DH-MDT8 in a 2YT composite medium to which 1 (w/v) was added instead of glycerol. Other culture and analysis conditions are the same as in the above examples.

Among the above two recombinant strains, only in the DH-MDTS strain, in which the genes Sc-gpd1 and Sc-gpp2 were expressed, the acetin complex was produced while strain proliferation and pH of the culture medium were similar.

A sequence listing electronically submitted with the present application on Apr. 26, 2021 as an ASCII text file named 20210426_Q50421LC10_TU_SEQ, created on Apr. 23, 2021 and having a size of 77,000 bytes, is incorporated herein by reference in its entirety.

What is claimed is:

1. A method for production of acetin, the method comprising:

preparing a transformed microorganism including a gene encoding a first O-acetyl transferase to express the first O-acetyl transferase; and reacting acetyl-CoA with glycerol in the presence of the first O-acetyl transferase to obtain the acetin, wherein the first O-acetyl transferase is maltose O-acetyl transferase.

2. The method according to claim 1, wherein an amino acid sequence of the first O-acetyl transferase has a sequence motif comprising:

aspartic acid (ASP) at a position corresponding to position 70 of the amino acid sequence of SEQ ID NO: 5;

asparagine (ASN) at a position corresponding to position 84 of the amino acid sequence of SEQ ID NO: 5;

histidine (HIS) at a position corresponding to position 114 of the amino acid sequence of SEQ ID NO: 5; and glutamic acid (GLU) at a position corresponding to position 126 of the amino acid sequence of SEQ ID NO: 5.

3. The method according to claim 2, wherein an amino acid sequence of the first O-acetyl transferase has a sequence motif comprising:

tyrosine (TYR) or phenylalanine (PHE) at a position corresponding to position 15 of the amino acid sequence of SEQ ID NO: 5;

arginine (ARG) or glutamine (GLN) at a position corresponding to position 26 of the amino acid sequence of SEQ ID NO: 5;

arginine (ARG) or lysine (LYS) at a position corresponding to position 30 of the amino acid sequence of SEQ ID NO: 5; and phenylalanine (PHE) or tyrosine (TYR) at a position corresponding to position 82 of the amino acid sequence of SEQ ID NO: 5.

4. The method according to claim 1, wherein the first O-acetyl transferase is composed of any one sequence of SEQ ID NOS: 1 to 6.

5. The method according to claim 1, wherein the acetin comprises monoacetin and diacetin, and the method further comprises reacting the diacetin as a reaction product with acetyl-CoA in the presence of chloramphenicol-O-acetyl transferase or a second O-acetyl transferase, thus to obtain triacetin.

6. The method according to claim 5, wherein an amino acid sequence of the second O-acetyl transferase has a sequence motif comprising:
cysteine (CYS) or leucine (LEU) at a position corresponding to position 31 of the amino acid sequence of SEQ ID NO: 7;
phenylalanine (PHE) or isoleucine (ILE) at a position corresponding to position 102 of the amino acid sequence of SEQ ID NO: 7;
phenylalanine (PHE) or tyrosine (TYR) at a position corresponding to position 143 of the amino acid sequence of SEQ ID NO: 7;
phenylalanine (PHE) or tyrosine (TYR) at a position corresponding to position 166 of the amino acid sequence of SEQ ID NO: 7;
valine (VAL), isoleucine (ILE) or leucine (LEU) at a position corresponding to position 170 of the amino acid sequence of SEQ ID NO: 7; and
histidine (HIS) at a position corresponding to position 193 of the amino acid sequence of SEQ ID NO: 7.

7. The method according to claim 5, wherein the chloramphenicol-O-acetyl transferase is composed of the sequence of SEQ ID NO: 7, and the second O-acetyl transferase is composed of any one sequence of SEQ ID NOS: 8 to 10.

8. A method for production of acetin, the method comprising:
preparing a transformed microorganism that expresses a gene encoding a first O-acetyl transferase; and
culturing the transformed microorganism in a medium containing glycerol to produce the acetin,
wherein the first O-acetyl transferase is maltose O-acetyl transferase.

9. The method according to claim 8, wherein an amino acid sequence of the first O-acetyl transferase has a sequence motif comprising:
aspartic acid (ASP) at a position corresponding to position 70 of the amino acid sequence of SEQ ID NO: 5;
asparagine (ASN) at a position corresponding to position 84 of the amino acid sequence of SEQ ID NO: 5;
histidine (HIS) at a position corresponding to position 114 of the amino acid sequence of SEQ ID NO: 5; and
glutamic acid (GLU) at a position corresponding to position 126 of the amino acid sequence of SEQ ID NO: 5.

10. The method according to claim 8, wherein an amino acid sequence of the first O-acetyl transferase has a sequence motif comprising:
tyrosine (TYR) or phenylalanine (PHE) at a position corresponding to position 15 of the amino acid sequence of SEQ ID NO: 5;
arginine (ARG) or glutamine (GLN) at a position corresponding to position 26 of the amino acid sequence of SEQ ID NO: 5;
arginine (ARG) or lysine (LYS) at a position corresponding to position 30 of the amino acid sequence of SEQ ID NO: 5; and
phenylalanine (PHE) or tyrosine (TYR) at a position corresponding to position 82 of the amino acid sequence of SEQ ID NO: 5.

11. The method according to claim 8, wherein the gene encoding the first O-acetyl transferase is composed of any one sequence of SEQ ID NOS: 16 to 21.

12. The method according to claim 8, wherein the transformed microorganism further expresses a gene encoding chloramphenicol-O-acetyl transferase or a second O-acetyl transferase that transfers an acetyl group to diacetin.

13. The method according to claim 12, wherein an amino acid sequence of the second O-acetyl transferase has a sequence motif comprising:
cysteine (CYS) or leucine (LEU) at a position corresponding to position 31 of the amino acid sequence of SEQ ID NO: 7;
phenylalanine (PHE) or isoleucine (ILE) at a position corresponding to position 102 of the amino acid sequence of SEQ ID NO: 7;
phenylalanine (PHE) or tyrosine (TYR) at a position corresponding to position 143 of the amino acid sequence of SEQ ID NO: 7;
phenylalanine (PHE) or tyrosine (TYR) at a position corresponding to position 166 of the amino acid sequence of SEQ ID NO: 7;
valine (VAL), isoleucine (ILE) or leucine (LEU) at a position corresponding to position 170 of the amino acid sequence of SEQ ID NO: 7; and
histidine (HIS) at a position corresponding to position 193 of the amino acid sequence of SEQ ID NO: 7.

14. The method according to claim 12, wherein the gene encoding chloramphenicol-O-acetyl transferase is composed of the sequence of SEQ ID NO: 24, and the gene encoding the second O-acetyl transferase is composed of any one sequence of SEQ ID NOS: 25 to 27.

15. The method according to claim 8, wherein the transformed microorganism includes a gene encoding acetyl-esterase, which is attenuated or deleted.

16. The method according to claim 8, wherein the transformed microorganism further expresses genes encoding glycerol-3-phosphate dehydrogenase and DL-glycerol-3-phosphatase, and the medium includes glucose.

* * * * *

```
                            SEQUENCE LISTING

<160> NUMBER OF SEQ ID NOS: 86

<210> SEQ ID NO 1
<211> LENGTH: 183
<212> TYPE: PRT
<213> ORGANISM: Escherichia coli

<400> SEQUENCE: 1

Met Ser Thr Glu Lys Glu Lys Met Ile Ala Gly Glu Leu Tyr Arg Ser
1               5                   10                  15

Ala Asp Glu Thr Leu Ser Arg Asp Arg Leu Ala Arg Gln Leu Ile
            20                  25                  30

His Arg Tyr Asn His Ser Leu Ala Glu Glu His Thr Leu Arg Gln Gln
        35                  40                  45

Ile Leu Ala Asp Leu Phe Gly Gln Val Thr Glu Ala Tyr Ile Glu Pro
    50                  55                  60

Thr Phe Arg Cys Asp Tyr Gly Tyr Asn Ile Phe Leu Gly Asn Asn Phe
65                  70                  75                  80

Phe Ala Asn Phe Asp Cys Val Met Leu Asp Val Cys Pro Ile Arg Ile
                85                  90                  95

Gly Asp Asn Cys Met Leu Ala Pro Gly Val His Ile Tyr Thr Ala Thr
            100                 105                 110

His Pro Ile Asp Pro Val Ala Arg Asn Ser Gly Ala Glu Leu Gly Lys
        115                 120                 125

Pro Val Thr Ile Gly Asn Asn Val Trp Ile Gly Arg Ala Val Ile
    130                 135                 140

Asn Pro Gly Val Thr Ile Gly Asp Asn Val Val Val Ala Ser Gly Ala
145                 150                 155                 160

Val Val Thr Lys Asp Val Pro Asp Asn Val Val Val Gly Gly Asn Pro
                165                 170                 175

Ala Arg Ile Ile Lys Lys Leu
            180

<210> SEQ ID NO 2
<211> LENGTH: 185
<212> TYPE: PRT
<213> ORGANISM: Staphylococcus carnosus

<400> SEQUENCE: 2

Met Thr Thr Glu Lys Glu Lys Met Leu Ser Gly Gln Leu Tyr Asn Ser
1               5                   10                  15

Arg Asp Pro Gln Leu Val Lys Glu Arg His Lys Ala Arg His Ala Thr
            20                  25                  30

Lys Ala Ile Asn Asn Ala Phe Ser Ile Lys Glu Arg His Phe Leu Leu
        35                  40                  45

Arg Gln Ser Ile Gly His Cys Gly Asp Asn Val Phe Ile Glu Pro Asp
    50                  55                  60

Ile His Phe Asp Tyr Gly Tyr Asn Ile Ser Leu Gly Asn His Phe Tyr
65                  70                  75                  80

Ala Asn Phe Asn Pro Val Met Leu Asp Val Ala Pro Ile Thr Ile Gly
                85                  90                  95
```

-continued

```
Asn His Val Leu Leu Gly Pro Asn Val Gln Leu Ile Thr Ala Thr His
            100                 105                 110

Pro Leu Asn Pro Ala Glu Arg Ala Ser Gly Leu Glu Leu Ala Phe Pro
        115                 120                 125

Ile Met Ile Gly Asp His Val Trp Ile Gly Ala Gly Ala Ile Val Leu
    130                 135                 140

Pro Gly Val Thr Ile Gly Asp Asn Val Val Gly Ala Gly Ser Val
145                 150                 155                 160

Val Thr Lys Asp Ile Pro Asp Asn Gln Val Val Ala Gly Asn Pro Ala
                165                 170                 175

Arg Phe Ile Arg Glu Val Pro Leu Asp
            180                 185

<210> SEQ ID NO 3
<211> LENGTH: 184
<212> TYPE: PRT
<213> ORGANISM: Unknown
<220> FEATURE:
<223> OTHER INFORMATION: Halalkalicoccus jeotgali

<400> SEQUENCE: 3

Met Thr Ser Glu Lys Glu Arg Met Leu Arg Gly Glu Pro Tyr Asp Ala
1               5                   10                  15

Ser Asp Ser Glu Leu Val Ala Glu Arg Gln His Ala Arg Glu Leu Thr
            20                  25                  30

Arg Lys Tyr Asn Arg Thr Thr Ala Thr Glu Ser Asp Arg Arg Glu Arg
        35                  40                  45

Leu Leu Glu Glu Leu Phe Gly Ser Val Glu Asp Ala Thr Val Glu Pro
    50                  55                  60

Pro Ile Arg Cys Asp Tyr Gly Tyr Asn Val His Val Gly Glu Asn Phe
65                  70                  75                  80

Tyr Ala Asn Phe Asp Cys Val Ile Leu Asp Val Arg Arg Val Glu Phe
                85                  90                  95

Gly Thr Arg Cys Leu Leu Gly Pro Gly Val His Val Tyr Thr Ala Thr
            100                 105                 110

His Pro Leu Asp Ala Glu Glu Arg Ala Ala Gly Leu Glu Ser Gly Ala
        115                 120                 125

Pro Val Thr Val Gly Asp Asp Val Trp Ile Gly Gly Arg Ala Val Leu
    130                 135                 140

Asn Ser Gly Val Ser Val Gly Asp Gly Ser Val Ile Ala Ser Gly Ala
145                 150                 155                 160

Val Val Thr Glu Asp Val Pro Ala Gly Ala Leu Val Gly Gly Asn Pro
                165                 170                 175

Ala Arg Val Leu Lys Asp Val Asp
            180

<210> SEQ ID NO 4
<211> LENGTH: 187
<212> TYPE: PRT
<213> ORGANISM: Lactobacillus brevis

<400> SEQUENCE: 4

Met Asp Lys Ser Glu Lys Glu Lys Met Ile Thr Gly Glu Leu Phe Asn
1               5                   10                  15

Val Tyr Asp Pro Glu Leu Val Ala Glu Arg Gly Ala Ala Arg Gln Gln
            20                  25                  30

Val Glu Ala Leu Asn Glu Leu Gly Glu Gln Asp Pro Glu Lys Ser Gln
```

```
              35                  40                  45
Gln Leu Val Lys Arg Leu Phe Gly Ala Thr Gly Asp Gln Val Glu Val
         50                  55                  60

His Ala Thr Phe Arg Cys Asp Tyr Gly Tyr Asn Ile Tyr Val Gly Glu
 65                  70                  75                  80

Asn Phe Phe Ala Asn Tyr Asp Cys Thr Ile Leu Asp Val Ala Pro Ile
                 85                  90                  95

Arg Ile Gly Lys His Cys Leu Leu Gly Pro Lys Val Gln Ile Tyr Ser
            100                 105                 110

Val Asn His Pro Ala Glu Pro Glu Leu Arg Arg Asn Gly Ala Met Gly
        115                 120                 125

Ile Gly Lys Pro Val Thr Leu Gly Asp Asp Val Trp Val Gly Gly
    130                 135                 140

Ala Ile Ile Cys Pro Gly Val Thr Leu Gly Asp Asn Val Ile Val Ala
145                 150                 155                 160

Ala Gly Ala Val Val Thr Lys Ser Phe Gly Ser Asn Val Val Leu Gly
                165                 170                 175

Gly Asn Pro Ala Arg Val Ile Lys Pro Leu Lys
            180                 185

<210> SEQ ID NO 5
<211> LENGTH: 184
<212> TYPE: PRT
<213> ORGANISM: Bacillus subtilis

<400> SEQUENCE: 5

Met Leu Arg Thr Glu Lys Glu Lys Met Ala Ala Gly Glu Leu Tyr Asn
 1               5                  10                  15

Ser Glu Asp Gln Gln Leu Leu Leu Glu Arg Lys His Ala Arg Gln Leu
             20                  25                  30

Ile Arg Gln Tyr Asn Glu Thr Pro Glu Asp Asp Ala Val Arg Thr Lys
         35                  40                  45

Leu Leu Lys Glu Leu Leu Gly Ser Val Gly Asp Gln Val Thr Ile Leu
 50                  55                  60

Pro Thr Phe Arg Cys Asp Tyr Gly Tyr His Ile His Ile Gly Asp His
 65                  70                  75                  80

Thr Phe Val Asn Phe Asp Cys Val Ile Leu Asp Val Cys Glu Val Arg
                 85                  90                  95

Ile Gly Cys His Cys Leu Ile Ala Pro Gly Val His Ile Tyr Thr Ala
            100                 105                 110

Gly His Pro Leu Asp Pro Ile Glu Arg Lys Ser Gly Lys Glu Phe Gly
        115                 120                 125

Lys Pro Val Thr Ile Gly Asp Gln Val Trp Ile Gly Gly Arg Ala Val
    130                 135                 140

Ile Asn Pro Gly Val Thr Ile Gly Asp Asn Ala Val Ile Ala Ser Gly
145                 150                 155                 160

Ser Val Val Thr Lys Asp Val Pro Ala Asn Thr Val Val Gly Gly Asn
                165                 170                 175

Pro Ala Arg Ile Leu Lys Gln Leu
            180

<210> SEQ ID NO 6
<211> LENGTH: 188
<212> TYPE: PRT
<213> ORGANISM: Pseudomonas putida
```

```
<400> SEQUENCE: 6

Met Ser Leu Ser Glu Lys His Lys Met Leu Thr Gly Gln Leu Tyr His
1               5                   10                  15

Ala Gly Cys Pro Glu Leu Gln Ala Glu Gln Ile Ala Asn Lys His Trp
            20                  25                  30

Met His Arg Tyr Asn Asn Ser Val Glu Leu Leu Asn Asp Ala Arg His
        35                  40                  45

Gly Leu Leu Val Glu His Phe Gly Gln Val Gly Glu Gly Ala Val Ile
    50                  55                  60

Arg Pro Pro Phe Tyr Cys Asp Tyr Gly Tyr Asn Ile Ser Val Gly Arg
65                  70                  75                  80

Asn Thr Phe Met Asn Phe Asn Cys Val Ile Leu Asp Val Val Pro Val
                85                  90                  95

Arg Ile Gly Asp Asp Cys Gln Ile Gly Pro Asn Val Gln Ile Tyr Thr
            100                 105                 110

Ala Asp His Pro Leu Asp Pro Glu Val Arg Arg Ser Gly Leu Glu Ser
        115                 120                 125

Gly Arg Thr Val Thr Ile Gly Asp Asn Val Trp Ile Gly Gly Ala Ala
    130                 135                 140

Ile Ile Leu Pro Gly Val Thr Ile Gly Asp Asn Ala Ile Val Gly Ala
145                 150                 155                 160

Gly Ser Val Val Thr Arg Asp Val Pro Ala Gly Ala Thr Val Val Gly
                165                 170                 175

Asn Pro Ala Arg Val Arg Gln Pro Asp Gln Gly Gln
            180                 185

<210> SEQ ID NO 7
<211> LENGTH: 219
<212> TYPE: PRT
<213> ORGANISM: Artificial Sequence
<220> FEATURE:
<223> OTHER INFORMATION: pSTV28 VECTOR

<400> SEQUENCE: 7

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
```

-continued

```
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 8
<211> LENGTH: 215
<212> TYPE: PRT
<213> ORGANISM: Bacillus cereus

<400> SEQUENCE: 8

Met Asp Phe His Gln Ile Asp Ile Asp Arg Trp Asn Arg Lys Pro Tyr
1               5                   10                  15

Phe Glu His Tyr Ile Lys Glu Gly Lys Cys Ser Tyr Ser Val Thr Ala
            20                  25                  30

Asn Leu Asn Val Thr Ala Leu Leu Asn Gly Leu Arg Lys Lys Asn Met
        35                  40                  45

Lys Leu Tyr Pro Ala Phe Ile Tyr Met Ile Ser Arg Val Val Asn Ser
    50                  55                  60

His Ile Glu Phe Arg Thr Ala Phe Asn Asp Lys Gly Gln Leu Gly Tyr
65                  70                  75                  80

Trp Glu Gln Met Val Pro Thr Tyr Thr Ile Phe His Lys Glu Asp Lys
                85                  90                  95

Thr Phe Ser Ala Met Trp Thr Glu Tyr Ser Ser Asp Phe Ser Leu Phe
            100                 105                 110

Tyr Lys Asn Tyr Leu Gln Asp Ile Asp Arg Tyr Gly Asp Lys Lys Gly
        115                 120                 125

Leu Trp Val Lys Glu Asn Val Pro Ala His Thr Phe Ser Ile Ser Ala
    130                 135                 140

Leu Pro Trp Val Ser Phe Thr Gly Phe Gln Leu Asn Leu Tyr Asn Gly
145                 150                 155                 160

Glu Tyr Leu Leu Pro Ile Ile Thr Leu Gly Lys Tyr Phe Ser Asp Gly
                165                 170                 175

Glu Thr Val Cys Leu Pro Ile Ser Leu Gln Val His His Ala Val Cys
            180                 185                 190

Asp Gly Tyr His Val Ser Met Phe Ile Asn Glu Leu Gln Lys Leu Ala
        195                 200                 205

Asp Ser Phe Glu Glu Trp Leu
    210                 215

<210> SEQ ID NO 9
<211> LENGTH: 212
<212> TYPE: PRT
<213> ORGANISM: Pseudomonas aeruginosa

<400> SEQUENCE: 9

Met Ser Tyr Thr Arg Val Asp Ile Ser Ser Trp Asn Arg Arg Glu His
1               5                   10                  15

Phe Glu Ile Phe Arg Gly Asp Gly Gln Cys Thr Phe Ser Gln Thr Val
            20                  25                  30

Gln Leu Asp Ile Thr Arg Leu Leu Asp Phe Thr Arg Ser Arg Gly Tyr
        35                  40                  45

Arg Phe Tyr Pro Val Phe Ile His Ser Ile Ala Lys Val Val Asn Arg
```

```
            50                  55                  60
Phe Pro Glu Tyr Arg Met Ala Met Lys Gly Asp Glu Leu Ile Val Trp
 65                  70                  75                  80

Asp Cys Val His Pro Asn Tyr Thr Thr Phe His Pro Asp Thr Glu Thr
                 85                  90                  95

Phe Ser Ser Phe Trp Ser His Tyr His Asp Asp Leu Ala Arg Phe Leu
                100                 105                 110

Ala Glu Tyr Ser Met Asp Arg Glu Lys Tyr Arg Asn Asp His Ser Tyr
                115                 120                 125

Phe Pro Lys Gly Phe Ile Glu Asn Val Phe Tyr Val Ser Ala Asn Pro
            130                 135                 140

Trp Val Ser Phe Thr Ser Phe Asp Phe Asn Phe Ala Ser Ala Asn Asn
145                 150                 155                 160

Phe Phe Ala Pro Leu Phe Thr Val Gly Lys Tyr Tyr Ser Gln Ala Gly
                165                 170                 175

Lys Thr Leu Val Pro Leu Ala Val Gln Val His His Ala Val Cys Asp
                180                 185                 190

Gly Phe His Ala Ala Arg Leu Val Thr Glu Leu Gln Lys Leu Cys Asp
                195                 200                 205

Glu Ala Gly Gly
            210

<210> SEQ ID NO 10
<211> LENGTH: 220
<212> TYPE: PRT
<213> ORGANISM: Clostridium acetobutylicum

<400> SEQUENCE: 10

Met Asn Ser Asn Phe His Ala Ile Asp Met Asn Thr Tyr Pro Arg Ala
  1               5                  10                  15

His Thr Tyr Asn Tyr Phe Thr Lys Thr Val Ser Thr Leu Ile Tyr Ser
                 20                  25                  30

Ile Asn Ile Thr Leu Asp Val Thr Ile Leu Arg Ala Thr Leu Lys Asn
             35                  40                  45

Lys Gly Leu Lys Phe Phe Pro Ala Tyr Val Tyr Leu Val Thr Arg Ala
 50                  55                  60

Ile Gly Arg His Gln Glu Phe Leu Met Ala Ile Gln Asn Asp Met Leu
 65                  70                  75                  80

Gly Tyr Trp Asp Cys Arg Thr Pro Phe Tyr Pro Ile Phe His Glu Asp
                 85                  90                  95

Asp Lys Thr Ile Thr Phe Leu Trp Thr Glu Tyr Asn Glu Asp Phe Glu
                100                 105                 110

Val Phe Tyr Lys Asn Tyr Ile Ser Asp Ile Arg Glu Tyr Gly Asn Asn
                115                 120                 125

His Gly Ile Met Leu Ser Lys Asp Ala Pro Ser Asn Asn Tyr Ile
            130                 135                 140

Ile Ser Cys Ile Pro Trp Phe Ser Phe Asn Ser Leu Ser Met Gln Leu
145                 150                 155                 160

Gln Asn Ala Lys Asn Tyr Tyr Ala Pro Ile Phe Glu Ala Gly Arg Phe
                165                 170                 175

Thr Glu Thr Asn Gly Ile Ile Thr Leu Pro Leu Ser Ile Thr Val Asn
            180                 185                 190

His Ala Thr Val Asp Gly Tyr His Ile Lys Leu Leu Leu Asp Glu Leu
            195                 200                 205
```

```
Gln Trp Ser Met Ser His Pro Lys Glu Trp Ile Arg
    210             215                 220
```

<210> SEQ ID NO 11
<211> LENGTH: 229
<212> TYPE: PRT
<213> ORGANISM: Mycobacterium abscessus

<400> SEQUENCE: 11

```
Met Pro Ala Glu His Ala Leu Leu Val Val Met Ala Thr Phe Glu Pro
1               5                   10                  15

Leu Asp Leu Gln Gln Trp Pro Arg Arg Glu Trp Phe Glu His Tyr Leu
            20                  25                  30

Asp Arg Cys Pro Thr Tyr Tyr Ser Met Thr Val Asp Leu Asp Ile Thr
        35                  40                  45

Asn Leu Arg Ala Ala Val Asp Ala Ser Gly Arg Lys Thr Tyr Pro Thr
50                  55                  60

Gln Ile Trp Ala Leu Ala Thr Val Val Asn Arg His Pro Glu Phe Arg
65                  70                  75                  80

Met Ala Leu Asp Asp Gln Gly Asn Pro Gly Val Trp Asp Val Val Asp
                85                  90                  95

Pro Ala Phe Thr Val Phe Asn Pro Asp Arg Glu Thr Phe Ala Gly Ile
            100                 105                 110

Ser Ala Arg Tyr Thr Pro Asp Phe Asp Ala Phe His Ser Glu Ala Ala
        115                 120                 125

Glu Leu Leu Ser Glu Tyr Arg Asn Ala Ser Thr Leu Phe Pro Gln Gly
130                 135                 140

Ala Pro Arg Pro Arg Asn Val Phe Asp Ile Ser Ser Ile Pro Trp Thr
145                 150                 155                 160

Arg Phe Thr Gly Phe Thr Leu Thr Ile Ala Pro Gly Trp Ala His Leu
                165                 170                 175

Ala Pro Ile Phe Thr Ile Gly Lys Phe Tyr Glu Gln Glu Gly Arg Thr
            180                 185                 190

Met Met Pro Leu Ala Leu Gln Ile His His Ala Ala Ala Asp Gly Tyr
        195                 200                 205

His Ser Ala Arg Leu Val Glu Glu Leu Arg Gln Ile Ile Ala Asp Pro
    210                 215                 220

Asp Trp Val Arg Asp
225
```

<210> SEQ ID NO 12
<211> LENGTH: 222
<212> TYPE: PRT
<213> ORGANISM: Lactobacillus brevis

<400> SEQUENCE: 12

```
Met Thr Glu Leu Asn Thr His Ala Thr Pro Ile Asp Gln Thr Thr Trp
1               5                   10                  15

Ala Arg Arg Glu Tyr Phe Tyr Tyr Phe Thr Lys Met Met Pro Thr Gly
            20                  25                  30

Phe Thr Leu Asn Val Asp Met Asp Ile Thr Ala Thr Lys Ala Trp Leu
        35                  40                  45

Thr Lys His Asp Arg Lys Phe Asn Pro Ala Tyr Leu Tyr Leu Val Thr
    50                  55                  60

Lys Leu Ile Thr Lys His Pro Glu Phe Arg Val Gly Gln Val Asp Gly
65                  70                  75                  80
```

```
Gln Leu Val Glu Tyr Asp Val Leu His Pro Ser Tyr Ser Thr Phe His
                85                  90                  95
Gly Asp Asp Leu Thr Ile Ser Asn Leu Trp Thr Ala Tyr Asp Pro Ser
            100                 105                 110
Phe Glu Gln Phe His Gln Asn Tyr Leu Ala Asp Gln Ala Thr Tyr Gly
        115                 120                 125
Asp Gln His Thr Pro Met Pro Lys Ala Pro Gln Gly Ala Asn Thr Tyr
    130                 135                 140
Met Ile Gly Ser Ile Pro Trp Thr His Phe Asn Ser Tyr Thr Pro Leu
145                 150                 155                 160
Pro Phe Thr Pro Leu Asn Thr Phe Phe Pro Val Ile Gln Ala Gly Arg
                165                 170                 175
Phe Thr Phe Lys Asp Gly Gln Trp Leu Met Pro Leu Ser Phe Thr Ile
            180                 185                 190
His His Ala Val Ala Asp Gly Tyr His Val Ser Gln Phe Phe Asn Glu
        195                 200                 205
Leu Gln Arg Val Phe Asp His Pro Glu Leu Trp Leu Thr Ala
    210                 215                 220

<210> SEQ ID NO 13
<211> LENGTH: 319
<212> TYPE: PRT
<213> ORGANISM: Escherichia coli

<400> SEQUENCE: 13

Met Lys Pro Glu Asn Lys Leu Pro Val Leu Asp Leu Ile Ser Ala Glu
1               5                   10                  15
Met Lys Thr Val Val Asn Thr Leu Gln Pro Asp Leu Pro Pro Trp Pro
                20                  25                  30
Ala Thr Gly Thr Ile Ala Glu Gln Arg Gln Tyr Tyr Thr Leu Glu Arg
            35                  40                  45
Arg Phe Trp Asn Ala Gly Ala Pro Glu Met Ala Thr Arg Ala Tyr Met
        50                  55                  60
Val Pro Thr Lys Tyr Gly Gln Val Glu Thr Arg Leu Phe Cys Pro Gln
65                  70                  75                  80
Pro Asp Ser Pro Ala Thr Leu Phe Tyr Leu His Gly Gly Gly Phe Ile
                85                  90                  95
Leu Gly Asn Leu Asp Thr His Asp Arg Ile Met Arg Leu Leu Ala Ser
            100                 105                 110
Tyr Ser Gln Cys Thr Val Ile Gly Ile Asp Tyr Thr Leu Ser Pro Glu
        115                 120                 125
Ala Arg Phe Pro Gln Ala Ile Glu Glu Ile Val Ala Ala Cys Cys Tyr
    130                 135                 140
Phe His Gln Gln Ala Glu Asp Tyr Gln Ile Asn Met Ser Arg Ile Gly
145                 150                 155                 160
Phe Ala Gly Asp Ser Ala Gly Ala Met Leu Ala Leu Ala Ser Ala Leu
                165                 170                 175
Trp Leu Arg Asp Lys Gln Ile Asp Cys Gly Lys Val Ala Gly Val Leu
            180                 185                 190
Leu Trp Tyr Gly Leu Tyr Gly Leu Arg Asp Ser Val Thr Arg Arg Leu
        195                 200                 205
Leu Gly Gly Val Trp Asp Gly Leu Thr Gln Gln Asp Leu Gln Met Tyr
    210                 215                 220
Glu Glu Ala Tyr Leu Ser Asn Asp Ala Asp Arg Glu Ser Pro Tyr Tyr
225                 230                 235                 240
```

```
Cys Leu Phe Asn Asn Asp Leu Thr Arg Glu Val Pro Pro Cys Phe Ile
            245                 250                 255

Ala Gly Ala Glu Phe Asp Pro Leu Leu Asp Asp Ser Arg Leu Leu Tyr
        260                 265                 270

Gln Thr Leu Ala Ala His Gln Gln Pro Cys Glu Phe Lys Leu Tyr Pro
        275                 280                 285

Gly Thr Leu His Ala Phe Leu His Tyr Ser Arg Met Met Lys Thr Ala
        290                 295                 300

Asp Glu Ala Leu Arg Asp Gly Ala Gln Phe Phe Thr Ala Gln Leu
305                 310                 315

<210> SEQ ID NO 14
<211> LENGTH: 391
<212> TYPE: PRT
<213> ORGANISM: Saccharomyces cerevisiae

<400> SEQUENCE: 14

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
```

```
                290              295              300
Thr Cys Ala Gly Gly Arg Asn Val Lys Val Ala Arg Leu Met Ala Thr
305             310              315              320

Ser Gly Lys Asp Ala Trp Glu Cys Glu Lys Glu Leu Leu Asn Gly Gln
            325              330              335

Ser Ala Gln Gly Leu Ile Thr Cys Lys Glu Val His Glu Trp Leu Glu
            340              345              350

Thr Cys Gly Ser Val Glu Asp Phe Pro Leu Phe Glu Ala Val Tyr Gln
            355              360              365

Ile Val Tyr Asn Asn Tyr Pro Met Lys Asn Leu Pro Asp Met Ile Glu
            370              375              380

Glu Leu Asp Leu His Glu Asp
385             390

<210> SEQ ID NO 15
<211> LENGTH: 250
<212> TYPE: PRT
<213> ORGANISM: Saccharomyces cerevisiae

<400> SEQUENCE: 15

Met Gly Leu Thr Thr Lys Pro Leu Ser Leu Lys Val Asn Ala Ala Leu
1               5                10               15

Phe Asp Val Asp Gly Thr Ile Ile Ser Gln Pro Ala Ile Ala Ala
            20               25               30

Phe Trp Arg Asp Phe Gly Lys Asp Lys Pro Tyr Phe Asp Ala Glu His
            35               40               45

Val Ile Gln Val Ser His Gly Trp Arg Thr Phe Asp Ala Ile Ala Lys
50              55               60

Phe Ala Pro Asp Phe Ala Asn Glu Glu Tyr Val Asn Lys Leu Glu Ala
65              70               75               80

Glu Ile Pro Val Lys Tyr Gly Glu Lys Ser Ile Glu Val Pro Gly Ala
            85               90               95

Val Lys Leu Cys Asn Ala Leu Asn Ala Leu Pro Lys Glu Lys Trp Ala
            100              105              110

Val Ala Thr Ser Gly Thr Arg Asp Met Ala Gln Lys Trp Phe Glu His
            115              120              125

Leu Gly Ile Arg Arg Pro Lys Tyr Phe Ile Thr Ala Asn Asp Val Lys
            130              135              140

Gln Gly Lys Pro His Pro Glu Pro Tyr Leu Lys Gly Arg Asn Gly Leu
145             150              155              160

Gly Tyr Pro Ile Asn Glu Gln Asp Pro Ser Lys Ser Lys Val Val Val
            165              170              175

Phe Glu Asp Ala Pro Ala Gly Ile Ala Ala Gly Lys Ala Ala Gly Cys
            180              185              190

Lys Ile Ile Gly Ile Ala Thr Thr Phe Asp Leu Asp Phe Leu Lys Glu
            195              200              205

Lys Gly Cys Asp Ile Ile Val Lys Asn His Glu Ser Ile Arg Val Gly
            210              215              220

Gly Tyr Asn Ala Glu Thr Asp Glu Val Glu Phe Ile Phe Asp Asp Tyr
225             230              235              240

Leu Tyr Ala Lys Asp Asp Leu Leu Lys Trp
            245              250

<210> SEQ ID NO 16
<211> LENGTH: 552
```

```
<212> TYPE: DNA
<213> ORGANISM: Escherichia coli

<400> SEQUENCE: 16
atgagcacag aaaaagaaaa gatgattgct ggtgagttgt atcgctcggc agatgagacg      60
ttatctcgcg atcgcctgcg cgctcgtcag cttattcacc gatacaatca ttccctggcg    120
gaagagcaca cattacgcca gcaaattctc gctgatctat tcggtcaggt gacagaggct    180
tatattgagc aacgtttcg ctgtgactat ggctataaca ttttctcgg taataatttt      240
ttcgccaact tcgattgcgt gatgcttgat gtctgcccta ttcgcatcgg tgataactgt    300
atgttggcac caggcgttca tatctacacg caacacatc ccatcgaccc tgtagcacgt     360
aatagcggtg ctgaactggg gaaacccgtc accatcggta ataacgtctg gattggcgga    420
cgcgcggtca ttaaccctgg tgtgaccatt ggtgataacg tcgtggtagc ctcaggtgca    480
gttgtcacaa aagatgtccc ggacaacgtt gtcgtgggcg gtaatccagc cagaataatt    540
aaaaaattgt aa                                                        552

<210> SEQ ID NO 17
<211> LENGTH: 547
<212> TYPE: DNA
<213> ORGANISM: Staphylococcus carnosus

<400> SEQUENCE: 17
atgaccaccg agaaggaaaa aatgctgagc ggtcagctgt acaacagccg tgacccgcaa      60
ctggttaagg agcgtcacaa agcgcgtcac gcgaccaagg cgatcaacaa cgcgttcagc    120
attaaaacgt cactttctgc tgcgtcagag catcggtcac tgcggcgaca acgtgttcat    180
cgagccggaa ttcacttcga ttacggttac aacattagcc tgggcaacca cttctatgcg    240
aactttaacc cgttagctgg atgtggcgcc gatcaccatt ggtaaccacg ttctgctggg    300
cccgaacgtg caactgatcc cgcgaccac ccgctgaacc cggcggagcg tgcgagcggt     360
ctggaactgg cgttcccgat catattggcg accacgtttg gattggtgcg ggtgcgattg    420
ttctgccggg tgtgaccatt gcgataactg gttgtgggtg cgggcagcgt tgtgaccaag    480
gacatcccgg ataaccaggt tgtgcgggca accggcgcgt tttattcgtg aagtgccgct    540
ggattaa                                                              547

<210> SEQ ID NO 18
<211> LENGTH: 554
<212> TYPE: DNA
<213> ORGANISM: Unknown
<220> FEATURE:
<223> OTHER INFORMATION: Halalkalicoccus jeotgali

<400> SEQUENCE: 18
atgaccagcg agaaggaacg tatgctgcgt ggtgagccgt acgacgcgag cgatagcgag      60
ctggttgcgg aacgtcagca cgcgcgtgaa ctgacccgta aatataaccg taccaccgcg    120
accgagagcg accgtcgtga acgtctgctg gaggaactgt tcggtagcgt ggaggacgcg    180
accgttgaac cgccgatccg ttgcgattac ggttataacg ttcacgttgg cgagaacttc    240
tacgcgaact ttgactgcgt tattctggat gtgcgtcgtg ttgaatttgg cacccgttgc    300
ctgctgggtc cgggtgttca cgtttatacc gcgacccacc cgctggatgc ggaggaacgt    360
gcggcgggtc tggagagcgg tgcgccggtg accgttggtg acgatgtgtg atcggtggc     420
cgtgcggttc tgaacagcgg cgtgagcttg gtgacggcag cgtgattgcg agcggtgcgg    480
```

```
tggttaccga agatgttccg gcgggcgcgc tggttggtgg caacccggcg cgtgtgctga      540
aggacgttga ttaa                                                       554

<210> SEQ ID NO 19
<211> LENGTH: 563
<212> TYPE: DNA
<213> ORGANISM: Lactobacillus brevis

<400> SEQUENCE: 19
atggacaaga gcgagaagga aaaaatgatc accggcgagc tgttcaacgt gtacgatccg       60
gagctgttgc ggaacgtggc gcggcgcgtc agcaagtgga ggcgctgaac gagctgggtg      120
aacaggaccc ggaaaagagc cagcaactgg ttaaacgtct gttcggcgcg accggtgacc      180
aagttgaggt tcacgcgacc tttcgttgcg attacggcta aacatctac gtgggtgaaa       240 acttctttgc gaactatgac tgcaccattc tggatgttgc gccgatccgt attggcaagc      300
actgcctgct gggtccgaaa gtgcagattt acagcgttaa ccatccgcg gagccggaac      360 tgcgtcgtaa cggcgcgatg ggcattggca agccggtgac cctgggtgac gatgtgtggg      420
ttggtggcgg tgcgatcatc tgtccgggtg tgaccctggg tgataacgtg atcgttgcgg      480
cggggcgcgg ggttaccaag agcttcggta gcaacgtggt tctgggcggt aacccggcgc      540
gtgtgattaa gccgctgaaa taa                                             563

<210> SEQ ID NO 20
<211> LENGTH: 554
<212> TYPE: DNA
<213> ORGANISM: Bacillus subtilis

<400> SEQUENCE: 20
atgctgcgta ccgagaagga aaaaatggcg gcgggtgagc tgtacaacag cgaagaccag       60
caactgctgc tggagcgtaa gcacgcgcgt cagctgatcc gtcaatataa cgaaaccccg      120
gaagacgatg cggtgcgtac caagctgctg aaagaactgc tgggtagcgt gggcgatcag      180
gttaccatcc tgccgacctt ccgttgcgac tacggttatc acatccacat tggcgatcac      240
accttcgtga actttgactg cgttattctg gatgtgtgcg aggttcgtat cggctgccac      300
tgcctgattg cgccgggtgt tcacatctac accgcgggcc accgctgga ccgattgag       360 cgtaagagcg gtaaagaatt tggcaaaccg gtgaccattg tgatcaggt ttggatcggt      420 ggccgtgcgg tgattaatcc gggtgtgacc atcggcgaca acgcggtgat tgcgagcggc      480
agcgtggtta ccaaggatgt tccggcgaac accgggttgg tggcaacccg gcgcgtattc      540
tgaaacaact gtaa                                                       554

<210> SEQ ID NO 21
<211> LENGTH: 563
<212> TYPE: DNA
<213> ORGANISM: Pseudomonas putida

<400> SEQUENCE: 21
atgagcctga gcgagaagca aaaatgctg accggtcaac tgtatcatgc gggttgcccg       60
gagctgcaag cggaacaaat tgcgaacaag cactggatgc accgttataa caacagcgtg      120
gaactgtgaa cgacgcgcgt cacggtctgc tggttgagca cttcggccaa gtgggtgaag      180
gcgcggttat tcgtccgccg tttactgcga ctacggtta aacatcagc gtgggccgta      240 acaccttcat gaacttaact gcgtgatcct ggatgtggtt ccggttcgta tcggtgacga      300
ttgccagatt ggcccgaacg gcaaatctat accgcggacc accgctgga cccggaagtg      360
```

```
cgtcgtagcg gtctggaaag cggccgtacc gtgaccattg gtgacaacgt ttggatcggt    420
ggcgcggcga tcattctgcc gggtgtgacc atcggcgaca cgcgattgt tggtgcgggc     480 agcgtggtta cccgtgatgt tccggcgggg cgaccgtggt tggtaacccg gcgcgtgttc    540
gtcagccgga tcagggtcaa taa                                            563

<210> SEQ ID NO 22
<211> LENGTH: 48
<212> TYPE: DNA
<213> ORGANISM: Artificial Sequence
<220> FEATURE:
<223> OTHER INFORMATION: Sc-gpp2-F

<400> SEQUENCE: 22
tgctgcagag gaggtaattt atatgggatt gactactaaa cctctatc                 48

<210> SEQ ID NO 23
<211> LENGTH: 29
<212> TYPE: DNA
<213> ORGANISM: Artificial Sequence
<220> FEATURE:
<223> OTHER INFORMATION: Sc-gpp2-R

<400> SEQUENCE: 23
cccaagctta ccatttcaac agatcgtcc                                      29

<210> SEQ ID NO 24
<211> LENGTH: 660
<212> TYPE: DNA
<213> ORGANISM: Artificial Sequence
<220> FEATURE:
<223> OTHER INFORMATION: pSTV28 VECTOR

<400> SEQUENCE: 24
atggagaaaa aaatcactgg atataccacc gttgatatat cccaatggca tcgtaaagaa    60
cattttgagg catttcagtc agttgctcaa tgtacctata accagaccgt tcagctggat    120
attacggcct ttttaaagac cgtaaagaaa aataagcaca gtttatatcc ggcctttatt    180
cacattcttg cccgcctgat gaatgctcat ccggaatttc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt tccctaaagg gtttattgag    420 aatatgttt tcgtctcagc caatccctgg gtgagtttca ccagttttga tttaaacgtg    480
gccaatatgg acaacttctt cgcccccgtt ttcaccatgg gcaaatatta tacgcaaggc    540
gacaaggtgc tgatgccgct ggcgattcag gttcatcatg ccgtctgtga tggcttccat    600
gtcggcagaa tgcttaatga attacaacag tactgcgatg agtggcaggg cggggcgtaa   660

<210> SEQ ID NO 25
<211> LENGTH: 636
<212> TYPE: DNA
<213> ORGANISM: Bacillus cereus

<400> SEQUENCE: 25
atggacttcc accagatcga cattgatcgt tggaaccgta agccgtactt tgagcactat    60
atcaaggggt aagtgcagct acagcgtgac cgcgaacctg aacgttaccg cgctgctgaa    120
cggcctgcta aaaaaacatg aagctgtacc cggcgttcat ctatatgatt agccgtgtgg    180
```

```
ttaacagcca catcgagtcc gtaccgcgtt taacgataag ggtcagctgg gctactggga      240
acaaatggtg ccgacctata cattttccac aaagaggaca aaacctttag cgcgatgtgg      300
accgaataca gcagcgattt cagcctttt acaagaacta cctgcaagac atcgatcgtt       360
atggtgacaa gaaaggcctg tgggtgaaag gaacgttccg cgcacacct tcagcattag      420 cgcgctgccg tgggttagct tcaccggttt tcaacgaacc tgtacaacgg cgagtatctg      480
ctgccgatca ttaccctggg caagtacttt agcgatggca aaccgtgtgc ctgccgatca      540
gcctgcaagt tcaccacgcg gtttgcgacg gttatcacgt tagagttcat taacgaactg      600
caaaaactgg cggatagctt tgaggaatgg ctgtaa                                636

<210> SEQ ID NO 26
<211> LENGTH: 633
<212> TYPE: DNA
<213> ORGANISM: Pseudomonas aeruginosa

<400> SEQUENCE: 26
atgagctaca cccgtgttga catcagcagc tggaaccgtc gtgagcactt tgaaattttc       60
cgtggtatgg ccaatgcacc tttagccaga ccgttcaact ggacatcacc cgtctgctgg      120
atttcacccg taccgtggtt accgttttta tccggtgttc atccacagca ttgcgaaggt      180
ggttaaccgt tcccgggta ccgtatggcg atgaaaggcg acgaactgat tgtgtgggat       240
tgcgttcacc cgaactatac caccttcac ccggacaccg aaacctttag cagcttctgg       300
agccactacc acgacgatct ggcgcgttcc tggcggagta tagcatggac cgtgaaaagt      360
accgtaacga tcacagctat tttccgaaag gttcatcgaa aacgtgtttt atgttagcgc      420
gaacccgtgg gttagcttca ccagcttcga ttttaacttc gcgagcgcga caacttctt      480 tgcgccgctg tttaccgtgg gcaagtacta tagccaagcg ggtaaaaccc tggtgccgct      540
ggcggtgcaa gttcaccatg cggtttgcga tggttttcat gcggccgtct ggtgaccgag      600
ctgcaaaagc tgtgcgatga agcgggtggc taa                                  633

<210> SEQ ID NO 27
<211> LENGTH: 655
<212> TYPE: DNA
<213> ORGANISM: Clostridium acetobutylicum

<400> SEQUENCE: 27
atgaacagca acttccacgc gatcgacatg aacacctacc cgcgtgcgca cacctacaac       60
tattttacaa gaccgtgagc accctgatct atagcatcaa cattaccctg atgttacca      120 ttctgcgtgc gacctgaaga acaaaggtct gaaattcttt ccggcgtacg tgtatctggt      180
tacccgtgcg atcggtcgca ccaggagttc ctgatggcga ttcaaaacga catgctgggc      240
tactgggatt gccgtacccc gtctatccga tctttcacga ggacgataag accattacct      300
ttctgtggac cgagtacaac gaagactcga ggtgttttac aagaactaca tcagcgatat      360
tcgtgaatac ggtaacaacc acggcatcat gcgagcaagg acgctccgcc gagcaacaac      420
tacatcatta gctgcattcc gtggttcagc tttaacacct gagcatgcag ctgcaaaacg      480
cgaaaaacta ctatgcgccg atcttcgaag cgggtcgttt taccgaaacc aacggcatca      540
ttaccctgcc gctgagcatc accgtgaacc acgcgaccgt tgacgctacc acattaagct      600
gctgctggat gagctgcaat ggagcatgag ccacccgaaa gagtggattc gttaa           655

<210> SEQ ID NO 28
<211> LENGTH: 680
```

```
<212> TYPE: DNA
<213> ORGANISM: Mycobacterium abscessus

<400> SEQUENCE: 28
atgccggcgg agcacgcgct gctggttgtg atggcgacct tcgaaccgct ggacctgcaa      60
caatgccgcg tcgtgagtgg tttgaacact acctggatcg ttgcccgacc tactatagca     120
tgaccgtgga ctggacatca ccaacctgcg tgcggcggtt gacgcgagcg gtcgtaagac     180
ctatccgacc cagattgggc gctggcgacc gtggttaacc gtcacccgga gttccgtatg     240
gcgctggacg atcaaggtat ccgggtgtgt gggacgtggt tgatccggcg ttcaccgttt     300
ttaacccgga ccgtgaaacc ttgcgggtat cagcgcgcgt tacaccccgg acttcgatgc     360
gtttcacagc gaggcggcgg aactgcgagc gaatatcgta acgcgagcac cctgttcccg     420
cagggcgcgc gcgtccgcg taacgtgttg acatcagcag cattccgtgg acccgtttca     480
ccggttttac cctgaccatt gcgccgggtt ggggcacctg gcgccgatct tcaccattgg     540
taaattttac gagcaggaag ccgtaccat gatgccgcgg cgctgcaaat tcaccatgcg      600
gcggcggacg gctatcacag cgcgcgtctg gtggaggaac tcgtcaaatc attgcggacc     660
cggattgggt tcgtgattaa                                                680

<210> SEQ ID NO 29
<211> LENGTH: 663
<212> TYPE: DNA
<213> ORGANISM: Lactobacillus brevis

<400> SEQUENCE: 29
atgaccgagc tgaacaccca tgcgaccccg attgaccaga ccacctgggc gcgtcgtgaa      60
tacttcacta cttccaccaag atgatgccga ccggtttcac cctgaacgtg acatggacaa    120
tcaccgcgac caaagcgtgg ctgaccaagc acgatcgtaa attcaacccg gcgtacctgt     180
atctggttac caagctatta ccaaacaccc ggagtttcgt gtgggtcagg ttgacggcca     240
actggtggaa tacgatgttc tgcacccgag ctatagcacc tttcacggtg acgatctgac     300
cattagcaac ctgtggaccg cgtatacccg agcttcgagc agtttcacca aaactacctg     360
gcggaccagg cgacctatgg cgatcaacat accccgatgc cgaaggcgcc gcaaggtgcg     420
aacacctaca tgatcggcag cattccgtgg acccacttca acagctatac cccgctgccg     480
tttaccccgc tgaacaccct tctttccggtg atccaggcgt cgtttcacc tttaaagatg     540 gccaatggct gatgccgctg agcttcacca ttcaccacgc ggtgcggacg gctaccacgt     600
tagccagttc tttaacgagc tgcaacgtgt ttttgatcac ccggaacttg gctgaccgcg     660
taa                                                                  663

<210> SEQ ID NO 30
<211> LENGTH: 960
<212> TYPE: DNA
<213> ORGANISM: Escherichia coli

<400> SEQUENCE: 30
atgaagccgg aaaacaaact acctgttctg gaccttattt ctgctgaaat gaagaccgtt      60
gtgaatactc ttcagccgga tttaccgccc tggcccgcaa cggaacgat tgctgagcaa      120 cgacagtatt acacgcttga gcgccgattc tggaatgcgg cgctccaga aatggcaacc     180 agagcttaca tggttccaac aaaatatggg caggtgaaaa cacgtctctt ttgtccgcag     240
ccagatagcc cagcgacgct attttatttg catggaggcg gttttattct cggcaatctc    300
```

| | |
|---|---|
| gatacccacg atcgcatcat gcgcctgctg gcaagctaca gccaatgtac ggtgattggt | 360 |
| attgattaca cccttttcacc tgaagcgcgt tttccgcaag cgatagagga aattgtggct | 420 |
| gcttgttgtt atttccacca gcaggcggag gattatcaaa tcaatatgtc ccgcattggc | 480 |
| tttgccggtg attccgcagg tgccatgctg gcgctcgcca gtgcgttgtg gttgcgtgat | 540 |
| aaacagatcg attgcggtaa agttgcgggc gttttgctgt ggtatgggct ttacggatta | 600 |
| cgggattccg tgactcgtcg tctgttgggc ggtgtctggg atggcttaac gcaacaggat | 660 |
| ttgcagatgt acgaagaggc atatttaagc aacgacgcgg accgcgagtc gccgtattac | 720 |
| tgtctgttta ataatgatct cactcgcgaa gttccgccct gttttattgc cggggcggag | 780 |
| ttcgatccgc tgctggatga cagccgtctg ctttaccaga cgttagcggc gcatcagcag | 840 |
| ccctgtgagt tcaaactcta cccaggcacg ctgcacgcct ttttgcatta ttcacggatg | 900 |
| atgaaaaccg ccgacgaggc tcttcgcgac ggcgctcagt tctttaccgc tcagctttaa | 960 |

<210> SEQ ID NO 31
<211> LENGTH: 1176
<212> TYPE: DNA
<213> ORGANISM: Saccharomyces cerevisiae

<400> SEQUENCE: 31

| | |
|---|---|
| atgtctgctg ctgctgatag attaaactta acttccggcc acttgaatgc tggtagaaag | 60 |
| agaagttcct cttctgtttc tttgaaggct gccgaaaagc ctttcaaggt tactgtgatt | 120 |
| ggatctggta actggggtac tactattgcc aaggtggttg ccgaaaattg taagggatac | 180 |
| ccagaagttt tcgctccaat agtacaaatg tgggtgttcg aagaagagat caatggtgaa | 240 |
| aaattgactg aaatcataaa tactagacat caaaacgtga atacttgcc tggcatcact | 300 |
| ctacccgaca atttggttgc taatccgac ttgattgatt cagtcaagga tgtcgacatc | 360 |
| atcgttttca acattccaca tcaattttg ccccgtatct gtagccaatt gaaaggtcat | 420 |
| gttgattcac acgtcagagc tatctcctgt ctaaagggtt ttgaagttgg tgctaaaggt | 480 |
| gtccaattgc tatcctctta catcactgag gaactaggta ttcaatgtgg tgctctatct | 540 |
| ggtgctaaca ttgccaccga agtcgctcaa gaacactggt ctgaaacaac agttgcttac | 600 |
| cacattccaa aggatttcag aggcgagggc aaggacgtcg accataaggt tctaaaggcc | 660 |
| ttgttccaca gaccttactt ccacgttagt gtcatcgaag atgttgctgg tatctccatc | 720 |
| tgtggtgctt tgaagaacgt tgttgcctta ggttgtggtt tcgtcgaagg tctaggctgg | 780 |
| ggtaacaacg cttctgctgc catccaaaga gtcggttttgg gtgagatcat cagattcggt | 840 |
| caaatgtttt tcccagaatc tagagaagaa acatactacc aagagtctgc tggtgttgct | 900 |
| gatttgatca ccacctgcgc tggtggtaga acgtcaagg ttgctaggct aatggctact | 960 |
| tctggtaagg acgcctggga atgtgaaaag gagttgttga atggccaatc cgctcaaggt | 1020 |
| ttaattacct gcaaagaagt tcacgaatgg ttggaaacat gtggctctgt cgaagacttc | 1080 |
| ccattatttg aagccgtata ccaaatcgtt tacaacaact acccaatgaa gaacctgccg | 1140 |
| gacatgattg aagaattaga tctacatgaa gattag | 1176 |

<210> SEQ ID NO 32
<211> LENGTH: 753
<212> TYPE: DNA
<213> ORGANISM: Saccharomyces cerevisiae

<400> SEQUENCE: 32

| | |
|---|---|
| atgggattga ctactaaacc tctatctttg aaagttaacg ccgctttgtt cgacgtcgac | 60 |

```
ggtaccatta tcatctctca accagccatt gctgcattct ggagggattt cggtaaggac      120
aaaccttatt tcgatgctga acacgttatc caagtctcgc atggttggag aacgtttgat      180
gccattgcta agttcgctcc agactttgcc aatgaagagt atgttaacaa attagaagct      240
gaaattccgg tcaagtacgg tgaaaaatcc attgaagtcc caggtgcagt taagctgtgc      300
aacgctttga cgctctacc aaaagagaaa tgggctgtgg caacttccgg tacccgtgat       360
atggcacaaa aatggttcga gcatctggga atcaggagac caaagtactt cattaccgct      420
aatgatgtca aacagggtaa gcctcatcca gaaccatatc tgaagggcag gaatggctta      480
ggatatccga tcaatgagca agacccttcc aaatctaagg tagtagtatt tgaagacgct      540
ccagcaggta ttgccgccgg aaaagccgcc ggttgtaaga tcattggtat tgccactact      600
ttcgacttgg acttcctaaa ggaaaaaggc tgtgacatca ttgtcaaaaa ccacgaatcc      660
atcagagttg gcggctacaa tgccgaaaca gacgaagttg aattcatttt tgacgactac      720
ttatatgcta aggacgatct gttgaaatgg taa                                   753
```

```
<210> SEQ ID NO 33
<211> LENGTH: 41
<212> TYPE: DNA
<213> ORGANISM: Artificial Sequence
<220> FEATURE:
<223> OTHER INFORMATION: Ec-lacA-F

<400> SEQUENCE: 33
ctggatccag gaggtaataa aatggaacat gccaatgacc g                          41
```

```
<210> SEQ ID NO 34
<211> LENGTH: 36
<212> TYPE: DNA
<213> ORGANISM: Artificial Sequence
<220> FEATURE:
<223> OTHER INFORMATION: Ec-lacA-R

<400> SEQUENCE: 34
gtttctagat taaactgacg attcaacttt ataatc                                36
```

```
<210> SEQ ID NO 35
<211> LENGTH: 46
<212> TYPE: DNA
<213> ORGANISM: Artificial Sequence
<220> FEATURE:
<223> OTHER INFORMATION: Ec-cysE-F

<400> SEQUENCE: 35
ctggatccag gaggtaataa aatgtcgtgt gaagaactgg aaattg                     46
```

```
<210> SEQ ID NO 36
<211> LENGTH: 30
<212> TYPE: DNA
<213> ORGANISM: Artificial Sequence
<220> FEATURE:
<223> OTHER INFORMATION: Ec-cysE-R

<400> SEQUENCE: 36
gtttctagat tagatcccat ccccatactc                                       30
```

```
<210> SEQ ID NO 37
<211> LENGTH: 40
<212> TYPE: DNA
<213> ORGANISM: Artificial Sequence
<220> FEATURE:
```

<223> OTHER INFORMATION: Ec-yjgm-F

<400> SEQUENCE: 37
ctggatccag gaggtaataa aatgaataac attgcgccgc                40

<210> SEQ ID NO 38
<211> LENGTH: 29
<212> TYPE: DNA
<213> ORGANISM: Artificial Sequence
<220> FEATURE:
<223> OTHER INFORMATION: Ec-yjgM-R

<400> SEQUENCE: 38
gtttctagat tagagttcgc gcaacatcc                29

<210> SEQ ID NO 39
<211> LENGTH: 44
<212> TYPE: DNA
<213> ORGANISM: Artificial Sequence
<220> FEATURE:
<223> OTHER INFORMATION: Ec-yjaB-F

<400> SEQUENCE: 39
ctggatccag gaggtaataa aatggttatt agtattcgcc gctc                44

<210> SEQ ID NO 40
<211> LENGTH: 27
<212> TYPE: DNA
<213> ORGANISM: Artificial Sequence
<220> FEATURE:
<223> OTHER INFORMATION: Ec-yjaB-R

<400> SEQUENCE: 40
gtttctagat tacgcccccca catacgc                27

<210> SEQ ID NO 41
<211> LENGTH: 39
<212> TYPE: DNA
<213> ORGANISM: Artificial Sequence
<220> FEATURE:
<223> OTHER INFORMATION: Ec-yiiD-F

<400> SEQUENCE: 41
ctggatccag gaggtaataa aatgagccag cttccaggg                39

<210> SEQ ID NO 42
<211> LENGTH: 42
<212> TYPE: DNA
<213> ORGANISM: Artificial Sequence
<220> FEATURE:
<223> OTHER INFORMATION: Ec-nhoA-F

<400> SEQUENCE: 42
ctggatccag gaggtaataa aatgacgccc attctgaatc ac                42

<210> SEQ ID NO 43
<211> LENGTH: 28
<212> TYPE: DNA
<213> ORGANISM: Artificial Sequence
<220> FEATURE:
<223> OTHER INFORMATION: Ec-nhoA-R

<400> SEQUENCE: 43
gtttctagat tattttcccg cctccggg                28

<210> SEQ ID NO 44
<211> LENGTH: 42
<212> TYPE: DNA
<213> ORGANISM: Artificial Sequence
<220> FEATURE:
<223> OTHER INFORMATION: Ec-wecH-F

<400> SEQUENCE: 44
ctggatccag gaggtaataa aatgcagccc aaaatttact gg         42

<210> SEQ ID NO 45
<211> LENGTH: 34
<212> TYPE: DNA
<213> ORGANISM: Artificial Sequence
<220> FEATURE:
<223> OTHER INFORMATION: Ec-WecH-R

<400> SEQUENCE: 45
gtttctagat taactcacta atctgtttct gtcg               34

<210> SEQ ID NO 46
<211> LENGTH: 29
<212> TYPE: DNA
<213> ORGANISM: Artificial Sequence
<220> FEATURE:
<223> OTHER INFORMATION: Ec-yiiD-R

<400> SEQUENCE: 46
gtttctagat tactcttctt cgttcccgc                    29

<210> SEQ ID NO 47
<211> LENGTH: 45
<212> TYPE: DNA
<213> ORGANISM: Artificial Sequence
<220> FEATURE:
<223> OTHER INFORMATION: Ec-maa-F

<400> SEQUENCE: 47
ctggatccag gaggtaataa aatgagcaca gaaaagaaa agatg      45

<210> SEQ ID NO 48
<211> LENGTH: 35
<212> TYPE: DNA
<213> ORGANISM: Artificial Sequence
<220> FEATURE:
<223> OTHER INFORMATION: Ec-maa-R

<400> SEQUENCE: 48
gtttctagat tacaattttt taattattct ggctg              35

<210> SEQ ID NO 49
<211> LENGTH: 45
<212> TYPE: DNA
<213> ORGANISM: Artificial Sequence
<220> FEATURE:
<223> OTHER INFORMATION: Sc-maa-F

<400> SEQUENCE: 49
ctggatccag gaggtaataa aatgaccacc gagaaggaaa aaatg     45

<210> SEQ ID NO 50
<211> LENGTH: 29
<212> TYPE: DNA
<213> ORGANISM: Artificial Sequence
<220> FEATURE:
<223> OTHER INFORMATION: Sc-maa-R

<400> SEQUENCE: 50
gtttctagat taatccagcg gcacttcac                                     29

<210> SEQ ID NO 51
<211> LENGTH: 41
<212> TYPE: DNA
<213> ORGANISM: Artificial Sequence
<220> FEATURE:
<223> OTHER INFORMATION: Hj-maa-F

<400> SEQUENCE: 51
ctggatccag gaggtaataa aatgaccagc gagaaggaac g                       41

<210> SEQ ID NO 52
<211> LENGTH: 31
<212> TYPE: DNA
<213> ORGANISM: Artificial Sequence
<220> FEATURE:
<223> OTHER INFORMATION: Hj-maa-R

<400> SEQUENCE: 52
gtttctagat taatcaacgt ccttcagcac a                                  31

<210> SEQ ID NO 53
<211> LENGTH: 40
<212> TYPE: DNA
<213> ORGANISM: Artificial Sequence
<220> FEATURE:
<223> OTHER INFORMATION: Lb-maa-F

<400> SEQUENCE: 53
ctggatccag gaggtaataa aatggacaag agcgagaagg                         40

<210> SEQ ID NO 54
<211> LENGTH: 30
<212> TYPE: DNA
<213> ORGANISM: Artificial Sequence
<220> FEATURE:
<223> OTHER INFORMATION: Lb-maa-R

<400> SEQUENCE: 54
gtttctagat tatttcagcg gcttaatcac                                    30

<210> SEQ ID NO 55
<211> LENGTH: 42
<212> TYPE: DNA
<213> ORGANISM: Artificial Sequence
<220> FEATURE:
<223> OTHER INFORMATION: Pp-maa-F

<400> SEQUENCE: 55
ctggatccag gaggtaataa aatgagcctg agcgagaagc ac                      42

<210> SEQ ID NO 56
<211> LENGTH: 30
<212> TYPE: DNA
<213> ORGANISM: Artificial Sequence
<220> FEATURE:
<223> OTHER INFORMATION: Pp-maa-R

<400> SEQUENCE: 56
gtttctagat tattgaccct gatccggctg                                    30

<210> SEQ ID NO 57
<211> LENGTH: 40

```
<212> TYPE: DNA
<213> ORGANISM: Artificial Sequence
<220> FEATURE:
<223> OTHER INFORMATION: Bs-maa-F

<400> SEQUENCE: 57
ctggatccag gaggtaataa aatgctgcgt accgagaagg                                40

<210> SEQ ID NO 58
<211> LENGTH: 33
<212> TYPE: DNA
<213> ORGANISM: Artificial Sequence
<220> FEATURE:
<223> OTHER INFORMATION: Bs-maa-R

<400> SEQUENCE: 58
gtttctagat tacagttgtt tcagaatacg cgc                                      33

<210> SEQ ID NO 59
<211> LENGTH: 41
<212> TYPE: DNA
<213> ORGANISM: Artificial Sequence
<220> FEATURE:
<223> OTHER INFORMATION: Sc-gpd1-R

<400> SEQUENCE: 59
aatgctgcag ttaatcttca tgtagatcta attcttcaat c                             41

<210> SEQ ID NO 60
<211> LENGTH: 48
<212> TYPE: DNA
<213> ORGANISM: Artificial Sequence
<220> FEATURE:
<223> OTHER INFORMATION: Cat-F

<400> SEQUENCE: 60
ctaggagctc aggagaaata taatggagaa aaaaatcact ggatatac                      48

<210> SEQ ID NO 61
<211> LENGTH: 25
<212> TYPE: DNA
<213> ORGANISM: Artificial Sequence
<220> FEATURE:
<223> OTHER INFORMATION: Cat-R

<400> SEQUENCE: 61
ctggatcctt acgccccgcc ctgcc                                               25

<210> SEQ ID NO 62
<211> LENGTH: 26
<212> TYPE: DNA
<213> ORGANISM: Artificial Sequence
<220> FEATURE:
<223> OTHER INFORMATION: Trc-Bs.maa-F

<400> SEQUENCE: 62
agatctgagt cgacagtatc ggcggg                                              26

<210> SEQ ID NO 63
<211> LENGTH: 30
<212> TYPE: DNA
<213> ORGANISM: Artificial Sequence
<220> FEATURE:
<223> OTHER INFORMATION: Trc-Bs.maa-R

<400> SEQUENCE: 63
```
tatatttctc ctgaggatcc ccgggtaccg                                30

<210> SEQ ID NO 64
<211> LENGTH: 50
<212> TYPE: DNA
<213> ORGANISM: Artificial Sequence
<220> FEATURE:
<223> OTHER INFORMATION: Bc-Oat-F

<400> SEQUENCE: 64
ctcggtaccc ggggatcctc aggagaaata taatggactt ccaccagatc           50

<210> SEQ ID NO 65
<211> LENGTH: 42
<212> TYPE: DNA
<213> ORGANISM: Artificial Sequence
<220> FEATURE:
<223> OTHER INFORMATION: Bc-Oat-R

<400> SEQUENCE: 65
cccgccgata ctgtcgacag atcttacagc cattcctcaa ag                   42

<210> SEQ ID NO 66
<211> LENGTH: 50
<212> TYPE: DNA
<213> ORGANISM: Artificial Sequence
<220> FEATURE:
<223> OTHER INFORMATION: Ca-Oat-F

<400> SEQUENCE: 66
ctcggtaccc ggggatcctc aggagaaata taatgaacag caacttccac           50

<210> SEQ ID NO 67
<211> LENGTH: 42
<212> TYPE: DNA
<213> ORGANISM: Artificial Sequence
<220> FEATURE:
<223> OTHER INFORMATION: Ca-Oat-R

<400> SEQUENCE: 67
cccgccgata ctgtcgacag atcttaacga atccactctt tc                   42

<210> SEQ ID NO 68
<211> LENGTH: 51
<212> TYPE: DNA
<213> ORGANISM: Artificial Sequence
<220> FEATURE:
<223> OTHER INFORMATION: Lb-Oat-F

<400> SEQUENCE: 68
ctcggtaccc ggggatcctc aggagaaata taatgaccga gctgaacacc c         51

<210> SEQ ID NO 69
<211> LENGTH: 41
<212> TYPE: DNA
<213> ORGANISM: Artificial Sequence
<220> FEATURE:
<223> OTHER INFORMATION: Lb-Oat-R

<400> SEQUENCE: 69
cccgccgata ctgtcgacag atcttacgcg gtcagccaca g                    41

<210> SEQ ID NO 70
<211> LENGTH: 50
<212> TYPE: DNA
<213> ORGANISM: Artificial Sequence

```
<220> FEATURE:
<223> OTHER INFORMATION: Ma-Oat-F

<400> SEQUENCE: 70
ctcggtaccc ggggatcctc aggagaaata taatgccggc ggagcacgcg            50

<210> SEQ ID NO 71
<211> LENGTH: 49
<212> TYPE: DNA
<213> ORGANISM: Artificial Sequence
<220> FEATURE:
<223> OTHER INFORMATION: Ma-Oat-R

<400> SEQUENCE: 71
cccgccgata ctgtcgacag atcttaatca cgaacccaat ccgggtccg             49

<210> SEQ ID NO 72
<211> LENGTH: 51
<212> TYPE: DNA
<213> ORGANISM: Artificial Sequence
<220> FEATURE:
<223> OTHER INFORMATION: Pa-Oat-F

<400> SEQUENCE: 72
ctcggtaccc ggggatcctc aggagaaata taatgagcta cacccgtgtt g          51

<210> SEQ ID NO 73
<211> LENGTH: 41
<212> TYPE: DNA
<213> ORGANISM: Artificial Sequence
<220> FEATURE:
<223> OTHER INFORMATION: Pa-Oat-R

<400> SEQUENCE: 73
cccgccgata ctgtcgacag atcttagcca cccgcttcat c                     41

<210> SEQ ID NO 74
<211> LENGTH: 46
<212> TYPE: DNA
<213> ORGANISM: Artificial Sequence
<220> FEATURE:
<223> OTHER INFORMATION: Ec-aes-F

<400> SEQUENCE: 74
ctggatccgt cacccaaccc tttatgaagc cggaaaacaa actacc                46

<210> SEQ ID NO 75
<211> LENGTH: 34
<212> TYPE: DNA
<213> ORGANISM: Artificial Sequence
<220> FEATURE:
<223> OTHER INFORMATION: Ec-aes-R

<400> SEQUENCE: 75
tatcgtcgac ttaaagctga gcggtaaaga actg                             34

<210> SEQ ID NO 76
<211> LENGTH: 48
<212> TYPE: DNA
<213> ORGANISM: Artificial Sequence
<220> FEATURE:
<223> OTHER INFORMATION: Sc-gpd1-F

<400> SEQUENCE: 76
gcggatccag gaggtaataa aatgtctgct gctgctgata gattaaac              48
```

<210> SEQ ID NO 77
<211> LENGTH: 2999
<212> TYPE: DNA
<213> ORGANISM: Artificial Sequence
<220> FEATURE:
<223> OTHER INFORMATION: pSTV28 VECTOR

<400> SEQUENCE: 77

```
aaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccctg gcggctccct     960 cgtgcgctct cctgttcctg cctttcggtt taccggtgtc attccgctgt tatggccgcg    1020
tttgtctcat tccacgcctg acactcagtt ccgggtaggc agttcgctcc aagctggact    1080
gtatgcacga accccccgtt cagtccgacc gctgcgcctt atccggtaac tatcgtcttg    1140
agtccaaccc ggaaagacat gcaaaagcac cactggcagc agccactggt aattgattta    1200
gaggagttag tcttgaagtc atgcgccggt taaggctaaa ctgaaaggac aagttttggt    1260
gactgcgctc ctccaagcca gttacctcgg ttcaaagagt tggtagctca gagaaccttc    1320
gaaaaaccgc cctgcaaggc ggttttttcg ttttcagagc aagagattac gcgcagacca    1380
aaacgatctc aagaagatca tcttattaat cagataaaat atttctagat tcagtgcaa    1440 tttatctctt caaatgtagc acctgaagtc agccccatac gatataagtt gtaattctca    1500
tgtttgacag cttatcatcg ataagctcat cgccattca ggctgcgcaa ctgttgggaa    1560
gggcgatcgg tgcgggcctc ttcgctatta cgccagctgg cgaaagggggg atgtgctgca    1620 aggcgattaa gttgggtaac gccagggttt cccagtcac gacgttgtaa aacgacggcc    1680
agtgccaagc ttgcatgcct gcaggtcgac tctagaggat ccccgggtac cgagctcgaa    1740
ttcgtaatca tggtcatagc tgtttcctgt gtgaaattgt tatccgctca caattccaca    1800
caacatacga gccggaagca taaagtgtaa agcctgggt gcctaatgag tgagctaact    1860
cacattaatt gcgttgcgct cactgcccgc tttccagtcg ggaaacctgt cgtgccagct    1920
gcattaatga atcggccaac gcgcggggag aggcggtttg cgtattggaa cgccatgagc    1980
ggcctcattt cttattctga gttacaacag tccgcaccgc tgtccggtag ctccttccgg    2040
tgggcgcggg gcatgactat cgtcgccgca cttatgactg tcttctttat catgcaactc    2100
```

```
gtaggacagg tgccggcagc gcccaacagt cccccggcca cggggcctgc caccataccc    2160
acgccgaaac aagcgccctg caccattatg ttccggatct gcatcgcagg atgctgctgg    2220
ctaccctgtg aacacctac atctgtatta acgaagcgct aaccgttttt atcaggctct     2280
gggaggcaga ataaatgatc atatcgtcaa ttattacctc cacggggaga gcctgagcaa    2340
actggcctca ggcatttgag aagcacacgg tcacactgct tccggtagtc aataaaccgg    2400
taaaccagca atagacataa gcggctattt aacgaccctg ccctgaaccg acgaccgggt    2460
cgaatttgct ttcgaatttc tgccattcat ccgcttatta tcacttattc aggcgtagca    2520
ccaggcgttt aagggcacca ataactgcct taaaaaaatt acgccccgcc ctgccactca    2580
tcgcagtact gttgtaattc attaagcatt ctgccgacat ggaagccatc acaaacggca    2640
tgatgaacct gaatcgccag cggcatcagc accttgtcgc cttgcgtata atatttgccc    2700
atggtgaaaa cggggggcgaa gaagttgtcc atattggcca cgtttaaatc aaaactggtg    2760
aaactcaccc agggattggc tgagacgaaa aacatattct caataaaccc tttagggaaa    2820
taggccaggt tttcaccgta acacgccaca tcttgcgaat atatgtgtag aaactgccgg    2880
aaatcgtcgt ggtattcact ccagagcgat gaaaacgttt cagtttgctc atggaaaacg    2940
gtgtaacaag ggtgaacact atcccatatc accagctcac cgtctttcat tgccatacg     2999
```

<210> SEQ ID NO 78
<211> LENGTH: 4176
<212> TYPE: DNA
<213> ORGANISM: Artificial Sequence
<220> FEATURE:
<223> OTHER INFORMATION: pTrc99A VECTOR

<400> SEQUENCE: 78

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga    240
taacaatttc acacaggaaa cagaccatgg aattcgagct cggtacccgg ggatcctcta    300
gagtcgacct gcaggcatgc aagcttggct gttttggcgg atgagagaag attttcagcc    360
tgatacagat taaatcagaa cgcagaagcg gtctgataaa acagaatttg cctggcggca    420
gtagcgcggt ggtcccacct gaccccatgc cgaactcaga agtgaaacgc cgtagcgccg    480
atggtagtgt ggggtctccc catgcgagag taggaactg ccaggcatca ataaaacga    540 aaggctcagt cgaaagactg ggcctttcgt tttatctgtt gtttgtcggt gaacgctctc    600
ctgagtagga caaatccgcc gggagcggat ttgaacgttg cgaagcaacg gcccggaggg   660
tggcgggcag gacgcccgcc ataaactgcc aggcatcaaa ttaagcagaa ggccatcctg    720
acggatggcc ttttttgcgtt tctacaaact cttttttgttt attttttctaa atacattcaa    780 atatgtatcc gctcatgaga caataaccct gataaatgct tcaataatat tgaaaaagga    840
agagtatgag tattcaacat ttccgtgtcg cccttattcc cttttttgcg gcattttgcc    900
ttcctgtttt tgctcaccca gaaacgctgg tgaaagtaaa agatgctgaa gatcagttgg    960
gtgcacgagt gggttacatc gaactggatc tcaacagcgg taagatcctt gagagttttc   1020
gccccgaaga acgttttcca atgatgagca cttttaaagt tctgctatgt ggcgcggtat    1080
tatcccgtgt tgacgccggg caagagcaac tcggtcgccg catacactat tctcagaatg    1140
```

```
acttggttga gtactcacca gtcacagaaa agcatcttac ggatggcatg acagtaagag      1200
aattatgcag tgctgccata accatgagtg ataacactgc ggccaactta cttctgacaa      1260
cgatcggagg accgaaggag ctaaccgctt ttttgcacaa catgggggat catgtaactc      1320
gccttgatcg ttgggaaccg gagctgaatg aagccatacc aaacgacgag cgtgacacca      1380
cgatgcctac agcaatggca caacgttgc gcaaactatt aactggcgaa ctacttactc       1440
tagcttcccg gcaacaatta atagactgga tggaggcgga taaagttgca ggaccacttc      1500
tgcgctcggc ccttccggct ggctggttta ttgctgataa atctggagcc ggtgagcgtg      1560
ggtctcgcgg tatcattgca gcactggggc cagatggtaa gccctcccgt atcgtagtta      1620
tctacacgac ggggagtcag gcaactatgg atgaacgaaa tagacagatc gctgagatag      1680
gtgcctcact gattaagcat tggtaactgt cagaccaagt ttactcatat atactttaga      1740
ttgatttaaa acttcatttt taatttaaaa ggatctaggt gaagatcctt tttgataatc      1800
tcatgaccaa aatcccttaa cgtgagtttt cgttccactg agcgtcagac cccgtagaaa      1860
agatcaaagg atcttcttga gatccttttt ttctgcgcgt aatctgctgc ttgcaaacaa      1920
aaaaaccacc gctaccagcg gtggtttgtt tgccggatca agagctacca actctttttc      1980
cgaaggtaac tggcttcagc agagcgcaga taccaaatac tgtccttcta gtgtagccgt      2040
agttaggcca ccacttcaag aactctgtag caccgcctac atacctcgct ctgctaatcc      2100
tgttaccagt ggctgctgcc agtggcgata agtcgtgtct taccggggttg gactcaagac      2160 gatagttacc ggataaggcg cagcggtcgg gctgaacggg gggttcgtgc acacagccca      2220
gcttggagcg aacgacctac accgaactga gatacctaca gcgtgagcta tgagaaagcg      2280
ccacgcttcc cgaagggaga aaggcggaca ggtatccggt aagcggcagg gtcggaacag      2340
gagagcgcac gagggagctt ccaggggaa acgcctggta tctttatagt cctgtcgggt       2400
ttcgccacct ctgacttgag cgtcgatttt tgtgatgctc gtcaggggg cggagcctat        2460 ggaaaaacgc cagcaacgcg ccttttttac ggttcctggc cttttgctgg cttttgctc        2520 acatgttctt tcctgcgtta tcccctgatt ctgtggataa ccgtattacc gcctttgagt      2580
gagctgatac cgctcgccgc agccgaacga ccgagcgcag cgagtcagtg agcgaggaag      2640
cggaagagcg cctgatgcgg tatttttctcc ttacgcatct gtgcggtatt tcacaccgca     2700
tatggtgcac tctcagtaca atctgctctg atgccgcata gttaagccag tatacactcc      2760
gctatcgcta cgtgactggg tcatggctgc gccccgacac ccgccaacac ccgctgacgc      2820
gccctgacgg gcttgtctgc tcccggcatc cgcttacaga caagctgtga ccgtctccgg      2880
gagctgcatg tgtcagaggt tttcaccgtc atcaccgaaa cgcgcgaggc agcagatcaa      2940
ttcgcgcgcg aaggcgaagc ggcatgcatt tacgttgaca ccatcgaatg gtgcaaaacc      3000
tttcgcggta tggcatgata gcgcccggaa gagagtcaat tcagggtggt gaatgtgaaa      3060
ccagtaacgt tatacgatgt cgcagagtat gccggtgtct cttatcagac cgtttcccgc      3120
gtggtgaacc aggccagcca cgtttctgcg aaaacgcggg aaaaagtgga agcggcgatg      3180
gcggagctga attacattcc caaccgcgtg gcacaacaac tggcgggcaa acagtcgttg      3240
ctgattggcg ttgccacctc cagtctggcc ctgcacgcgc cgtcgcaaat tgtcgcggcg      3300
attaaatctc gcgccgatca actgggtgcc agcgtggtgg tgtcgatggt agaacgaagc      3360
ggcgtcgaag cctgtaaagc ggcggtgcac aatcttctcg cgcaacgcgt cagtgggctg      3420
atcattaact atccgctgga tgaccaggat gccattgctg tggaagctgc ctgcactaat      3480
gttccggcgt tatttcttga tgtctctgac cagacaccca tcaacagtat tattttctcc      3540
```

```
catgaagacg gtacgcgact gggcgtggag catctggtcg cattgggtca ccagcaaatc    3600
gcgctgttag cgggcccatt aagttctgtc tcggcgcgtc tgcgtctggc tggctggcat    3660
aaatatctca ctcgcaatca aattcagccg atagcggaac gggaaggcga ctggagtgcc    3720
atgtccggtt ttcaacaaac catgcaaatg ctgaatgagg gcatcgttcc cactgcgatg    3780
ctggttgcca acgatcagat ggcgctgggc gcaatgcgcg ccattaccga gtccgggctg    3840
cgcgttggtg cggatatctc ggtagtggga tacgacgata ccgaagacag ctcatgttat    3900
atcccgccgt taaccaccat caaacaggat tttcgcctgc tggggcaaac cagcgtggac    3960
cgcttgctgc aactctctca gggccaggcg gtgaagggca atcagctgtt gcccgtctca    4020
ctggtgaaaa gaaaaaccac cctggcgccc aatacgcaaa ccgcctctcc ccgcgcgttg    4080
gccgattcat taatgcagct ggcacgacag gtttcccgac tggaaagcgg gcagtgagcg    4140
caacgcaatt aatgtgagtt agcgcgaatt gatctg                              4176

<210> SEQ ID NO 79
<211> LENGTH: 5369
<212> TYPE: DNA
<213> ORGANISM: Artificial Sequence
<220> FEATURE:
<223> OTHER INFORMATION: pET28a (+) VECTOR

<400> SEQUENCE: 79
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttgt     180
cgacggagct cgaattcgga tccgcgaccc atttgctgtc caccagtcat gctagccata     240
tggctgccgc gcggcaccag gccgctgctg tgatgatgat gatgatggct gctgcccatg     300
gtatatctcc ttcttaaagt taaacaaaat tatttctaga gggaattgt tatccgctca     360 caattcccct atagtgagtc gtattaattt cgcgggatcg agatctcgat cctctacgcc     420
ggacgcatcg tggccggcat caccggcgcc acaggtgcgg ttgctggcgc ctatatcgcc     480
gacatcaccg atggggaaga tcgggctcgc cacttcgggc tcatgagcgc ttgtttcggc     540
gtgggtatgg tggcaggccc cgtggccggg ggactgttgg gcgccatctc cttgcatgca     600
ccattccttg cggcggcggt gctcaacggc ctcaacctac tactgggctg cttcctaatg     660
caggagtcgc ataagggaga gcgtcgagat cccggacacc atcgaatggc gcaaaacctt     720
tcgcggtatg gcatgatagc gcccggaaga gagtcaattc agggtggtga atgtgaaacc     780
agtaacgtta tacgatgtcg cagagtatgc cggtgtctct tatcagaccg tttcccgcgt     840
ggtgaaccag gccagccacg tttctgcgaa acgcgggaa aaagtggaag cggcgatggc     900
ggagctgaat tacattccca accgcgtggc acaacaactg gcgggcaaac agtcgttgct     960
gattggcgtt gccacctcca gtctggccct gcacgcgccg tcgcaaattg tcgcggcgat    1020
taaatctcgc gccgatcaac tgggtgccag cgtggtggtg tcgatggtag aacgaagcgg    1080
cgtcgaagcc tgtaaagcgg cggtgcacaa tcttctcgcg caacgcgtca gtgggctgat    1140
cattaactat ccgctggatg accaggatgc cattgctgtg gaagctgcct gcactaatgt    1200
tccggcgtta tttcttgatg tctctgacca gacacccatc aacagtatta ttttctccca    1260
tgaagacggt acgcgactgg gcgtggagca tctggtcgca ttgggtcacc agcaaatcgc    1320
gctgttagcg ggcccattaa gttctgtctc ggcgcgtctg cgtctggctg ctggcataa    1380
```

```
atatctcact cgcaatcaaa ttcagccgat agcggaacgg gaaggcgact ggagtgccat    1440
gtccggtttt caacaaacca tgcaaatgct gaatgagggc atcgttccca ctgcgatgct    1500
ggttgccaac gatcagatgg cgctgggcgc aatgcgcgcc attaccgagt ccgggctgcg    1560
cgttggtgcg gatatctcgg tagtgggata cgacgatacc gaagacagct catgttatat    1620
cccgccgtta accaccatca aacaggattt tcgcctgctg gggcaaacca gcgtggaccg    1680
cttgctgcaa ctctctcagg gccaggcggt gaagggcaat cagctgttgc ccgtctcact    1740
ggtgaaaaga aaaaccaccc tggcgcccaa tacgcaaacc gcctctcccc gcgcgttggc    1800
cgattcatta atgcagctgg cacgacaggt ttcccgactg gaaagcgggc agtgagcgca    1860
acgcaattaa tgtaagttag ctcactcatt aggcaccggg atctcgaccg atgcccttga    1920
gagccttcaa cccagtcagc tccttccggt gggcgcgggg catgactatc gtcgccgcac    1980
ttatgactgt cttctttatc atgcaactcg taggacaggt gccggcagcg ctctgggtca    2040
ttttcggcga ggaccgcttt cgctggagcg cgacgatgat cggcctgtcg cttgcggtat    2100
tcggaatctt gcacgccctc gctcaagcct tcgtcactgg tcccgccacc aaacgtttcg    2160
gcgagaagca ggccattatc gccggcatgg cggccccacg ggtgcgcatg atcgtgctcc    2220
tgtcgttgag gacccggcta ggctggcggg gttgccttac tggttagcag aatgaatcac    2280
cgatacgcga gcgaacgtga agcgactgct gctgcaaaac gtctgcgacc tgagcaacaa    2340
catgaatggt cttcggtttc cgtgtttcgt aaagtctgga aacgcggaag tcagcgccct    2400
gcaccattat gttccggatc tgcatcgcag gatgctgctg gctaccctgt ggaacaccta    2460
catctgtatt aacgaagcgc tggcattgac cctgagtgat ttttctctgg tcccgccgca    2520
tccataccgc cagttgttta ccctcacaac gttccagtaa ccgggcatgt tcatcatcag    2580
taacccgtat cgtgagcatc ctctctcgtt tcatcggtat cattaccccc atgaacagaa    2640
atccccctta cacggaggca tcagtgacca acaggaaaa aaccgccctt aacatggccc    2700
gctttatcag aagccagaca ttaacgcttc tggagaaact caacgagctg gacgcggatg    2760
aacaggcaga catctgtgaa tcgcttcacg accacgctga tgagctttac cgcagctgcc    2820
tcgcgcgttt cggtgatgac ggtgaaaacc tctgacacat gcagctcccg gagacggtca    2880
cagcttgtct gtaagcggat gccgggagca gacaagcccg tcagggcgcg tcagcgggtg    2940
ttggcgggtg tcggggcgca gccatgaccc agtcacgtag cgatagcgga gtgtatactg    3000
gcttaactat gcggcatcag agcagattgt actgagagtg caccatatat gcggtgtgaa    3060
ataccgcaca gatgcgtaag gagaaaatac cgcatcaggc gctcttccgc ttcctcgctc    3120
actgactcgc tgcgctcggt cgttcggctg cggcgagcgg tatcagctca ctcaaaggcg    3180
gtaatacggt tatccacaga atcagggat aacgcaggaa agaacatgtg agcaaaaggc    3240
cagcaaaagg ccaggaaccg taaaaaggcc gcgttgctgg cgttttccca taggctccgc    3300
ccccctgacg agcatcacaa aaatcgacgc tcaagtcaga ggtggcgaaa cccgacagga    3360
ctataaagat accaggcgtt tccccctgga agctccctcg tgcgctctcc tgttccgacc    3420
ctgccgctta ccggatacct gtccgccttt ctcccttcgg gaagcgtggc gctttctcat    3480
agctcacgct gtaggtatct cagttcggtg taggtcgttc gctccaagct gggctgtgtg    3540
cacgaacccc ccgttcagcc cgaccgctgc gccttatccg gtaactatcg tcttgagtcc    3600
aacccggtaa gacacgactt atcgccactg gcagcagcca ctggtaacag gattagcaga    3660
gcgaggtatg taggcggtgc tacagagttc ttgaagtggt ggcctaacta cggctacact    3720
agaaggacag tatttggtat ctgcgctctg ctgaagccag ttaccttcgg aaaaagagtt    3780
```

```
ggtagctctt gatccggcaa acaaaccacc gctggtagcg gtggtttttt tgtttgcaag    3840
cagcagatta cgcgcagaaa aaaggatct caagaagatc ctttgatctt ttctacgggg    3900
tctgacgctc agtggaacga aaactcacgt taagggattt tggtcatgaa caataaaact    3960
gtctgcttac ataaacagta atacaagggg tgttatgagc catattcaac gggaaacgtc    4020
ttgctctagg ccgcgattaa attccaacat ggatgctgat ttatatgggt ataaatgggc    4080
tcgcgataat gtcgggcaat caggtgcgac aatctatcga ttgtatggga agcccgatgc    4140
gccagagttg tttctgaaac atggcaaagg tagcgttgcc aatgatgtta cagatgagat    4200
ggtcagacta aactggctga cggaatttat gcctcttccg accatcaagc attttatccg    4260
tactcctgat gatgcatggt tactcaccac tgcgatcccc gggaaaacag cattccaggt    4320
attagaagaa tatcctgatt caggtgaaaa tattgttgat gcgctggcag tgttcctgcg    4380
ccggttgcat tcgattcctg tttgtaattg tccttttaac agcgatcgcg tatttcgtct    4440
cgctcaggcg caatcacgaa tgaataacgg tttggttgat gcgagtgatt ttgatgacga    4500
gcgtaatggc tggcctgttg aacaagtctg gaaagaaatg cataaacttt tgccattctc    4560
accggattca gtcgtcactc atggtgattt ctcacttgat aaccttattt ttgacgaggg    4620
gaaattaata ggttgtattg atgttggacg agtcggaatc gcagaccgat accaggatct    4680
tgccatccta tggaactgcc tcggtgagtt ttctccttca ttacagaaac ggcttttttca    4740 aaaatatggt attgataatc ctgatatgaa taaattgcag tttcatttga tgctcgatga    4800 gttttctaa gaattaattc atgagcggat acatatttga atgtatttag aaaaataaac    4860 aaatagggt tccgcgcaca tttccccgaa aagtgccacc tgaaattgta acgttaata    4920 ttttgttaaa attcgcgtta aattttttgtt aaatcagctc attttttaac caataggccg    4980
aaatcggcaa aatcccttat aaatcaaaag aatagaccga gatagggttg agtgttgttc    5040
cagtttggaa caagagtcca ctattaaaga acgtggactc caacgtcaaa gggcgaaaaa    5100
ccgtctatca gggcgatggc ccactacgtg aaccatcacc ctaatcaagt ttttgggggt    5160
cgaggtgccg taaagcacta atcggaacc ctaagggag cccccgattt agagcttgac    5220
ggggaaagcc ggcgaacgtg gcgagaaagg aagggaagaa agcgaaagga gcgggcgcta    5280
gggcgctggc aagtgtagcg gtcacgctgc gcgtaaccac cacacccgcc gcgcttaatg    5340
cgccgctaca gggcgcgtcc cattcgcca                                     5369

<210> SEQ ID NO 80
<211> LENGTH: 612
<212> TYPE: DNA
<213> ORGANISM: Escherichia coli

<400> SEQUENCE: 80
atgaacatgc caatgaccga agaataaga gcaggcaagc tatttaccga tatgtgcgaa      60
ggcttaccgg aaaaaagact tcgtgggaaa acgttaatgt atgagtttaa tcactcgcat     120
ccatcagaag ttgaaaaaag agaaagcctg attaagaaaa tgtttgccac ggtaggggaa     180
aacgcctggg tagaaccgcc tgtctatttc tcttacggtt ccaacatcca tataggccgc     240
aatttttatg caaatttcaa tttaaccatt gtcgatgact acacggtaac aatcggtgat     300
aacgtactga ttgcacccaa cgttactctt tccgttacgg acaccctgt acaccatgaa     360 ttgagaaaaa acggcgagat gtactctttt ccgataacga ttggcaataa cgtctggatc     420
ggaagtcatg tggttattaa tccaggcgtc accatcgggg ataattctgt tattggcgcg     480
```

```
ggtagtatcg tcacaaaaga cattccacca aacgtcgtgg cggctggcgt tccttgtcgg    540
gttattcgcg aaataaacga ccgggataag cactattatt tcaaagatta taaagttgaa    600
tcgtcagttt aa                                                        612
```

<210> SEQ ID NO 81
<211> LENGTH: 822
<212> TYPE: DNA
<213> ORGANISM: Escherichia coli

<400> SEQUENCE: 81

```
atgtcgtgtg aagaactgga aattgtctgg aacaatatta agccgaagc cagaacgctg     60 gcggactgtg agccaatgct ggccagtttt taccacgcga cgctactcaa gcacgaaaac    120
cttggcagtg cactgagcta catgctggcg aacaagctgt catcgccaat tatgcctgct    180
attgctatcc gtgaagtggt ggaagaagcc tacgccgctg acccggaaat gatcgcctct    240
gcggcctgtg atattcaggc ggtgcgtacc cgcgacccgg cagtcgataa atactcaacc    300
ccgttgttat acctgaaggg ttttcatgcc ttgcaggcct atcgcatcgg tcactggttg    360
tggaatcagg ggcgtcgcgc actggcaatc tttctgcaaa accaggtttc tgtgacgttc    420
caggtcgata ttcacccggc agcaaaaatt ggtcgcggta tcatgcttga ccacgcgaca    480
ggcatcgtcg ttggtgaaac ggcggtgatt gaaaacgacg tatcgattct gcaatctgtg    540
acgcttggcg gtacgggtaa atctggtggt gaccgtcacc cgaaaattcg tgaaggtgtg    600
atgattggcg cgggcgcgaa atcctcggc  aatattgaag ttgggcgcgg cgcgaagatt    660
ggcgcaggtt ccgtggtgct gcaaccggtg ccgccgcata ccaccgccgc tggcgttccg    720
gctcgtattg tcggtaaacc agacagcgat aagccatcaa tggatatgga ccagcatttc    780
aacggtatta accatacatt tgagtatggg gatgggatct aa                       822
```

<210> SEQ ID NO 82
<211> LENGTH: 996
<212> TYPE: DNA
<213> ORGANISM: Escherichia coli

<400> SEQUENCE: 82

```
atgcagccca aaatttactg gattgataac ctgcgaggga tagcgtgttt aatggtggtg     60
atgattcaca ccactacctg gtatgtgacc aatgctcata gtgttagccc cgtcacatgg    120
gatatcgcca atgttctgaa ttctgcctct cgtgtcagcg tgccgctatt tttcatgatt    180
tccggctatc tctttttttgg cgaacgcagc gcccagccgc gccatttctt gcgtatcggc    240
ttatgtctga ttttttatag cgcaatcgca ctgctctaca ttgcgctgtt tacctccatc    300
aatatggagt tagcgctgaa aaacctgctg caaaagccag tgttttacca cttgtggttt    360
ttcttcgcga ttgcggtgat ttatctggtt tcaccgctga ttcaggtgaa gaacgtcggc    420
ggaaaaatgt tgctggtgct aatggcggtt attggcatta tcgctaaccc aaacacagtg    480
ccgcagaaaa ttgacggttt tgaatggctg ccaattaact tatatatcaa tggcgatact    540
ttttactaca ttctgtatgg catgttgggc cgcgctatag ggatgatgga cacacagcat    600
aaagcactgt cgtgggtgag cgccgcgctg tttgcgacgg gggttttat  tatctctcgc    660 gggacattat atgaattgca gtggcgcgga aattttgccg atacctggta tctttactgt    720
gggccgatgg ttttatctg  cgcaatcgcg ctattgactc tggttaaaaa cacgctggat    780
acgcgtacca ttcgcggact tggcttaatc tcccgccatt cattgggtat atacggattc    840
cacgccttga ttatccatgc gctgcgcacc cggggaattg agcttaaaaa ttggccaata    900
```

```
ctggatatta tttggatctt ttgcgcgacg ttggcagcga gtttgttact ttctatgctg      960
gtacaacgaa tcgacagaaa cagattagtg agttaa                                996

<210> SEQ ID NO 83
<211> LENGTH: 846
<212> TYPE: DNA
<213> ORGANISM: Escherichia coli

<400> SEQUENCE: 83
atgacgccca ttctgaatca ctattttgcc cgtattaact ggtcgggagc tgctgcggtc       60
aatattgata cgcttcgtgc attgcacctg aaacacaatt gcaccattcc gtttgaaaac      120
ctcgacgttt tgctgccgag ggaaatacag cttgataatc aatcgccgga agagaaactg      180
gtgatagccc gtcgtggcgg ttactgtttt gagcagaatg gcgtgtttga gcgggtgtta      240
cgcgagctgg ggtttaacgt tcgcagcttg ttagggcgcg tagtgttatc aaatccgcca      300
gcattaccgc cgcgcaccca tcgtttgctg ttggtggaac tggaagagga aaaatggatt      360
gctgatgtcg gtttcggtgg gcagacgcta accgcgccga ttcgtttagt ttccgatctc      420
gtgcagacca cgccacacgg agagtatcgg ttgttgcagg agggtgatga ttgggtgttg      480
cagtttaatc atcatcagca ttggcagtcg atgtaccgtt ttgatctctg cgagcagcaa      540
caaagcgatt atgtgatggg caatttctgg tcggcgcact ggccgcagtc gcattttcgc      600
catcatttgc tgatgtgccg ccatttgccg gacggcggca agctgacact gaccaatttt      660
cattttaccc attatgaaaa tgggcacgcg gtggagcagc gaaatctacc ggatgtggcg      720
tcattatatg ctgtgatgca agaacagttt ggtctgggcg tggatgatgc gaaacatggc      780
tttaccgtgg atgagttagc gctggtgatg gcggcgtttg atacgcaccc ggaggcggga      840
aaataa                                                                846

<210> SEQ ID NO 84
<211> LENGTH: 504
<212> TYPE: DNA
<213> ORGANISM: Escherichia coli

<400> SEQUENCE: 84
atgaataaca ttgcgccgca atcacctgta atgcgtcgcc tgacgctgca ggataatcct       60
gctatcgccc gcgtcattcg tcaggtatcc gccgaatacg tcttaccgc tgataaaggc      120 tacaccgtcg ccgatccgaa tcttgacgag ctgtatcaag tatatagtca gcctggccat      180
gcatattggg tcgttgagta cgagggtgaa gtggtcggcg cggtgggat agcgccatta      240 accgggagtg agtcggatat ttgcgaactg caaaagatgt attttcttcc ggctatccgc      300
ggcaaagggc tggcaaaaaa actggcctta atggcgatgg agcaggcgcg agagatgggt      360
ttcaaacgct gctatctgga aacgaccgct tttttaaagg aagccattgc gctttatgag      420
catttgggct tgagcatat cgactatgcg cttggctgca cgggccatgt cgattgtgaa      480
gtgcggatgt tgcgcgaact ctaa                                            504

<210> SEQ ID NO 85
<211> LENGTH: 444
<212> TYPE: DNA
<213> ORGANISM: Escherichia coli

<400> SEQUENCE: 85
atggttatta gtattcgccg ctcacggcat gaggaagggg aggaactcgt tgcgatttgg       60
```

-continued

```
tgtcgttctg tcgatgccac tcacgatttt ctatcagcag agtatcggac cgagctggag    120
gacctagttc gttccttcct gccggaagcg ccgttgtggg tcgcggttaa tgagcgggat    180
cagccggttg gatttatgtt gctaagtggg cagcatatgg atgcgctgtt tatcgatcct    240
gatgtgcgcg gctgcggcgt aggtcgggtg ctggtggagc atgcgctctc gatggcaccg    300
gaactgacaa ccaacgttaa tgagcaaaat gagcaggcgg ttgggttcta taagaaggtg    360
ggttttaagg ttacgggacg ctctgaggtg gacgatttgg ggaaaccgta tccgttgctg    420
aatctggcgt atgtgggggc gtaa                                          444

<210> SEQ ID NO 86
<211> LENGTH: 990
<212> TYPE: DNA
<213> ORGANISM: Escherichia coli

<400> SEQUENCE: 86
atgagccagc ttccagggtt gtcacgggaa acaagagaga gtatcgctat gtatcacctt     60
cgggttccac aaacagaaga agaattagag cgttactatc agtttcgctg ggaaatgttg    120
cgtaagcccc tgcatcaacc aaaaggttcg gaacgcgacg cgtgggatgc gatggcgcat    180
caccagatgg tcgtcgacga gcagggtaat ctggtggcgg taggccgact gtatattaat    240
gccgacaatg aagcgtccat tcgctttatg gccgttcatc ccgacgtgca ggacaaaggg    300
ttaggcacgc tgatggcgat gaccctggag tcggtggcgc gtcaggaagg cgttaagcgc    360
gtgacctgta gcgcccgtga agacgcggtg gagttttttcg ccaagctggg gtttgttaat    420
cagggagaaa tcaccacgcc aaccaccacg ccgattcgcc atttttttgat gattaagccc    480 gtcgccactc tggatgacat tctgcatcgc ggcgactggt gcgcgcagct gcaacaggcg    540
tggtacgaac atatcccgct tagtgaaaaa atgggcgtgc gcattcagca atataccggg    600
caaaaattta tcactaccat gccagaaacc ggcaatcaga atccgcacca tacgctgttt    660
gccgggagtt tattctcact ggcgacgctc actggttggg gacttatctg gctgatgctg    720
cgtgaacgcc acctcggcgg aacgattatt cttgcggatg cgcatatccg ctacagcaag    780
ccgattagcg gtaaacctca tgcggtagcc gacctcggtg ccttaagcgg cgatctcgac    840
cgtctggcgc gcggacgaaa agcacgggtg cagatgcagg tcgaaatctt tggcgacgag    900
acgccgggtg cagtgtttga aggcacgtat atcgttctgc ccgcgaagcc atttggcccg    960
tatgaagagg gcgggaacga agaagagtaa                                    990
```